(12) United States Patent
Rotolo et al.

(10) Patent No.: US 11,207,329 B2
(45) Date of Patent: *Dec. 28, 2021

US011207329B2

(54) METHODS FOR TREATING GI SYNDROME AND GRAFT VERSUS HOST DISEASE

(71) Applicants:Sloan Kettering Institute for Cancer Research, New York, NY (US); Board of Regents, The University of Texas System, Austin, TX (US)

(72) Inventors: Jimmy Andrew Rotolo, Port Washington, NY (US); Richard N. Kolesnick, New York, NY (US); Renata Pasqualini, Los Ranchos de Albuquerque, NM (US); Wadih Arap, Los Ranchos de Albuquerque, NM (US)

(73) Assignees: SLOAN KETTERING INSTITUTE FOR CANCER RESEARCH, New York, NY (US); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 170 days.

This patent is subject to a terminal disclaimer.

(21) Appl. No.: 15/906,868

(22) Filed: Feb. 27, 2018

(65) Prior Publication Data

US 2019/0046538 A1 Feb. 14, 2019

Related U.S. Application Data

(60) Continuation of application No. 15/437,165, filed on Feb. 20, 2017, now abandoned, which is a continuation of application No. 13/974,405, filed on Aug. 23, 2013, now Pat. No. 9,592,238, which is a division of application No. 12/599,280, filed as application No. PCT/US2008/062789 on May 6, 2008, now Pat. No. 8,562,993.

(60) Provisional application No. 60/916,298, filed on May 6, 2007.

(51) Int. Cl.
| | |
|---|---|
| *A61K 31/55* | (2006.01) |
| *C07K 16/44* | (2006.01) |
| *C07K 16/40* | (2006.01) |
| *C07K 16/28* | (2006.01) |
| *A61K 39/00* | (2006.01) |

(52) U.S. Cl.
CPC .............. *A61K 31/55* (2013.01); *C07K 16/28* (2013.01); *C07K 16/40* (2013.01); *C07K 16/44* (2013.01); *A61K 2039/505* (2013.01)

(58) Field of Classification Search
None
See application file for complete search history.

(56) References Cited

U.S. PATENT DOCUMENTS

| 4,950,649 A | 8/1990 | Rinehart |
| 5,331,093 A | 7/1994 | Ishihara et al. |
| 8,562,993 B2 | 10/2013 | Rotolo et al. |
| 2003/0165835 A1 | 9/2003 | Spies et al. |
| 2003/0190715 A1 | 10/2003 | Grosse et al. |
| 2005/0209219 A1 | 9/2005 | Gulbins |
| 2007/0237752 A1 | 10/2007 | Christensen et al. |
| 2010/0239572 A1 | 9/2010 | Rotolo et al. |

FOREIGN PATENT DOCUMENTS

| JP | 2006-505527 A | 2/2006 |
| KR | 20050014573 | 2/2005 |
| WO | WO-2005/025489 A2 | 3/2005 |
| WO | WO-2006/133450 A2 | 12/2006 |

OTHER PUBLICATIONS

Cowart et al., "Structural determinants of sphingolipid recognition by commercially available anti-ceramide antibodies," Journal of Lipid Research, vol. 43, No. 12, pp. 2042-2048 (2002).
Fan et al., "Construction and expression of 2A2 chimeric antibody 2A2 neutralising cathepsin B activity," Anticancer Research—Int'l J. of Cancer Res. and Treatment, Int'l Institute of Anticancer Research, vol. 22, No. 6C, p. 4322 (Nov. 1, 2002).
Grassme et al., "CD95 signaling via ceramide-rich membrane rafts," Journal of Biological Chemistry, vol. 276, No. 23, pp. 20589-20596 (Jun. 8, 2001).
Gulbins et al., "Physiological and pathophysiological aspects of ceramide," Am. J. Physiol. Regul. Integr. Comp. Physiol., 290, pp. R11-R26 (2006).
Gulbins et al., "Raft ceramide in molecular medicine," Oncogene, vol. 22, No. 45, pp. 7070-7077 (2003).
International Search Report, PCT/US2008/062789 (dated Oct. 7, 2008).
Kawase et al., "Increase of ceramide in adriamycin-induced HL-60 cell apoptosis: detection by a novel anti-ceramide antibody," Biochimica el Biophysica Acta, vol. 1584, No. 2-3, pp. 104-114 (2002).
Krishnamurthy et al., "Development and characterization of a novel anti-ceramide antibody","Journal of Lipid Research", vol. 48, No. 4, pp. 968-975 (2004).
Mueller et al., "Humanized porcine VCAM-specific monoclonal antibodies with chimeric IgG2/G4 constant regions block human leukocyte binding to porcine endothelial cells," Mol. Immunology, vol. 34, No. 6, pp. 441-452 (Jan. 1, 1997).
Novak et al., "Do statins have a role in preventing or treating sepsis?," Critical Care Journal, vol. 10(1), pp. 113 (Jan. 23, 2006).

(Continued)

*Primary Examiner* — Sharon X Wen
(74) *Attorney, Agent, or Firm* — Foley & Lardner LLP

(57) ABSTRACT

We have discovered that administering anti-ceramide antibody treats and prevents an array of diseases mediated by cytolytic T lymphocyte (CTLs)-induced killing and by damage to endothelial microvasculture, including radiation-induced GI syndrome, Graft vs. Host diseases, inflammatory diseases and autoimmune diseases. We have also discovered new anti-ceramide monoclonal antibodies, that have therapeutic use preferably in humanized form to treat or prevent these diseases.

6 Claims, 30 Drawing Sheets

Specification includes a Sequence Listing.

(56) References Cited

OTHER PUBLICATIONS

Oliva-Hemker et al., "Pernicious anemia and widespread absence of gastrointestinal endocrine cells in a patient with autoimmune polyglandular syndrome type I and malabsorption," Journal of Clinical Endocrinology & Metabolism, vol. 91(8), pp. 2833-2838 (May 9, 2006).
Paris et al., "Endothelial apoptosis as the primary lesion initiating intestinal radiation damage in mice," Science, vol. 293, No. 5528, pp. 293-297 (2001).
Rotolo et al., "Anti-ceramide antibody prevents the radiation gastrointestinal syndrome in mice," Journal of Clinical Investigation, vol. 122, No. 5, pp. 1786-1790 (May 1, 2012).
Rotolo et al., JBC, 280, pp. 26425-26434 (2005).
Stage et al., "Depression in COPD—management and quality of life","International Journal of Chronic Obstructive Pulmonary Disease", vol. 1, No. 3, pp. 315-320 (2006).
Vielhaber et al., "Mouse anti-ceramide antiserum: a specific tool for the detection of endogenous ceramide," Glycobiology, vol. 11, No. 6, pp. 451-457 (2001).

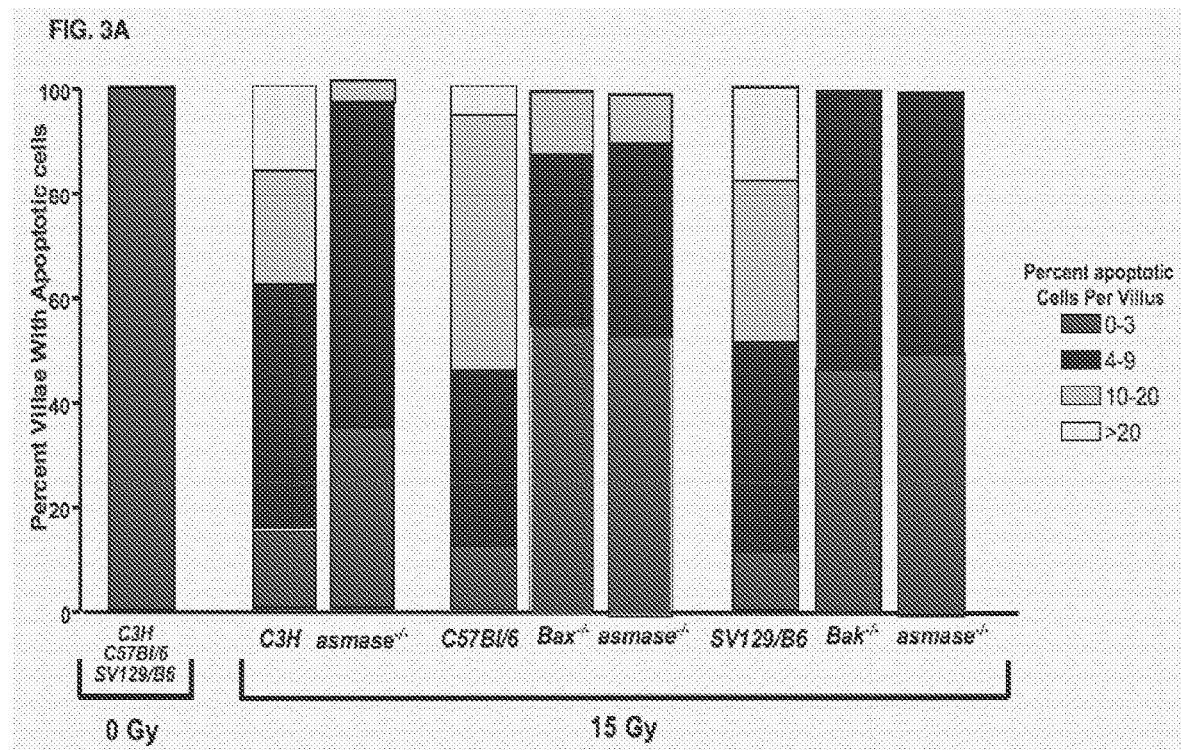
FIG. 3B
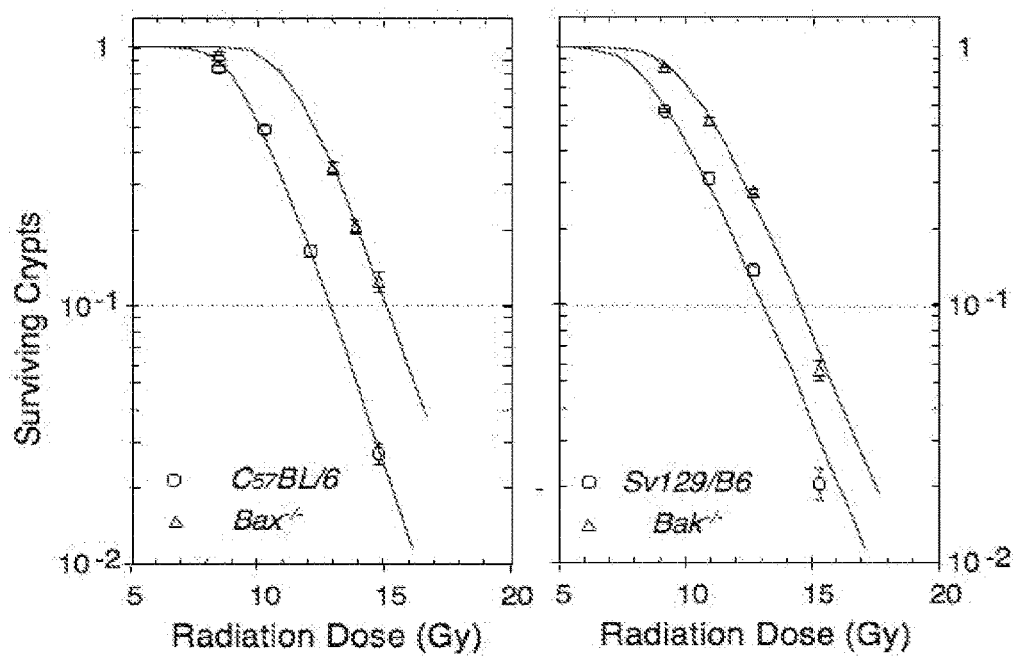

α-ceramide    IgM

2A2 ANTIBODY ATTENUATES RADIATION-INDUCED GI DEATH *IN VIVO*, RECAPITULATING THE *ASMASE$^{-/-}$* PHENOTYPE. NECROPSY RESULTS.

|            | Survival (%) | GI Death | BM Death |
|------------|--------------|----------|----------|
| 14 Gy      | 50%          | 2/2      | 0/2      |
| 14 Gy + 2A2 | 100%        | -        | -        |
| 15 Gy      | 0%           | 10/10    | 0/10     |
| 15 Gy + 2A2 | 70%         | 0/3      | 3/3      |
| 16 Gy      | 0%           | 5/5      | 0/5      |
| 16 Gy + 2A2 | 60%         | 1/3      | 2/3      |
| 17 Gy      | 0%           | 4/4      | 0/4      |
| 17 Gy + 2A2 | 25%         | 2/3      | 1/3      |

FIG. 15
FIG. 15A
FIG. 15B
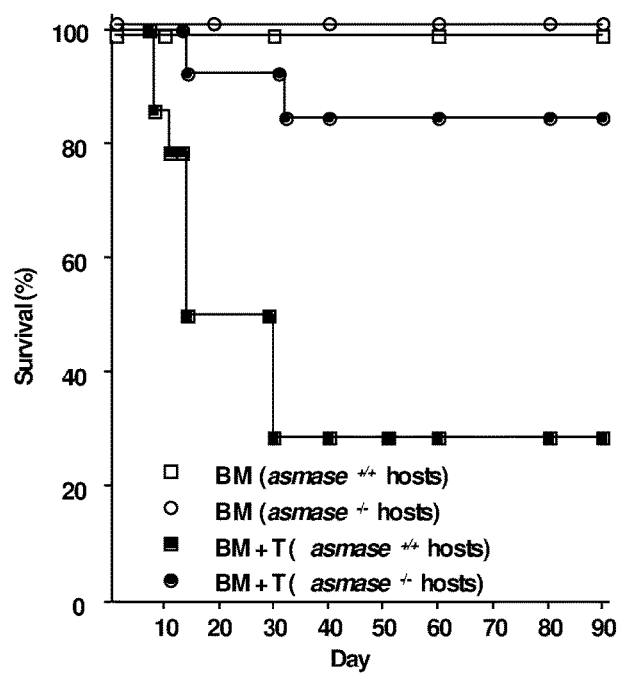
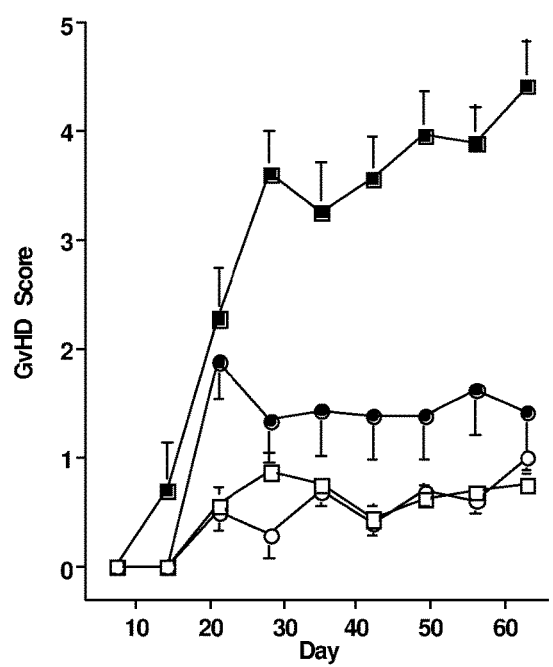

*asmase*[+/+] Hepatocyte + Effector T cells

*asmase*[-/-] Hepatocyte + Effector T cells

FIG. 22A
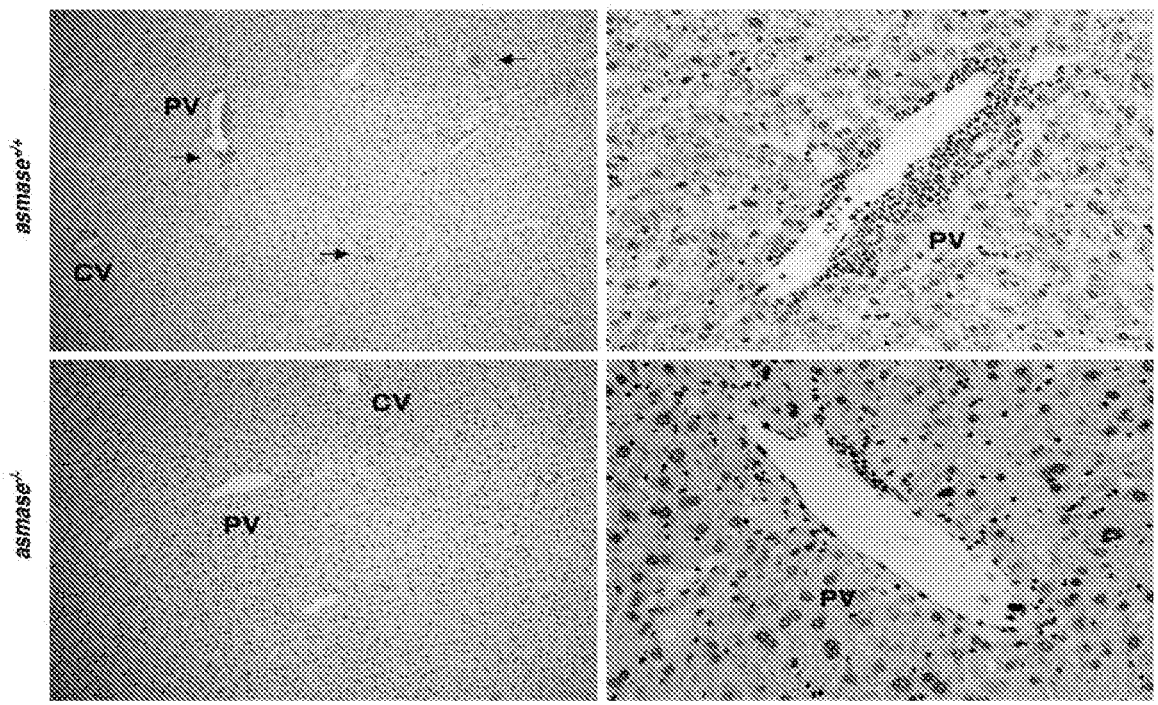
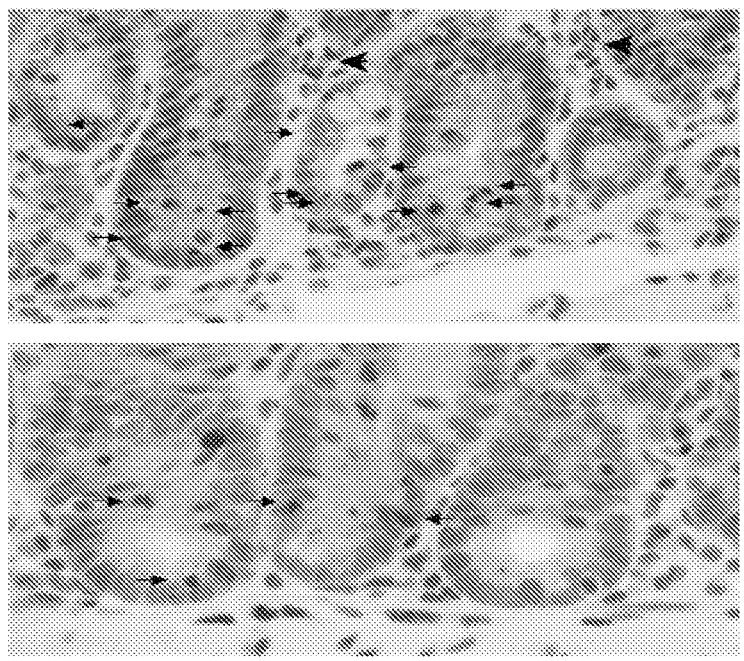
FIG. 22B

FIG. 23A
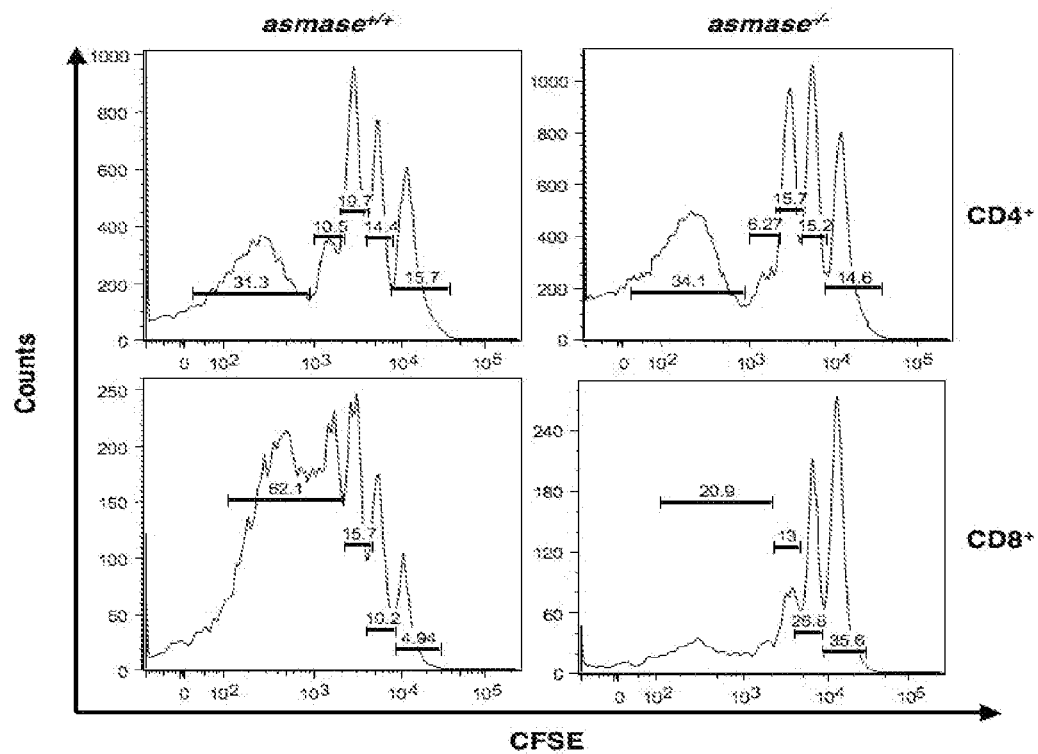
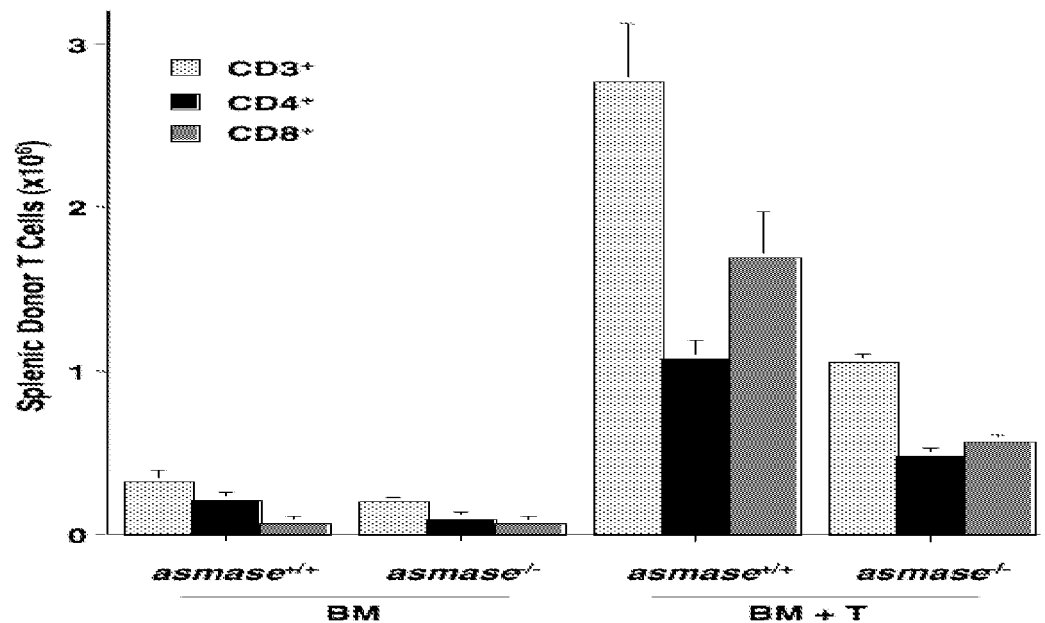
FIG. 23B

SEQUENCE LISTING

```
<160> NUMBER OF SEQ ID NOS: 9

<210> SEQ ID NO 1
<211> LENGTH: 631
<212> TYPE: PRT
<213> ORGANISM: Homo sapiens

<400> SEQUENCE: 1

Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
            20                  25                  30

Met Gly Leu Val Leu Ala Leu Ala Leu Ala Leu Ala Leu Ala
        35                  40                  45

Leu Ser Asp Ser Arg Val Leu Trp Ala Pro Ala Glu Ala His Pro Leu
```

```
            50                  55                  60
Ser Pro Gln Gly His Pro Ala Arg Leu His Arg Ile Val Pro Arg Leu
 65                  70                  75                  80

Arg Asp Val Phe Gly Trp Gly Asn Leu Thr Cys Pro Ile Cys Lys Gly
                 85                  90                  95

Leu Phe Thr Ala Ile Asn Leu Gly Leu Lys Lys Glu Pro Asn Val Ala
                100                 105                 110

Arg Val Gly Ser Val Ala Ile Lys Leu Cys Asn Leu Leu Lys Ile Ala
                115                 120                 125

Pro Pro Ala Val Cys Gln Ser Ile Val His Leu Phe Glu Asp Asp Met
130                 135                 140

Val Glu Val Trp Arg Arg Ser Val Leu Ser Pro Ser Glu Ala Cys Gly
145                 150                 155                 160

Leu Leu Leu Gly Ser Thr Cys Gly His Trp Asp Ile Phe Ser Ser Trp
                165                 170                 175

Asn Ile Ser Leu Pro Thr Val Pro Lys Pro Pro Lys Pro Pro Ser
                180                 185                 190

Pro Pro Ala Pro Gly Ala Pro Val Ser Arg Ile Leu Phe Leu Thr Asp
                195                 200                 205

Leu His Trp Asp His Asp Tyr Leu Glu Gly Thr Asp Pro Asp Cys Ala
210                 215                 220

Asp Pro Leu Cys Cys Arg Arg Gly Ser Gly Leu Pro Pro Ala Ser Arg
225                 230                 235                 240

Pro Gly Ala Gly Tyr Trp Gly Glu Tyr Ser Lys Cys Asp Leu Pro Leu
                245                 250                 255

Arg Thr Leu Glu Ser Leu Leu Ser Gly Leu Gly Pro Ala Gly Pro Phe
                260                 265                 270

Asp Met Val Tyr Trp Thr Gly Asp Ile Pro Ala His Asp Val Trp His
                275                 280                 285

Gln Thr Arg Gln Asp Gln Leu Arg Ala Leu Thr Thr Val Thr Ala Leu
290                 295                 300

Val Arg Lys Phe Leu Gly Pro Val Pro Val Tyr Pro Ala Val Gly Asn
305                 310                 315                 320

His Glu Ser Thr Pro Val Asn Ser Phe Pro Pro Phe Ile Glu Gly
                325                 330                 335

Asn His Ser Ser Arg Trp Leu Tyr Glu Ala Met Ala Lys Ala Trp Glu
                340                 345                 350

Pro Trp Leu Pro Ala Glu Ala Leu Arg Thr Leu Arg Ile Gly Gly Phe
                355                 360                 365

Tyr Ala Leu Ser Pro Tyr Pro Gly Leu Arg Leu Ile Ser Leu Asn Met
                370                 375                 380

Asn Phe Cys Ser Arg Glu Asn Phe Trp Leu Leu Ile Asn Ser Thr Asp
385                 390                 395                 400

Pro Ala Gly Gln Leu Gln Trp Leu Val Gly Glu Leu Gln Ala Ala Glu
                405                 410                 415

Asp Arg Gly Asp Lys Val His Ile Ile Gly His Ile Pro Pro Gly His
                420                 425                 430

Cys Leu Lys Ser Trp Ser Trp Asn Tyr Tyr Arg Ile Val Ala Arg Tyr
                435                 440                 445

Glu Asn Thr Leu Ala Ala Gln Phe Phe Gly His Thr His Val Asp Glu
                450                 455                 460

Phe Glu Val Phe Tyr Asp Glu Glu Thr Leu Ser Arg Pro Leu Ala Val
465                 470                 475                 480
```

```
Ala Phe Leu Ala Pro Ser Ala Thr Thr Tyr Ile Gly Leu Asn Pro Gly
            485                 490                 495

Tyr Arg Val Tyr Gln Ile Asp Gly Asn Tyr Ser Gly Ser Ser His Val
        500                 505                 510

Val Leu Asp His Glu Thr Tyr Ile Leu Asn Leu Thr Gln Ala Asn Ile
    515                 520                 525

Pro Gly Ala Ile Pro His Trp Gln Leu Leu Tyr Arg Ala Arg Glu Thr
530                 535                 540

Tyr Gly Leu Pro Asn Thr Leu Pro Thr Ala Trp His Asn Leu Val Tyr
545                 550                 555                 560

Arg Met Arg Gly Asp Met Gln Leu Phe Gln Thr Phe Trp Phe Leu Tyr
                565                 570                 575

His Lys Gly His Pro Ser Glu Pro Cys Gly Thr Pro Cys Arg Leu
            580                 585                 590

Ala Thr Leu Cys Ala Gln Leu Ser Ala Arg Ala Asp Ser Pro Ala Leu
            595                 600                 605

Cys Arg His Leu Met Pro Asp Gly Ser Leu Pro Glu Ala Gln Ser Leu
            610                 615                 620

Trp Pro Arg Pro Leu Phe Cys
625                 630

<210> SEQ ID NO 2
<211> LENGTH: 2473
<212> TYPE: DNA
<213> ORGANISM: Homo sapiens

<400> SEQUENCE: 2
```

| | | | | |
|---|---|---|---|---|
| atcagaggaa gaggaagggg cggagctgct ttgcggccgg ccgcggagca gtcagccgac | 60 |
| tacagagaag ggtaatcggg tgtccccggc gccgcccggg gccctgaggg ctggctaggg | 120 |
| tccaggccgg gggggacggg acagacgaac cagccccgtg taggaagcgc gacaatgccc | 180 |
| cgctacggag cgtcactccg ccagagctgc cccaggtccg gccgggagca gggacaagac | 240 |
| gggaccgccg gagcccccgg actcctttgg atgggcctgg tgctggcgct ggcgctggcg | 300 |
| ctggcgctgg cgctggctct gtctgactct cgggttctct gggctccggc agaggctcac | 360 |
| cctctttctc cccaaggcca tcctgccagg ttacatcgca tagtgccccg gctccgagat | 420 |
| gtctttgggt gggggaacct cacctgccca atctgcaaag gtctattcac cgccatcaac | 480 |
| ctcgggctga gaaggaacc caatgtggct cgcgtgggct ccgtggccat caagctgtgc | 540 |
| aatctgctga agatagcacc acctgccgtg tgccaatcca ttgtccacct ctttgaggat | 600 |
| gacatggtgg aggtgtggag acgctcagtg ctgagcccat ctgaggcctg tggcctgctc | 660 |
| ctgggctcca cctgtgggca ctgggacatt ttctcatctt ggaacatctc tttgcctact | 720 |
| gtgccgaagc cgcccccaa acccctagc ccccagccc caggtgcccc tgtcagccgc | 780 |
| atcctcttcc tcactgacct gcactgggat catgactacc tggagggcac ggaccctgac | 840 |
| tgtgcagacc cactgtgctg ccgccggggt tctggcctgc cgcccgcatc ccggccaggt | 900 |
| gccggatact ggggcgaata cagcaagtgt gacctgcccc tgaggaccct ggagagcctg | 960 |
| ttgagtgggc tgggcccagc cggcctttt gatatggtgt actggacagg agacatcccc | 1020 |
| gcacatgatg tctggcacca gactcgtcag gaccaactgc gggccctgac caccgtcaca | 1080 |
| gcacttgtga ggaagttcct ggggccagtc cagtgtacc ctgctgtggg taaccatgaa | 1140 |
| agcacacctg tcaatagctt ccctcccccc ttcattgagg gcaaccactc ctcccgctgg | 1200 |

-continued

```
ctctatgaag cgatggccaa ggcttgggag ccctggctgc ctgccgaagc cctgcgcacc    1260
ctcagaattg gggggttcta tgctctttcc ccatacccg gtctccgcct catctctctc     1320
aatatgaatt tttgttcccg tgagaacttc tggctcttga tcaactccac ggatcccgca    1380
ggacagctcc agtggctggt gggggagctt caggctgctg aggatcgagg agacaaagtg    1440
catataattg ccacattcc cccagggcac tgtctgaaga gctggagctg gaattattac     1500
cgaattgtag ccaggtatga gaacaccctg gctgctcagt tctttggcca cactcatgtg    1560
gatgaatttg aggtcttcta tgatgaagag actctgagcc ggccgctggc tgtagccttc    1620
ctggcaccca gtgcaactac ctacatcggc cttaatcctg gttaccgtgt gtaccaaata    1680
gatggaaact actccgggag ctctcacgtg gtcctggacc atgagaccta catcctgaat    1740
ctgacccagg caaacatacc gggagccata ccgcactggc agcttctcta cagggctcga    1800
gaaacctatg gctgcccaa cacactgcct accgcctggc acaacctggt atatcgcatg     1860
cggggcgaca tgcaacttt ccagaccttc tggtttctct accataaggg ccacccaccc     1920
tcggagccct gtggcacgcc ctgccgtctg gctactcttt gtgcccagct ctctgcccgt    1980
gctgacagcc ctgctctgtg ccgccacctg atgccagatg ggagcctccc agaggcccag    2040
agcctgtggc caaggccact gttttgctag gccccaggg cccacatttg gaaagttct      2100 tgatgtagga aagggtgaaa agcccaaat gctgctgtgg ttcaaccagg caagatcatc     2160
cggtgaaaga accagtccct gggccccaag gatgccgggg aaacaggacc ttctcctttc    2220
ctggagctgg tttagctgga tatgggaggg ggtttggctg cctgtgccca ggagctagac    2280
tgccttgagg ctgctgtcct ttcacagcca tggagtagag gcctaagttg acactgccct    2340
gggcagacaa gacaggagct gtcgccccag gcctgtgctg cccagccagg aaccctgtac    2400
tgctgctgcg acctgatgct gccagtctgt taaaataaag ataagagact tggactccaa    2460
aaaaaaaaaa aaa                                                       2473
```

```
<210> SEQ ID NO 3
<211> LENGTH: 192
<212> TYPE: PRT
<213> ORGANISM: Homo sapiens

<400> SEQUENCE: 3

Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Phe Ile Gln
                20                  25                  30

Asp Arg Ala Gly Arg Met Gly Glu Ala Pro Glu Leu Ala Leu Asp
            35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
                100                 105                 110

Leu Phe Tyr Phe Ala Ser Lys Leu Val Leu Lys Ala Leu Cys Thr Lys
            115                 120                 125

Val Pro Glu Leu Ile Arg Thr Ile Met Gly Trp Thr Leu Asp Phe Leu
    130                 135                 140
```

```
Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 4
<211> LENGTH: 888
<212> TYPE: DNA
<213> ORGANISM: Homo sapiens

<400> SEQUENCE: 4
tcacgtgacc cgggcgcgct gcggccgccc gcgcggaccc ggcgagaggc ggcggcggga    60
gcggcggtga tggacgggtc cggggagcag cccagaggcg gggggcccac cagctctgag   120
cagatcatga agacaggggc ccttttgctt cagggtttca tccaggatcg agcagggcga   180
atgggggggg aggcacccga gctggccctg accccggtgc ctcaggatgc gtccaccaag   240
aagctgagcg agtgtctcaa cgcatcgggg acgaactgg acagtaacat ggagctgcag   300
aggatgattg ccgccgtgga cacagactcc ccccgagagg tcttttttccg agtggcagct   360 gacatgtttt ctgacggcaa cttcaactgg ggccgggttg tcgcccttttt ctactttgcc   420 agcaaactgg tgctcaaggc cctgtgcacc aaggtgccgg aactgatcag aaccatcatg   480
ggctggacat tggacttcct ccgggagcgg ctgttgggct ggatccaaga ccagggtggt   540
tgggacggcc tcctctccta ctttgggacg cccacgtggc agaccgtgac catctttgtg   600
gcgggagtgc tcaccgcctc actcaccatc tggaagaaga tgggctgagg ccccccagctg   660 ccttggactg tgttttttcct ccataaaatta tggcattttt ctggggaggg tggggattgg   720
gggacgtggg cattttttctt acttttgtaa ttattggggg gtgtggggaa gagtggtctt   780 gaggggggtaa taaacctcct tcgggacaca aaaaaaaaa aaaaaaaaaa aaaaaaaaa    840 aaaaaaaaaa aaaaaaaaaa aaaaaaaaaa aaaaaaaaaa aaaaaaaa                888

<210> SEQ ID NO 5
<211> LENGTH: 211
<212> TYPE: PRT
<213> ORGANISM: Homo sapiens

<400> SEQUENCE: 5

Met Ala Ser Gly Gln Gly Pro Gly Pro Pro Arg Gln Glu Cys Gly Glu
1               5                   10                  15

Pro Ala Leu Pro Ser Ala Ser Glu Glu Gln Val Ala Gln Asp Thr Glu
                20                  25                  30

Glu Val Phe Arg Ser Tyr Val Phe Tyr Arg His Gln Gln Glu Gln Glu
            35                  40                  45

Ala Glu Gly Val Ala Ala Pro Ala Asp Pro Glu Met Val Thr Leu Pro
        50                  55                  60

Leu Gln Pro Ser Ser Thr Met Gly Gln Val Gly Arg Gln Leu Ala Ile
65                  70                  75                  80

Ile Gly Asp Asp Ile Asn Arg Arg Tyr Asp Ser Glu Phe Gln Thr Met
                85                  90                  95

Leu Gln His Leu Gln Pro Thr Ala Glu Asn Ala Tyr Glu Tyr Phe Thr
            100                 105                 110

Lys Ile Ala Thr Ser Leu Phe Glu Ser Gly Ile Asn Trp Gly Arg Val
        115                 120                 125
```

-continued

```
Val Ala Leu Leu Gly Phe Gly Tyr Arg Leu Ala Leu His Val Tyr Gln
            130                 135                 140

His Gly Leu Thr Gly Phe Leu Gly Gln Val Thr Arg Phe Val Val Asp
145                 150                 155                 160

Phe Met Leu His His Cys Ile Ala Arg Trp Ile Ala Gln Arg Gly Gly
                165                 170                 175

Trp Val Ala Ala Leu Asn Leu Gly Asn Gly Pro Ile Leu Asn Val Leu
            180                 185                 190

Val Val Leu Gly Val Val Leu Leu Gly Gln Phe Val Val Arg Arg Phe
            195                 200                 205

Phe Lys Ser
    210

<210> SEQ ID NO 6
<211> LENGTH: 2203
<212> TYPE: DNA
<213> ORGANISM: Homo sapiens

<400> SEQUENCE: 6
gtctgcatcc ggtggccaca gagcaacttc ctctagaggg agctgattgg agccgggtgc      60
cgctggcacc tctatgatca ctggagtctc gcgggtccct cgggctgcac agggacaagt     120
aaaggctaca tccagatgcc gggaatgcac tgacgcccat tcctggaaac tgggctccca     180
ctcagcccct gggagcagca gccgccagcc cctcggacc tccatctcca ccctgctgag      240
ccacccgggt tgggccagga tcccggcagg ctgatcccgt cctccactga gacctgaaaa     300
atggcttcgg ggcaaggccc aggtcctccc aggcaggagt gcggagagcc tgccctgccc     360
tctgcttctg aggagcaggt agcccaggac acagaggagg ttttccgcag ctacgttttt     420
taccgccatc agcaggaaca ggaggctgaa ggggtggctg cccctgccga cccagagatg     480
gtcaccttac tctgcaacc tagcagcacc atggggcagg tgggacggca gctcgccatc     540 atcgggacg acatcaaccg acgctatgac tcagagttcc agaccatgtt gcagcacctg     600
cagcccacgg cagagaatgc ctatgagtac ttcaccaaga ttgccaccag cctgtttgag     660
agtggcatca attggggccg tgtggtggct cttctgggct cggctaccg tctgccccta     720 cacgtctacc agcatggcct gactggcttc ctaggccagg tgacccgctt cgtggtcgac     780
ttcatgctgc atcactgcat tgcccggtgg attgcacaga ggggtggctg ggtggcagcc     840
ctgaacttgg gcaatggtcc catcctgaac gtgctggtgg ttctgggtgt ggttctgttg     900
ggccagtttg tggtacgaag attcttcaaa tcatgactcc caagggtgcc ctttgggggtc    960 ccggttcaga cccctgcctg gacttaagcg aagtctttgc cttctctgtt cccttgcagg    1020
ggtcccccct caagagtaca gaagctttag caagtgtgca ctccagcttc ggagggcccc    1080
tgcgtggggg ccagtcaggc tgcagaggca cctcaacatt gcatggtgct agtgggccct    1140
ctctctgggc ccaggggctg tggccgtctc ctccctcagc tctctgggac tccttagcc     1200 ctgtctgcta ggcgctgggg agactgataa cttggggagg caagagactg ggagccactt    1260
ctccccagaa agtgtttaac ggttttagct ttttataata cccttgtgag agcccattcc    1320
caccattcta cctgaggcca ggacgtctgg ggtgtgggga ttggtgggtc tatgttcccc    1380
aggattcagc tattctggaa gatcagcacc ctaagagatg ggactaggac ctgagcctgg    1440
tcctggccgt ccctaagcat gtgtcccagg agcaggacct actaggagag gggggccaag    1500
gtcctgctca actctacccc tgctcccatt cctccctccg gccatactgc ctttgcagtt    1560
ggactctcag ggattctggg cttggggtgt ggggtggggt ggagtcgcag accagagctg    1620
```

| | |
|---|---|
| tctgaactca cgtgtcagaa gcctccaagc ctgcctccca aggtcctctc agttctctcc | 1680 |
| cttcctctct ccttatagac acttgctccc aacccattca ctacaggtga aggctctcac | 1740 |
| ccccatccct gggggccttg ggtgagtggc ctgctaaggc tcctccttgc ccagactaca | 1800 |
| gggcttagga cttggtttgt tatatcaggg aaaaggagta gggagttcat ctggagggtt | 1860 |
| ctaagtggga gaaggactat caacaccact aggaatccca gaggtgggat cctccctcat | 1920 |
| ggctctggca cagtgtaatc caggggtgta gatgggggaa ctgtgaatac ttgaactctg | 1980 |
| ttcccccacc ctccatgctc ctcacctgtc taggtctcct cagggtgggg ggtgacagtg | 2040 |
| ccttctctat tgggcacagc ctagggtctt ggggtcagg ggggagaagt tcttgattca | 2100 |
| gccaaatgca gggaggggag gcagatggag cccataggcc accccctatc ctctgagtgt | 2160 |
| ttggaaataa actgtgcaat cccctcaccc tgaaaaaaaa aaa | 2203 |

<210> SEQ ID NO 7
<211> LENGTH: 4572
<212> TYPE: DNA
<213> ORGANISM: Homo sapiens

<400> SEQUENCE: 7

| | |
|---|---|
| atcagaggaa gaggaagggg cggagctgct ttgcggccgg ccgcggagca gtcagccgac | 60 |
| tacagagaag ggtaatcggg tgtccccggc gccgccggg gccctgaggg ctggctaggg | 120 |
| tccaggccgg gggggacggg acagacgaac cagccccgtg taggaagcgc gacaatgccc | 180 |
| cgctacggag cgtcactccg ccagagctgc cccaggtccg gccgggagca gggacaagac | 240 |
| gggaccgccg gagccccgg actcctttgg atgggcctgg tgctggcgct ggcgctggcg | 300 |
| ctggcgctgg cgctggctct gtctgactct cgggttctct gggctccggc agaggctcac | 360 |
| cctcttctc cccaaggcca tcctgccagg ttacatcgca tagtgccccg gctccgagat | 420 |
| gtctttgggt gggggaacct cacctgccca atctgcaaag gtctattcac cgccatcaac | 480 |
| ctcgggctga aggtgagcac tgaaggggct gcagtggagg aggccgaaag gagtgctggg | 540 |
| gctgggggct ggggctgatg ctggtgcgct gggctcagaa tgcatccctg atggagaggg | 600 |
| tggcatctac aatccatcac tgagtttgct cccctttggg acacccatg gctacatgcc | 660 |
| accatcaccc cattgtgacc tttgtgaagt aagaaaataa tgcagacagt gcctgaggaa | 720 |
| gtcagcttgc caagcaaagg cctcatgcca caggccgctg agctaaagaa gaagcgatgg | 780 |
| cctggtgctg cctgagttac agggcaatat ctggaaggca aggtgtgca ctgagcttgg | 840 |
| tgcactgagt cctgcccagc ccagtttgg aaatggaggc caaggggtg gtggccaggg | 900 |
| gttggcctgg ttcctctgct ctgcctctga tttctcacca tgcgctcctc ccactgcaga | 960 |
| aggaacccaa tgtggctcgc gtgggctccg tggccatcaa gctgtgcaat ctgctgaaga | 1020 |
| tagcaccacc tgccgtgtgc caatccattg tccacctctt tgaggatgac atggtggagg | 1080 |
| tgtggagacg ctcagtgctg agcccatctg aggcctgtgg cctgctcctg ggctccacct | 1140 |
| gtgggcactg ggacattttc tcatcttgga acatctcttt gcctactgtg ccgaagccgc | 1200 |
| cccccaaacc ccctagcccc ccagcccag gtgcccctgt cagccgcatc ctcttcctca | 1260 |
| ctgacctgca ctgggatcat gactacctgg agggcacgga ccctgactgt gcagaccac | 1320 |
| tgtgctgccg ccggggttct ggcctgccgc ccgcatcccg gccaggtgcc ggatactggg | 1380 |
| gcgaatacag caagtgtgac ctgccccctga ggacccctgga gagcctgttg agtgggctgg | 1440 |
| gcccagccgg ccctttttgat atggtgtact ggacaggaga catccccgca catgatgtct | 1500 |

```
ggcaccagac tcgtcaggac caactgcggg ccctgaccac cgtcacagca cttgtgagga    1560
agttcctggg gccagtgcca gtgtaccctg ctgtgggtaa ccatgaaagc acacctgtca    1620
atagcttccc tcccccttc attgagggca accactcctc ccgctggctc tatgaagcga    1680
tggccaaggc ttgggagccc tggctgcctg ccgaagccct cgcaccctc aggtacttat     1740 cgtccgtgga aacccaggaa gggaaaagaa aggtgaatga aagtgaaggg agaagggaac    1800
ctggggcatt gtctctgatt gctctagcat gagtccttag tgctcttcat ttggctcccc    1860
taatctgact cctccttccc tttctactgt tttgccgcac caggcttttt tttttttttt    1920 tttttagtt tagtttttgt agagacaaga tcttgctatg ttgcccaggc tggtctcaaa     1980
cacctaacct caagcaatcc tcccgcctcg gcctcccaaa atgctgggac cacaggcatc    2040
agctactgct cctggccctc ccttttttt tttttttt tttttttt tgagatggaa         2100 tcttgctctg ttgcccaggc tggagtgcag tggcaccatc tcagctcact acagcctcca    2160
cctcctgggt tcaagcaatt ctgcctcagc ctcccaagta cctgggacta caggtgcacg    2220
ccaccacacc cagctaattt ttgtattttt agtagagatg gggtttcacc atgttggcca    2280
agatggtctt gatctcctga cctcatgatc tgcccacctc ggcctcccaa agtgctggga    2340
ttacaggcat gaaccactgc acccagcttt ccagccctcc ctttctactc ttatctccag    2400
ccaccctcct tcaaaggtct ggcagcataa cctctctatg ccccagctgt gtctttgctc    2460
atgttggccc tctggaaatg atttccccct ttttttaag tgctccagtt tttcccacct    2520
tatccatccc atgtcatctt ccctctgtgt ggtccttgct tcccattcta gctaactctt    2580
atccctcccc catactcctg gagccctctg ccctcagagt cttttgtgtc acacagaccc    2640
aataattaga actgtttggt ctctggctag actgtgagct ccttgcaggt ggggaagatg    2700
tcatgtatgc ttttacccctc cacccaaatg cccagcacag gaggaccagg attggaacaa    2760
gtgttgacct ctcatgttta ctttgtttca gaattggggg gttctatgct cttcccat      2820 accccggtct ccgcctcatc tctctcaata tgaattttg ttcccgtgag aacttctggc     2880
tcttgatcaa ctccacggat cccgcaggac agctccagtg gctggtgggg gagcttcagg    2940
ctgctgagga tcgaggagac aaagtgaggg ccagtagtgg gaacacgtg gtgctggggg     3000 acaagcaggc tcctgttgag ctggagcacc tctgggcaca gaagttttat tttcctggca    3060
ttcccaacaa gtgttccctg gggattcagc tcatggtcac tgttgaaagc cttcattcag    3120 tcccccttc tctagccagg gctgcctgga ccctggatg ccctgattac catccttaat      3180
tctccctact aggtgcatat aattggccac attcccccag gcactgtct gaagagctgg     3240 agctggaatt attaccgaat tgtagccagg taggacggag atgagggtgg gaatagggac    3300
agggtgagtg tctgaaggct gaaaattccc ttgagcatct caccatccct gttgtcccat    3360
ggagtgggga ggctcctcac tagaacaggt tggagaaaga gggcatccta tctccccaga    3420
tgtcttccta cccctcccta gaatcttctg aatgtagtac cttctggcca ggtatgagaa    3480
caccctggct gctcagttct ttggccacac tcatgtggat gaatttgagg tcttctatga    3540
tgaagagact ctgagccggc cgctggctgt agccttcctg gcacccagtg caactaccta    3600
catcggcctt aatcctggtg agtgaggcag aagggagcct cccttatcct ggagttggtg    3660 ggataggga aggaggttgg agccagagcc tgcaaagcat gggcaggatg tgtggcccct    3720
ccctggagtt acccttgctc cttgcccctc cagtcagccc cacatccttg caggttaccg    3780
tgtgtaccaa atagatggaa actactccgg gagctctcac gtggtcctgg accatgagac    3840
ctacatcctg aatctgaccc aggcaaacat accgggagcc ataccgcact ggcagcttct    3900
```

| | | | |
|---|---|---|---|
| ctacagggct | cgagaaacct | atgggctgcc | caacacactg cctaccgcct ggcacaacct | 3960 |
| ggtatatcgc | atgcggggcg | acatgcaact | tttccagacc ttctggtttc tctaccataa | 4020 |
| gggccaccca | ccctcggagc | cctgtggcac | gccctgccgt ctggctactc tttgtgccca | 4080 |
| gctctctgcc | cgtgctgaca | gccctgctct | gtgccgccac ctgatgccag atgggagcct | 4140 |
| cccagagggcc | cagagcctgt | ggccaaggcc | actgttttgc tagggcccca gggcccacat | 4200 |
| ttgggaaagt | tcttgatgta | ggaaagggtg | aaaaagccca aatgctgctg tggttcaacc | 4260 |
| aggcaagatc | atccggtgaa | agaaccagtc | cctgggcccc aaggatgccg gggaaacagg | 4320 |
| accttctcct | ttcctggagc | tggtttagct | ggatatggga gggggtttgg ctgcctgtgc | 4380 |
| ccaggagcta | gactgccttg | aggctgctgt | cctttcacag ccatggagta gaggcctaag | 4440 |
| ttgacactgc | cctgggcaga | caagacagga | gctgtcgccc caggcctgtg ctgcccagcc | 4500 |
| aggaaccctg | tactgctgct | gcgacctgat | gctgccagtc tgttaaaata aagataagag | 4560 |
| acttggactc | ca | | | 4572 |

<210> SEQ ID NO 8
<211> LENGTH: 6939
<212> TYPE: DNA
<213> ORGANISM: Homo sapiens

<400> SEQUENCE: 8

| | | | |
|---|---|---|---|
| tcacgtgacc | cgggcgcgct | gcggccgccc | gcgcggaccc ggcgagaggc ggcggcggga | 60 |
| gcggcggtga | tggacgggtc | cggggagcag | cccagaggcg ggggtgaggc gggaggcaga | 120 |
| cgggcgggag | gagggcgagc | cccctcgccg | gcccgtccgg gatccttcct accggcctgg | 180 |
| ggctgtgcga | tctccaagca | ctgaggggca | gaaactcccg gatcgggcgc tgccagcctc | 240 |
| cagtcccctc | cgtcctcgga | ggttcctggc | tctctgatcc ccgtgtcccg atccctgcct | 300 |
| ctctggcgct | ctcggaccct | cgagaaccag | gggatctcgg aagccaagcc ccgggcagg | 360 |
| cccgggcttg | tcgcccgcac | cacttcctgc | ctctggcact ggtgggaggg gcgggtctcg | 420 |
| cctctgcccc | ctcaggccag | gggtctggat | gcatatagcg ttcccctagc ctctttcccc | 480 |
| ggggagaatg | taggatacag | gcccagcctc | ctggcctttc tccatcaggg actcagttgt | 540 |
| ctgggccccc | ccgtcacttt | atctgctagg | gtcccagaag tccagggtcc ccagctctgt | 600 |
| cctccctcag | gggccgtgag | tctccacagt | ctcctgatcc cctagaaccc aagagtccag | 660 |
| gtacctcttc | ccttcctttc | tcctctaggg | cccaccagct ctgagcagat catgaagaca | 720 |
| ggggcccttt | tgcttcaggg | gtgagtttga | ggtctgatta ttgtggcaca gatttgagga | 780 |
| gtgacacccc | gttctgattc | tgcaccctca | ctccatcccc actctagttt catccaggat | 840 |
| cgagcagggc | gaatgggggg | ggaggcaccc | gagctggccc tggacccggt gcctcaggat | 900 |
| gcgtccacca | agaagctgag | cgagtgtctc | aagcgcatcg gggacgaact ggacagtaac | 960 |
| atggagctgc | agaggtgtgg | gcccctgagg | acccagaagt ccagccactg ggctccttca | 1020 |
| ggacacagga | ctctcagccc | cgcattctcc | tcctccccta agaactagga gtctgggccc | 1080 |
| cacaactcag | cgcaaacatt | ccggactccc | agcctcctc tctgccagga tcttaaaacc | 1140 |
| ctccttcagg | gagtcatttt | tcccaccttc | ctaaatgtct gtcttgtccc cttcccttgt | 1200 |
| cccccgttgg | cctgttgctt | ttcatttcag | cctggcttgg ggctcagtct ccttatcttt | 1260 |
| agtgtgcggt | ggatgcggga | attttccacc | atcagcctga tgcctgctcc ccggcactgg | 1320 |
| ttctcctctc | tcctgcagga | tgattgccgc | cgtggacaca gactcccccc gagaggtctt | 1380 |

```
tttccgagtg gcagctgaca tgttttctga cggcaacttc aactggggcc gggttgtcgc   1440
ccttttctac tttgccagca aactggtgct caaggtgggc agctgcaggg cagtgagccc   1500
agggatgctc cccctcagat ctgtgaggac ctggggatcg tggtatcaac cccctgcagt   1560
ggcccagtga ccacagaggg catggagaga gatggctgtg cactgggtgt ctgctccttc   1620
ttttattcat tcaacaagca tttactggac ctgctatgtg ccaggcctat acctggcacc   1680
tgggacacag cactgtacaa agcaggctac atccctgctc tcagggagtt cacgtgcagg   1740
ggtgaagtaa agtgggcagt gtgatttagc agagtggtca ggaaagattt ctatttttt    1800
ttttttttt tttgagatgg agttttgctc ttgttgccca ggcttgagtg caatggcatg    1860
atcttggttc actgcaacct ctgcctccca ggttcaagcg attctcctgc ctcagcttcc   1920
tgagtagctg ggattatggg tgtgcaccat tatccctggc ttttttttt ttttttttt    1980
tttttgtatt tttagtagag acgggtttca ccatgttggt caggctggtc ttgaactcct   2040
gacctcaagt gatccacctg ccttggcctc ccaaagtgct gggattacag gcatgagcca   2100
ccgcaacaag ccaggaaaga cttctaaggg caggtgacat caaagagcag gtgacattaa   2160
agccaaagct agaatgataa gaagcatgca gtgatctata gtgatcgggg gaagaggca    2220
tctggtagag ggaacagcaa gtgcaaaggc cctgaggtag gaccaagcct catcttttga   2280
cagtagggag gaggccagtg ctgttggaac agagtgaact ggggagaggg tgggaaagga   2340
aggcacagtt gggcagggc agattgtgtg gagtttttcg ggctgctgga aagactttt    2400
cttttctttt tttttttttt tttttttttt tttgagacag agtctcactt tgttgcccag   2460
gctggagtgc aatggcgcca tctcggctca ctgcaacctc tgcctcccgg ttcaagtga    2520
ctctcatgct ttagcctccc aagtagctag aattacaggc acacaccacc atgcctggct   2580
agttttttgta ttttagtag agacggagtt tcgccatgtt ggccaggctg gtctcaaact   2640
cctggcctca agtgatccgc ccaccttggc ctcccaaagt gctgggatta caggcgtgaa   2700
ccactgcacc cagcctggaa agactttaac tttactctga gtgtgatggg agtgattggc   2760
tggttttaaa tacggaagcg acaagacctg atttataact ttaagagatt attctagcaa   2820
gtatagatgc cccttgactt gcaatggtgt tacatcctag taatcccatc ataaattgaa   2880
aataacataa gttgaaaatg cattcaatgc cccgataaac ccatagtaag gtcaaaattg   2940
taagtcaaac cgtcataagt tgggactgt ctgtatagca aaatgttaat tgtagaatct    3000
aattataggt ggcggctata tggcttttaa ctgtgaaatt cttttaactt ttcattatga   3060
agattctcat aagaaaatgt ggtggggtg tggtgaaat gctcctggct gttgttggcc     3120
aaaagagatc atgaggcaca agggcagaag cgaggatcct ggagaggtgg cacctgtcat   3180
agtcttgctg aaagatgaca agccctggtg gtagcagcag aggtgcgggg ggggcatttt   3240
tttttttaag aggtagggtc ttgctctgtt ggccaggctg gagtgcagta gtgatcatag   3300
ctcactgcag cctcaaaccg ctgggggtcaa gcagttctct cgcctcagtc tccagagtag   3360
ctgagactac aggagcatgc caccacgccc cactaactgt tgcattagtc ttttctata    3420
gagacggggt ctcgctatgt tgtccaggct ggtctccaac agggagggat atttcttttt   3480
ggaagatttt tttttttttt tttttttttt tttgatacag ggtctcgctc tgttaccaag   3540
gctggaatgc agtggcatga ccttggctca ctgcagtctc cacctcctgg gttcaagcaa   3600
ttctacctca gcctcctgag aagctgggat tacaggctct ccccaccaca ccagcaaatg   3660
ggagggatat tcctttcttt ctttcttttt tttttttcct gagacggagt ctctctcggt   3720
tgcacccagg ctggagtgca gtggcgcgat ctcagctcac tgcaacctcc acctcctggg   3780
```

```
tttaagcgat tctcttgcct cagtctcccg agtagcttgg gattacaggc gtccgccacc    3840
acacccagct aattttttgca tttttagtag agatgggggtt tcaccatgtt ggccaggctg   3900
gtctcgaact ccttacctca ggtgatccgc ctgcctcggt ctcccaaagt gctgggatta    3960
caggcgtgag ccaccgtgct cagctgagag ggatatttct tgatgtgttt tcaagattga    4020
gctgatgggg cctgaacgtc cgagatgagg ggaatagcag tgcaggtgat ggtggcacca    4080
cctacagagc ggggatgata aatagaagt ggccagataa aggctgcagg agaagtcttg     4140
ggagttggga gagcaggtcg gggtccatgg tcaggggttg atcttctctg gtccagaaaa    4200
gtcctctctg gctgggcgtg gtggctcacg cctgtaatcc cagcactttg ggaggccgag    4260
gcagggggat catgaggtca ggagatcgag accatcctgg ctaacatggt gaaaccccgt    4320
ctctactaaa aatacaaaaa attagccggg catggtggtg ggcacttgta gtcccagcta    4380
ctcgggaggc tgaggcagaa gaatggcgtg aactgggagg cggagtttgc agtgagctga    4440
gattgcacca ctgcactcca gcctggagcg acagagtgag actccgtctc aaaaaaaaaa    4500
aaaaaaaaaa aagaaaagtc ctctctgggg aagtgacatt tgccctgaga gctgaagggt    4560
aagaatttgc ttcgtcgagg cctgtttagg cggaaacagg agtacatgaa gaagtcccga    4620
ggcaggaaga atttgatggg aatttaaaaa attaaaaaaa aaaaaaaaa tggggctggg     4680 catggtggct cacacctgta atcccggcac tttgggaggc tgaggcatgc ggatcaccta    4740
aggccaggag tttgagacca gcctgaccaa catggtgaaa ccttgtctgc actaaaaatt    4800
caaaaaaaaa aaaaaaaata gcccggtgtg gtggcggatg cctgtaatac cagctgctta    4860
ggaggctcag gcaggaggat cacttaaatc tgggaggcgg aggttgcaat gagccgagac    4920
tgcactattg tactccagcc tgggcaacaa gatcaaaact ctatctcaaa aaaaaaaaa     4980 aaaattagcc aggcatgttg gcaggcacct gtaatcccaa ccctttggga ggctggggca    5040
ggagaattgc ttgaacccag aaggcaaagc tttcagtgag ccgagattgc gccactgcac    5100
tccatcctgg gtgtcagagc aagactccat cttaaaaaaa aaaaatggaa gcagctcagc    5160
gaggcacaaa acaggaagtg gaaaggtgga gtgaggtcag gccaaagcct gcacacaggg    5220
cttgtgggct gcactgtgcc ttcgggtctt catcctgagg gtactgggga gccacagaag    5280
gctcaggggt ggggcagttg agagtaacat tatcttgttt acaatttat ttttttttt    5340 tatttatttt ttgagacgga ttcttgctct attgtccagg ctggcgtgaa atggcgtgat    5400
ctgggctcac tgcaacctct gcctcctggg ttcaagcgat tcacctgcct cagcatccca    5460
aggagctggg attacaggtg cctgccacca cacccagcta attttttgtat ttatttattt    5520 tgagatggag ttttgctctt gttgcccagg ctggagtgca atggcgcaac ctcggctcac    5580
tgcaacctcc gcctccgggg ttcaagcaat tctcctgcct cagactccca agtagctggg    5640
attacaggca tgtgccacca cgcccggcta attttgtatt tttagtagag atggcattac    5700
tccgtattgg tcaggctggt cttgaactcc cgacctcaag tgatccgcct gccttggcct    5760
cccaaagtgc tgggattaca ggcatgagcc gccgcacctg gccatgttta caattttga     5820 agccgacttc aattgtgggt ggcagaaatc tttgagggga ggcaaagaat tgacaaagga    5880
ggtttggggc cactatctcc aggcagtggg gacaaggttc agtccctaac gcccactcca    5940
ctccccacag gcctgtgca ccaaggtgcc ggaactgatc agaaccatca tgggctggac    6000
attggacttc ctccgggagc ggctgttggg ctggatccaa gaccagggtg gttgggtgag    6060
actcctcaag cctcctcacc cccaccaccg cgccctcacc accgcccctg ccccaccgtc    6120
```

| | |
|---|---|
| cctgcccccc gccactcctc tgggaccctg ggccttctgg agcaggtcac agtggtgccc | 6180 |
| tctccccatc ttcagatcat cagatgtggt ctataatgcg ttttccttac gtgtctgatc | 6240 |
| aatccccgat tcatctaccc tgctgacctc ccagtgaccc ctgacctcac tgtgaccttg | 6300 |
| acttgattag tgccttctgc cctccctgga gcctccactg cctctggaat tgctcaagtt | 6360 |
| cattgatgac cctctgaccc tagctctttc cttttttttt ttttccccac tgagaagggg | 6420 |
| tctcgctatg ttgcccaggt tggtctcgaa ctcctggcct caagcgatcc tcccgcctca | 6480 |
| gcctctcaaa gtgctgggat tacaggtgtg agccaccatg cctggcctga gtccagctct | 6540 |
| ttaatgcccg ttcatctcag tcccctgccc gcaatcctgc cttctggcct cctccgtccc | 6600 |
| tgatcccgcc tctgcctgcc caggggctgc cctggccga gtcactgaag cgactgatgt | 6660 |
| ccctgtctcc aggacggcct cctctcctac tttgggacgc ccacgtggca gaccgtgacc | 6720 |
| atctttgtgg cgggagtgct caccgcctca ctcaccatct ggaagaagat gggctgaggc | 6780 |
| ccccagctgc cttggactgt gttttcctc cataaattat ggcattttc tgggagggt | 6840 |
| ggggattggg ggacgtgggc atttttctta cttttgtaat tattgggggg tgtggggaag | 6900 |
| agtggtcttg aggggtaat aaacctcctt cgggacaca | 6939 |

<210> SEQ ID NO 9
<211> LENGTH: 3000
<212> TYPE: DNA
<213> ORGANISM: Homo sapiens

<400> SEQUENCE: 9

| | |
|---|---|
| gtctgcatcc ggtggccaca gagcaacttc ctctagaggg agctgattgg agccgggtgc | 60 |
| cgctggcacc tctatgatca ctggagtctc gcgggtccct cgggctgcac agggacaagt | 120 |
| aaaggctaca tccagatgcc gggaatgcac tgacgcccat tcctggaaac tgggctccca | 180 |
| ctcagcccct gggagcagca gccgccagcc cctcgggacc tccatctcca ccctgctgag | 240 |
| ccacccgggt tgggccagga tcccggcagg taagctggaa gggtcttgtc catcctccca | 300 |
| gatctcagca gccccagccc cagggtgggg cagggagcct gccgggagcc gggtggggaa | 360 |
| ggggaagctc aaggcttccc tgggcaggtc tgccgccccg gctggggacc tgatcctgcc | 420 |
| atgcctgcct ctggctgccc ctcacagctt cccctcttgg cccagccctg gatgccggag | 480 |
| aactgtaaga actgggtcct ttaacagtct gggagatggg agtggaggtc agagccaagg | 540 |
| tcaagggcag agagagaact ttctcagcgc ttgctgctgc ccaacatccc tagactgggt | 600 |
| ccagggcctg gccaggcatg tatccctggg caacattcat cggggcccag caagcccagg | 660 |
| aagtcggggg tggctcccct caccgggaat ttaggccact tggatggggg aggcagagct | 720 |
| aggcctgagt cagcataggt tgctggcctt ggtgggtgtt ctgaggctct acctgctccc | 780 |
| ctcggaagcc tggggtgttg gtagagggag ttggaggtgc agtcagcatc ctccagccct | 840 |
| actgtcctgg gggtgccggg tcctggagac tggggaagaa ggaaggccat cttatgtaag | 900 |
| gagctacggg gggtgggagg caagcaaaac tcttttttt tgttttttga aatggagtct | 960 |
| cgctctgttg cccaggctgg agtgcagtgg cgcaatctcg gctgaccgca acctccgcct | 1020 |
| ccaaggttca gcgattctc ctgcctcagc ctcccgagta gctgggacta caggcgcacg | 1080 |
| ccaccatgcc cagctaattt ttgtattttt agtagagatg gggtttcatt atgttggcca | 1140 |
| agctggtctt gaacttctga cctcgtgggc cactatgccc ggctgcaaag ttctgtttta | 1200 |
| acaaggcctt gccctagag gtggaggaga ggaaggtctg ccttcaccct gtccctgtcc | 1260 |
| ggcagatcga ggaggagtgg ggagctgggt gagggcacag gtggtccagc cctcctccac | 1320 |

```
cccttcttga gagctcttgg ggcactttcg aaaacactcc caggcctagc ggaaggaggg      1380
tgggcgaagg tccccaggcc ctgggcggtg ggggtggggc tgtgtgcttg cccagggtg      1440
gggctgcaca cccctccct ctgggatagg aggagggcgc tctccttctg agggctggag      1500
gctgcctggg gaaatggggc tctgggaggg gtgcaaactg aaagtgaaac agctgacatc    1560
caggaaacac tcgccctgat gaggggtcac agcaggttgg ggctgcggtc aggaccaggc    1620
aaagaggaaa attggggccg gggacagaag accaggtgtg tggtgggagt acgaggcagg    1680
ttatggggct tcaaagaagg ccctgatcct gagggctccc tccggtcact gcaaggcagc    1740
agtggggaag gcacagacag gaggtaaata gggaaagttg ccctgagaaa gaacacactc    1800
tgaggtccac aaactggaaa agaaatcttg catgcgtgtt gagtacatgg actcacggag    1860
attcagacaa acaacctgac tttccgtgac taacgatgtg acctcgggca ctcaactctt    1920
tgtgcctcac ttttcctgcc tgtaaagtgg gtatgatggc gctcaccctg ctgggttcat    1980
gtgagtttcc agtgttcacc acccacagag tgctcctaag tgggagagta tatcttaggc    2040
tctcaggaaa tgtttgcggc taacagccca gagttaaaaa acaggtgtgt tctggccagc    2100
cagagggaag tagggcctct gaggacagcc ttcatgggcc attggctggg cagtggctcg    2160
cttgcaataa gcatgtgctg ggtgggctgc aggaggcccc aggaacagct aaaaaccccc    2220
caggctcttg ccccaggagt ggcatgaact tgagagccag cgggcactgc tgcagccaca    2280
ccctcctcga tggtgcagat acctcagtct gcccttggct gcctcacctt cttaccctgt    2340
ctccctcaaa gagggagtgt tcagtaagtt gtttcctccc agcagacttc actgggaccc    2400
atgctggagt aagaataaaa agtcccagag gaggccaggc acggtggctc acacctgtaa    2460
tcccagcact gtggatggcc gaggcagact cacgaggtca ggagtttgag accgcctgg    2520
ccaaagtccc agaggactaa gggcctttct gggaatgggg gatcctctct cctatgtgga    2580
catggcaacc tgtatggggt ccccagtcac aggtctgtgc tcaccccat ctctgctttt    2640
tctcgccctt ccccgcaggc tgatcccgtc ctccactgag acctgaaaaa tggcttcggg    2700
gcaaggccca ggtcctccca ggcaggagtg cggagagcct gccctgccct ctgcttctgg    2760
taagggtctt cctgccccct cacccatccc ataaccatga gtgctgtcgt gaggatggaa    2820
ggagcaggac tcaggcaggc tccttcgcct cggttcaccc actgtgggtg gggaatactc    2880
ttccccaccc acgggctcag aggctggagc tgctgtcaag gttaagccca ggaggggag     2940
gagtctggac tggggagggc ctggaggttg ggagaggcca ggaagtgagt gtaaggtagg    3000
```

METHODS FOR TREATING GI SYNDROME AND GRAFT VERSUS HOST DISEASE

CROSS-REFERENCE TO RELATED APPLICATIONS

This application is a continuation of U.S. patent application Ser. No. 15/437,165, filed Feb. 20, 2017, which is a continuation of U.S. patent application Ser. No. 13/974,405, filed Aug. 23, 2013, which is a divisional of U.S. patent application Ser. No. 12/599,280, filed Nov. 6, 2009, which is a 371 national stage application of PCT Application No. PCT/US2008/062789, filed May 6, 2008, which claims priority to U.S. Provisional Patent Application No. 60/916,298, filed May 6, 2007, the entire contents of which are hereby incorporated by reference as if fully set forth herein, under 35 U.S.C. § 119(e).

STATEMENT OF GOVERNMENTAL INTEREST

This invention was made with government support under CA085704 awarded by the National Institutes of Health. The government has certain rights in the invention.

The instant application contains a Sequence Listing which has been submitted electronically in ASCII format in application Ser. No. 15/437,165, and is hereby incorporated by reference in its entirety. Said ASCII copy, created on Jun. 7, 2017, is named 115872-1211_SL.txt and is 36,160 bytes in size.

BACKGROUND OF THE INVENTION

1. Field of the Invention

The invention is in the field of methods for treating and preventing GI Syndrome and Graft Versus Host Disease.

2. Description of the Related Art

Radiation remains one of the most effective treatments for a wide variety of malignant cells; however healthy cells of the bone marrow, hair follicle, epidermis and gastrointestinal tract are extremely sensitive to radiation-induced cell death, limiting the effective use of this therapy for the treatment of cancer. Bone marrow transplantation is another way to treat advanced cancer, however, organ transplants frequently evoke a variety of immune responses in the host, which results in rejection of the graft and graft-versus-host disease (hereinafter, referred to as "GVHD"). Bone marrow transplantation is currently used to treat a number of malignant and non-malignant diseases including acute and chronic leukemias, myelomas, solid tumors (R. J. Jones, Curr Opin Oncol 3 (2), 234 (1991); G. L. Phillips, Prog Clin Biol Res 354B, 171 (1990)), aplastic anemias and severe immunodeficiency's (R. P. Gale, R. E. Champlin, S. A. Feig et al., Ann Intern Med 95 (4), 477 (1981); G. M. Silber, J. A. Winkelstein, R. C. Moen et al., Clin Immunol Immunopathol 44 (3), 317 (1987)). The conditioning regimen required prior to transplantation, designed to ablate or suppress the patient's immune system, renders the patient susceptible to neoplastic relapse or infection. Recent use of unrelated and HLA non-identical donors has unfortunately increased the incidence of GvHD. While removal of T cells from the donor marrow graft ameliorates GvHD, this strategy increases graft failure rates and markedly diminishes the therapeutically-beneficial graft-versus-tumor effect. As such, overall survival does not improve. Further, despite strong pre-clinical data, attempts to improve GvHD outcomes by diminishing inflammatory cytokine action by adding TNF antagonists to corticosteroids, the standard of care for acute GvHD, has provided limited therapeutic benefit. Thus there is an urgent need for alternative strategies to reduce the incidence and severity of GI syndrome and GvHD, if it is to be optimized clinically.

DESCRIPTION OF THE DRAWINGS

FIG. 2A: Frequency histograms of apoptotic cells in the villus lamina propria of irradiated asmase$^{+/+}$ and asmase$^{-/-}$ mice at 4 hours after 0 to 15 Gy TBI assessed by TUNEL staining. Apoptotic cells were scored in the lamina propria of 200 villae per point. Data represent mean scores from two experiments. FIG. 2B: Transverse sections of C3HeB/FeJ proximal jejunum were obtained either before irradiation or at 3.5 days after irradiation and stained with hematoxylin. Large hyperchromatic crypts are seen in the irradiated specimens (middle and lower panels), typical for surviving regenerating crypts, which are significantly enlarged as compared to control unirradiated crypts (upper panel). FIG. 2C: H&E-stained proximal jejunum and femur sections obtained from autopsy of asmase$^{+/+}$ and asmase$^{-/-}$ C57BL/6 following 15 Gy TBI. The day of lethality is noted.

FIGS. 3A-3C. Bax deficiency protects mouse intestines against radiation-induced endothelial apoptosis, crypt lethality and the lethal GI syndrome. C57Bl/6 mice were exposed to 15 Gy TBI (FIG. 3A) or 13-15 Gy (FIG. 3B) and tissue samples were obtained and processed as described in FIGS. 1 and 2A-2C. Similar results were obtained in two experiments for each response shown. Data are reported as mean apoptotic cells in the lamina propria of 200 villae per point (shown in FIG. 3A) and mean±SEM surviving crypts from 10-20 circumferences scored for each of 4 mice (shown in FIG. 3B). FIG. 3C: Actuarial survival curves of 8-12 week-old C57BL/6 mice receiving autologous bone marrow transplantation following exposure to 12-15 Gy TBI. Actuarial survival was calculated by the product limit Kaplan-Meier method [Kaplan, 1958 #47]. 4-10 animals were irradiated per group. Data represent collated survival results from multiple experiments.

FIG. 4A: Pre-incubation of Jurkat T cells with anti-ceramide MID15B4 (1 microgram/ml) 15 min prior to 10 Gy IR attenuated platform generation. Platforms were quantified by bright field microscopy following staining with anti-ceramide MID15B4 (1:30) and Texas-Red-conjugated anti-mouse IgM (1:500). FIG. 4B: Apoptosis was quantified in Jurkat cells by nuclear morphologic analysis following Hoechst bisbenzimide staining with or without preincubation with anti-ceramide MID15B4 (1 microgram/ml). Data are derived from minimum 150 cells obtained from three independent experiments.

FIG. 5A: Crypt survival assessed by the crypt microcolony assay. Surviving crypt were identified as shown in FIG. 4 and counted. Data for computation of the surviving fraction at each dose level was compiled from 2-4 animals irradiated concomitantly, with 10-20 circumferences scored per mouse. Data are reported as mean±SEM. FIG. 5B: Frequency histograms of apoptotic cells in the villus lamina propria of irradiated asmase$^{+/+}$ and asmase$^{-/-}$ mice 4 hours after 15 Gy TBI assessed by TUNEL staining. Apoptotic cells were scored in the lamina propria of 200 villae per point. Data represent collated mean scores from two experiments. FIG. 5C: Actuarial survival curves of 8-12 week-old C57BL/6 mice administered anti-ceramide or IgM and exposed to 15 Gy TBI. Actuarial survival was calculated by the product limit Kaplan-Meier method [Kaplan, 1958 #47]. 5-10 animals were irradiated per group. Similar data were observed in 3 experiments. FIG. 5D: Pretreatment of C57BL/6 mice with anti-ceramide MID15B4 (100 micrograms) 15 min prior to 15 Gy TBI attenuated endothelial apoptosis compared to control IgM treatments. Small intestine and lung tissue obtained 4 hrs following 15 Gy-irradiation were stained by TUNEL. Apoptotic cells are indicated by brown-stained nuclei. Data (mean±SEM) were obtained from minimum 150 villi from two independent experiments.

FIG. 13. 2A2 Antibody Attenuates Radiation-induced GI death in vivo, recapitulating the asmase$^{-/-}$ phenotype. Necropsy results of mice sacrificed when moribund from survival studies performed in FIGS. 12A-12D. GI death was assessed when proximal jejunum specimen appear >90% denuded of crypt-villi units and crypt regeneration is absent. Bone marrow (BM) death was assessed when decalcified femur sections reveal depletion of hematopoietic elements and massive hemorrhage.

FIGS. 15A-15B. Host ASMase regulates graft-vs.-host-associated morbidity and mortality. Lethally-irradiated (1100 cGy) C57BL/6$^{asmase+/+}$ or C57BL/6$^{asmase-/-}$ mice received intravenous injection of LP TCD-BM cells (5×10$^6$) with or without splenic T cells (3×10$^6$). Kaplan-Meier survival and clinical GvHD score;[117] derived from weekly assessment of 5 clinical parameters (weight loss, hunched posture, decreased activity, fur ruffling, and skin lesions) are shown in FIG. 15A and FIG. 15B respectively, representing 6-8 BM control and 13-14 BM+T cell recipients per group compiled from two experiments. Statistical analysis is as follows: (A) vs. ■ p<0.001, ■ vs. ● p<0.001. (B) vs. ■ p<0.05, ■ vs. ● p<0.05.

FIG. 16A: 2×10$^6$ GvH-activated CTLs were coincubated with 0.5×10$^6$ wild type C57BL/6 or B6.MRL.lpr (FasR$^{-/-}$) hepatocytes (left panel) in complete medium for 16 hr. Alternatively, DMSO or concanamycin A pre-treated (100 ng/ml, 30 min) GvH-activated CTLs were coincubated with 0.5×10$^6$ wild type C57BL/6 hepatocytes for 16 hr (right panel). Apoptosis was quantified following fixation by nuclear bisbenzimide staining. FIG. 16B: asmase$^{-/-}$ hepatocytes are resistant to apoptosis induced by GvH-activated CTLs. CTL coincubation was performed as in FIG. 16A and apoptosis was quantified 16 hr thereafter. FIG. 16C: Representative images of asmase$^{+/+}$ (top left panel) and asmase$^{-/-}$ (bottom left panel) C57BL/6 hepatocytes following 10 min coincubation in suspension with 2×10$^6$ GvH-activated T cells. Hepatocytes were fixed and stained with DAPI and Cy-3-labelled anti-ceramide mAb as described in Example 1. Arrows indicate ceramide-rich platform generation on the outer leaflet of the plasma membrane. Note that after incubation, cells were centrifuged at 50×g for 4 min at 4° C. prior to staining and imaging. Hence CTLs (small blue nuclei) distributed with hepatocytes (large blue nuclei) do not reflect biologic association. FIG. 16D: Quantification of ceramide-rich platforms in asmase$^{+/+}$ and asmase$^{-/-}$ hepatocytes following incubation with 2×10$^6$ GvH-activated CTLs. 0.5×10$^6$ hepatocytes were coincubated for the indicated times, fixed and stained as above.

FIG. 16E: Exogenous C$_{16}$-ceramide bypasses the requirement for target cell ASMase, conferring apoptosis onto GvH-activated CTL-stimulated asmase$^{-/-}$ hepatocytes. Apoptosis was quantified as in FIG. 16A. FIG. 16F: Disruption of membrane GEMs with nystatin inhibits CTL-induced hepatocyte apoptosis. 0.5×10$^6$ wild type hepatocytes, preincubated with 50 μg/mL nystatin for 30 min and resuspended in RPMI containing 1% lipid-free FBS, were coincubated with 2×10$^6$ GvH-activated T cells and apoptosis was quantified as in FIG. 16A. Data (mean±SEM) represent triplicate determinations from three independent experiments each for panels FIGS. 16A, 16B, 16D, 16E and 16F.

FIG. 19A: Representative images of ceramide-rich platforms (arrows) formed on the surface of Mitotracker Red-labeled, conA-activated (5 mg/ml for 24 hr) target C57BL/6$^{asmase+/+}$ and C57BL/6$^{asmase-/-}$ splenocytes, upon coincubation for 20 min with effector Balb/c splenic T cells that had been activated in vitro with 2×10$^6$ irradiated (2 Gy) C57BL/6 splenocytes/ml media for 5 days at a target:effector ratio of 2:1. Target splenocytes were fixed with 4% formalin-buffered phosphate, and stained with DAPI and FITC-labeled anti-ceramide mAb. FIG. 19B: Lysis of $^{51}$Cr-labelled target C57BL/6$^{asmase+/+}$ and C57BL/6$^{asmase-/-}$ splenocytes following coincubation with effector Balb/c splenic T cells for 6 hr measured by the chromium-release assay. FIG. 19C: Cytolytic response of $^{51}$Cr-labelled target C57BL/6$^{asmase-/-}$ splenocytes to activated effector Balb/c splenic T cells as in FIG. 19B, in the presence of 500 nM C$_{16}$-ceramide or C$_{16}$-dihydroceramide (DCer). FIG. 19D: Representative images of ceramide-rich platforms (arrows) formed on the surface of C57BL/6$^{asmase+/+}$ and C57BL/6$^{asmase-/-}$ C57BL/6 splenic T cells 4 hr following induction of AICD with 10 ng/ml anti-CD3 as described in Materials and Methods. Cells were fixed with 4% formalin-buffered phosphate, and stained with DAPI and FITC-labeled anti-ceramide mAb. AICD induces a 2.0±0.1 fold increase in the overall ceramide signal as determined by mean fluorescence intensity in asmase$^{+/+}$ T cells (p<0.005 compared to unstipulated controls), not evident in asmase$^{-/-}$ T cells, accounting for the difference in overall staining between panels. FIG. 19E: Confocal microscopic detection of ceramide (second panels from top) and GM$_1$ (third panels from top) colocalization in platforms following AICD induction as in FIG. 19D. Platforms were identified using Cy3-anti-mouse IgM detection of anti-ceramide MID15B4 and FITC-conjugated cholera toxin, respectively. FIG. 19F: Apoptotic response of C57BL/6$^{asmase+/+}$ or C57BL/6$^{asmase-/-}$ splenic T cells after AICD apoptotic fratricide was induced as in FIG. 19D. Apoptosis was quantified 16 hr thereafter following nuclear bisbenzimide staining. FIG. 19G: AICD was initiated in C57BL/6$^{asmase-/-}$ splenic T cells as in FIG. 19D, in the presence of 500 nM C16-ceramide or C$_{16}$-dihydroceramide. Apoptosis was quantified 16 hr thereafter following nuclear bisbenzimide staining. Data (mean±SEM) represent triplicate samples from three independent experiments for panels FIGS. 19B, 19C, 19F, and 19G.

FIGS. 22A-22E. Host ASMase determines graft-vs.-host target organ injury and apoptosis. C57BL/6$^{asmase+/+}$ or C57BL/6$^{asmase-/-}$ mice received transplants and were sacrificed 21 days thereafter for histopathologic analysis. FIG. 22A: Representative 5 μM H&E-stained liver sections showing increased lymphocyte infiltration, portal tract expansion and endotheliitis in asmase$^{+/+}$ hosts receiving allogeneic T cells compared to asmase$^{-/-}$ littermates. FIG. 22B: Representative 5 μM TUNEL-stained sections of proximal jejunal crypts and villi display lamina propria and crypt apoptosis. Arrows indicate cells containing condensed or fragmented brown nuclei contrasting with the blue stain of non-apoptotic nuclei, quantified in FIG. 22C and FIG. 22D, respectively. Frequency histograms of apoptotic cells in the villus lamina propria FIG. 22C represent data from 150 villae per point, collated from 2 experiments. Crypt apoptosis FIG. 22D was scored in 200 crypts per point, and represent mean±SEM collated from 2 experiments. FIG. 22E C57BL/6 recipient hosts received marrow transplants as above, or alternatively, 10×10$^6$ TCD-BM cells with or without 0.5×10$^6$ T cells from B10.BR (H2$^k$) donors. Skin (tongue and ear) were harvested 14 (B10.BR recipients) or 21 (LP) days post marrow transplant and GvHD score was determined by the number of dyskeratotic and apoptotic keratinocytes per millimeter of epidermis (mean±SEM) as assessed in blinded fashion on H&E-stained sections. Data represent 4-14 mice per group compiled from three independent experiments.

FIGS. 23A-23B. Donor CD8$^+$ T cell expansion are impaired in asmase$^{-/-}$ hosts. FIG. 23A: C57BL/6$^{asmase+/+}$ and C57BL/6$^{asmase-/-}$ recipients were infused with 15-20$^6$ CFSE-stained splenic CD3$^+$ T cells from LP/J donors as described in Example 1. Spleens were harvested 72 hrs thereafter and multicolor flow cytometry was performed. Percentage of CFSE "high" (cells with mean fluorescent values >10$^3$) and "low" (mean fluorescent values <10$^3$) CD4$^+$ and CD8$^+$ populations are shown from one representative of two independent experiments. FIG. 23B: Flow cytometric analysis of Ly9.1$^+$ donor LP/J T cells harvested from C57BL/6 asmase$^{+/+}$ and asmase$^{-/-}$ recipients 14 days following LP/J BM and T cell infusion, as described in Example 1. Data (mean±SEM) represent 4-12 determinations from two independent experiments.

LIST OF ABBREVIATIONS

Figure 1:
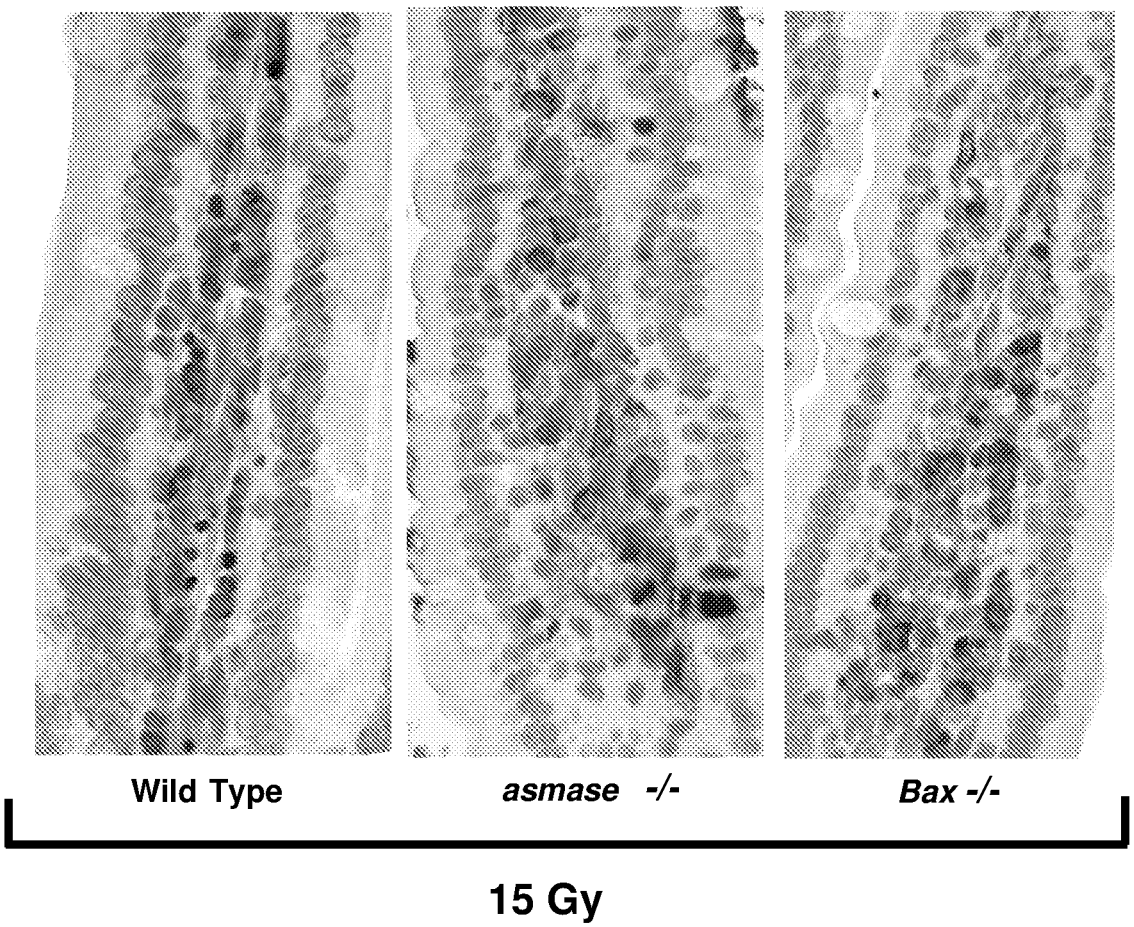
FIG. 1. ASMase and Bax deficiency protect C57BL/6 intestinal mucosa against radiation-induced microvascular endothelial apoptosis. Proximal jejunal specimens were obtained at 4 hours after 15 Gy TBI of wild type (second panel) and asmase$^{-/-}$ (third panel) and Bax$^{-/-}$ (fourth panel) C57BL/6 mice, and compared with a specimen obtained from an unirradiated wild type mouse (first panel). Apoptotic nuclei of endothelial cells (red, CD31 stain) were identified in the villus lamina propria by TUNEL staining as condensed or fragmented brown nuclei contrasting with the blue stain of non-apoptotic nuclei. Arrows indicate apoptotic endothelial cells.

ASMase—acid sphingomyelinase BMT—bone marrow transplant CTLs—cytotoxic T lymphocytes
ERK—extracellular signal-related kinase
FADD—Fas-associated death domain FcRγII—Fc receptor γII
FITC—fluorescein isothiocyanate
GVHD—Graft-Versus-Host-Disease GVT—Graft-Versus-Tumor
IL—interleukin
JNK—c-Jun N-terminal kinase
mHAg(s)—minor histocompatability antigen(s)
MHC—major histocompatibility complex MLR—mixed lymphocyte reaction
SDS-PAGE—sodium dodecyl sulfate-polyacrylamide gel electrophoresis TCR—T cell receptor
TNF—tumor necrosis factor
TUNEL—terminal dUTP nick-end labeling

DETAILED DESCRIPTION

We have discovered that administering anti-ceramide antibody treats and prevents an array of diseases mediated by cytolytic T lymphocyte (CTLs)-induced killing and by damage to endothelial microvasculture, including radiation-induced GI syndrome, Graft vs Host diseases, inflammatory diseases and autoimmune diseases (herein the enumerated diseases). We have also discovered a new anti-ceramide monoclonal antibody 2A2 and others described below, that have therapeutic use preferably in humanized form to treat or prevent the enumerated diseases. Identified as Myeloma cell fused with spleen cells from Balb/c mouse: 2A2.1.1.1.1, the submission was deposited as ATCC Deposit No. PTA-13418 on Jan. 9, 2012. The ATCC number referred to above is directed to a biological deposit with the ATCC, 10801 University Boulevard, Manassas, Va. 20110-2209. The strain referred to is being maintained under the terms of the Budapest Treaty and will be made available to a patent office signatory to the Budapest Treaty. Other embodiments of the invention are directed to combination therapy to treat or prevent the above enumerated diseases by administering anti-ceramide antibody together with one or more statins; or with imipramine or other ASMase inhibitor or Bax inhibitor. Yet other embodiments include administering an antisense nucleotides or small interfering RNA in an amount that reduces expression of ASMase, Bax and Bak or otherwise reduces or ameliorates a symptom of any of the enumerated diseases. Finally, certain embodiments are directed to compositions for therapeutic use in treating or preventing the enumerated diseases that include an anti-ceramide antibody and one or more statins or imipramine.

Extracellular Ceramide is Required for Radiation-Induced Apoptosis

Lipid rafts, which are distinct plasma membrane microdomains comprised of cholesterol tightly packed with sphingolipids, in particular sphingomyelin, creating a liquid-ordered domain within the liquid-disordered bulk plasma membrane. Rafts differ in their protein and lipid composition from the surrounding membrane, housing signaling molecules including multiple glycosylphosphatidylinositol (GPI)-anchored proteins, doubly-acylated tyrosine kinases of the Src family and transmembrane proteins. In addition, rafts serve as sites that multiple receptors translocate into or out of upon their activation, including the B cell receptor (BCR) upon encountering antigen. Recent evidence suggests that these translocation events are crucial for multiple signal transduction cascades.

Sphingolipids, which were classically viewed as structural components of cell membranes, were discovered to be important regulators of signal transduction by the determination that 1,2-diacylglycerols stimulated sphingomyelin hydrolysis to ceramide[5] By identifying activation of an acidic sphingomyelinase (ASMase) that generates ceramide in GH3 pituitary cells, these studies introduced a potential role for ceramide as a second messenger. This role was supported by the identification of modulated protein phosphorylation events and kinase activity in vitro by addition of exogenous ceramides (R. N. Kolesnick and M. R. Hemer, *J Biol Chem* 265 (31), 18803 (1990), S. Mathias, K. A. Dressler, and R. N. Kolesnick, *Proc NatlAcad Sci USA* 88 (22), 10009 (1991)). Ultimately, the coupling of tumor necrosis factor receptor (TNFR) activation with ceramide generation in a cell free system, antagonism of TNF-α-mediated signaling by inhibition of ceramide generation, and the recapitulation by exogenous ceramides of TNF-α signaling in cells devoid of ceramide generation established ceramide as a bonafide lipid second messenger (K. A. Dressler, S. Mathias, and R. N. Kolesnick, *Science* 255 (5052), 1715 (1992)).

Acid sphingomyelinase (ASMase) is a sphingomyelin-specific phospholipase C (sphingomyelin phosphodiesterase) that exists in two forms, a lysosomal and secretory form; it initiates a rapid stress response in many cell types (R. Kolesnick, *Mol Chem Neuropathol* 21 (2-3), 287 (1994); J. Lozano, S. Menendez, A. Morales et al., *J Biol Chem* 276 (1), 442 (2001); Y. Morita, G. I. Perez, F. Paris et al., *Nat Med* 6 (10), 1109 (2000); F. Paris, Z. Fuks, A. Kang et al., *Science* 293 (5528), 293 (2001); Santana, L. A. Pena, A. Haimovitz-Friedman et al., *Cell* 86 (2), 189 (1996)). Our recent work showed that clustering of plasma membrane lipid rafts into ceramide-enriched platforms amplify stimuli capable of activating ASMase. Grassme et al., J Biol Chem. 2001, 276:20589, incorporated herein by reference. In these studies we showed that in vitro and in vivo, extracellularly orientated ceramide, released upon CD95-triggered translocation of ASMase to the plasma membrane outer surface, enabled clustering of CD95 in sphingolipid-rich membrane rafts and induced apoptosis in Jerkat cells. Whereas ASMase deficiency, destruction of rafts, or neutralization of surface ceramide prevented CD95 clustering and apoptosis, natural ceramide rescued ASMase deficient cells. The data showed that CD95-mediated clustering by ceramide is a prerequisite for signaling and apoptotic cell death. Jurkat cells are a human T cell leukemia cell line.

Others have shown that ceramide is required for Fas-induced apoptosis in some cell types. We looked at the requirement for UV-C-induced ceramide generation in initiating the apoptotic response. By UV-C is meant ultraviolet radiation in the 100-280 nm wavelength range. In these studies imipramine was used to inhibit ASMase-activity. Pre-treatment of Jurkat cells with 50 mM imipramine for 30 min decreased baseline ASMase activity, abrogated UV-C and Fas-induced ASMase activation at 1 min post stimulation and ceramide generation at 2 minutes, and attenuated apoptosis at 4 hours post-stimulation. These data showed that ASMase activation is indispensable for optimal Fas- or UV-C-induced apoptosis, though they do not define the role of ceramide per se in this response. Grassme et al., J Biol Chem. 2001, 276:20589, incorporated herein by reference.

Ceramide has important roles in differentiation, proliferation and growth arrest, but the most prominent role for ceramide is in the induction of programmed cell death. Exogenous $C_8$ ceramide and sphingomyelinase mimicked TNF-α-induced DNA fragmentation and loss of clonogenicity in HL60 human leukemia cells, suggesting that ceramide was an essential component of apoptotic signaling (K. A. Dressler, S. Mathias, and R. N. Kolesnick, Science 255 (5052), 1715 (1992). Ionizing radiation (IR) stimulates sphingomyelin hydrolysis to ceramide, and exogenous ceramide was able to bypass phorbol ester-mediated inhibition of radiation-induced ceramide generation and apoptosis (A. Haimovitz-Friedman, C. C. Kan, D. Ehleiter et al., J Exp Med 180 (2), 525 (1994)). Lymphoblasts derived from Niemann-Pick patients, a genetic disease characterized by an inherited deficiency in ASMase activity, proved in a genetic model that ASMase-mediated ceramide generation is required for radiation-induced apoptosis, and the development of an ASMase-deficient mouse allowed the identification of cell-type specific roles for ceramide (J. Lozano, S. Menendez, A. Morales et al., J Biol Chem 276 (1), 442 (2001); P. Santana, L. A. Pena, A. Haimovitz-Friedman et al., Cell 86 (2), 189 (1996)). Ceramide generation has since been identified as requisite for multiple cytokine-, virus/pathogen-, environmental stress-, and chemotherapeutic-induced apoptotic events. Verheij M, et al.

Requirement for ceramide-initiated SAPK/JNK signaling in stress-induced apoptosis. Nature. 1996 Mar. 7; 380(6569): 75-9; Riethmüller J, et al., Membrane rafts in host-pathogen interactions, Biochim Biophys Acta. 2006 December: 1758(12):2139-47, incorporated herein by reference.

An emerging body of evidence has since recognized ceramide-mediated raft clustering as sites of signal transduction for bacteria and pathogen internalization, and radiation- and chemotherapeutic-induced apoptosis. D. A. Brown and E. London, Annu Rev Cell Dev Biol 14, 111 (1998): J. C. Fanzo, M. P. Lynch, H. Phee et al., Cancer Biol Ther 2 (4), 392 (2003); S. Lacour, A. Hammann, S. Grazide et al., Cancer Res 64 (10), 3593 (2004); Semac, C. Palomba, K. Kulangara et al., Cancer Res 63 (2), 534 (2003; A. B. Abdel Shakor, K. Kwiatkowska, and A. Sobota, J Biol Chem 279 (35), 36778 (2004); H. Grassme, V. Jendrossek, J. Bock et al., J Immunol 168 (1), 298 (2002); M. S. Cragg, S. M. Morgan, H. T. Chan et al., Blood 101 (3), 1045 (2003);[6] D. Scheel-Toellner, K. Wang, L. K. Assi et al., Biochem Soc Trans 32 (Pt 5), 679 (2004).; D. Delmas, C. Rebe, S. Lacour et al., J Biol Chem 278 (42), 41482 (2003).; and C. Bezombes, S. Grazide, C. Garret et al., Blood 104 (4), 1166 (2004).

In this context, ceramide-enriched platforms transmit signals for IR-induced apoptosis of Jurkat cells (Zhang and Kolesnick, unpublished results) and bovine aortic endothelial cells (Stancevic and Kolesnick, unpublished results), CD40-induced IL-12 secretion and c-Jun Kinase phosphorylation in JY B cells, P. aeruginosa internalization and activation of the innate immune response in lung, Rituximab-induced CD20 clustering and ERK phosphorylation in Daudi and RL lymphoma cells, FcRγII clustering and phosphorylation in U937 human monocytic cells, and resveratrol-, cisplatin- and reactive oxygen species-induced apoptosis in HT29 human colon carcinoma cells and neutrophils. Despite extensive studies on the downstream effects of ASMase translocation and activation, little was known of the initiating events mediating its translocation onto the outer plasma membrane until we showed that there is a capsase-independent pathway that initiates ASMase signaling. J. A. Rotolo et al., J. Biol. Chem. Vol 280, No. 29, Issue of Jul. 15, 26425-34 (2005), incorporated herein by reference.

It is important to emphasize that there are multiple pathways in a cell to make ceramide in different compartments. Ceramide generated at the cell surface in rafts by ASMase is different from ceramide inside the cell. The results presented below show for the first time that ASMase-generated cell surface ceramide is responsible for causing radiation-induced GI syndrome through damage to endothelial microvasculature (a hallmark of GI syndrome). We further show that ASMase-generated ceramide is required for GVHD caused by T-cell mediated killing. Thus ASMase generated ceramide is required for both endothelial microvasculature damage and T-cell mediated killing. We have further discovered that inhibiting or sequestering ceramide generated by ASMase by administering anti-ceramide antibodies in vivo, reduced radiation-induced damage, and can be sued to treat or prevent GI syndrome and GvHD. Certain embodiments of the present invention are directed to pharmacological methods to treat or prevent GVHD and GI syndrome and other T-cell mediated diseases including autoimmune diseases, by blocking ASMase (for example with imipramine or with antisense nucleic acids) or by inactivating cell surface ceramide (for example with anti-ceramide antibodies alone or together with statins).

Treatment and Prevention of the Lethal GI Syndrome

The intestinal clonogenic compartment housing stem cells of the small intestine resides at positions 4-9 from the bottom of the crypt of Lieberkuhn, and consists of intestinal pluripotent stem cells and uncommitted progenitor clonogens, herein called stem cell clonogens. This group of cells proliferates and differentiates incessantly, replenishing the physiologic loss of enterocytes and other differentiated epithelial cells from the villus apex, thus maintaining the anatomical and functional integrity of the mucosa. A complete depletion of this compartment appears required to permanently destroy the crypt-villus unit, while surviving stem cell clonogens, albeit even one per crypt, are capable of regenerating a fully functional crypt.

Radiation targets both the gastrointestinal microvasculature and proliferating crypt stem cells. Apoptosis of the microvascular endothelium in the villus represents the primary lesion of the GI syndrome, occurring 4 hours following radiation. Endothelial apoptosis converts lesions to the crypt clonogens from sublethal to lethal, resulting in loss of regenerative crypts and promoting GI toxicity. Immunohistochemical and labeling studies with [$^3$H]TdR and BrdUrd revealed that crypt stem cell clonogen death does not occur acutely after radiation exposure. Rather, the earliest detectable response is a temporary dose-dependent delay in progression through a late S-phase checkpoint and mitotic arrest, apparently signaled by radiation-induced DNA double strand breaks (dsb). In mammalian cells, DNA dsbs activate pathways of DNA damage recognition and repair, and a coordinated regulation of cell cycle checkpoint activity. The intestinal stem cell mitotic arrest appears to represent a regulated event in this pathway. Consistent with this notion, no significant change in crypt number per intestinal circumference is apparent at this stage although crypt size progressively decreases due to continued normal migration of crypt transit and differentiated cells from the crypt into the epithelial lining of the villus. Resumption of mitotic activity at 36-48 hours is associated with a rapid depletion of crypt stem cell clonogens and reduction in the crypt number per circumference. The mechanism of stem cell depletion has not been fully established.

The lethality of GI stem cell clonogens is best assessed by the number of crypts surviving at 3.5 days after radiation exposure, which decreases exponentially as the dose increases (C. S. Potten and M. Loeffler, *Development* 110 (4), 1001 (1990), H. R. Withers, *Cancer* 28 (1), 75 (1971), and J. G. Maj, F. Paris, A. Haimovitz-Friedman et al., *Cancer Res* 63, 4338 (2003)). Crypts that contain surviving stem cells proliferate at an accelerated rate, producing typical regenerative crypts that split or bud to generate new crypts, until the intestinal mucosa regains a normal architecture. TBI experiments in several mouse models have demonstrated that the number of surviving crypt stem cells after exposure to 8-12 Gy is usually sufficient to support a complete recovery of the mucosa. At higher doses, however, massive stem cell clonogen loss may lead to a near total collapse of the crypt-villus system, mucosal denudation and animal death from the GI syndrome. The threshold dose for inducing the GI death, and the TBI dose producing 50% GI lethality ($LD_{50}$), appear to be strain-specific. Autopsy studies of C57BL/6 mice exposed to TBI revealed that 25% of the mice exposed to 14 Gy and 100% of those exposed 15 Gy succumbed to the GI syndrome at 6.8±0.99 days, predicting an $LD_{50}$ for GI death between 14 and 15 Gy. In contrast, the reported $LD_{50/6}$ (the $LD_{50}$ at day 6, serving as a surrogate marker for GI death) for BALB/c mice is 8.8±0.72 Gy, 11.7±0.22 Gy for BDF1 mice, 12.5±0.1 Gy for C3H/He mice, 14.9 Gy (95% confidence limits 13.9-16.0 Gy) for C3H/SPF mice, and 16.4±1.2 Gy for B6CF1 mice, indicating a strain-specific spectrum in mouse sensitivity to death from the GI syndrome. Strain variations in the sensitivity of other organs to radiation, such as the bone marrow and lung have also been reported.

Classically, ionizing radiation (IR) was thought to kill cells by direct damage to genomic DNA, causing genomic instability and resulting in reproductive cell death. Haimovitz-Friedman et al. demonstrated in a nuclei-free system that apoptotic signaling can alternately be generated by the interaction of IR with cellular membranes. Extension of these studies by us and described herein revealed that ceramide mediated raft clustering is involved in IR-induced apoptosis and clonogenic cell death. It has long been accepted that the clonogenic compartment of the gastrointestinal (GI) mucosa is the specific and direct target for radiation in inducing GI damage.

In some of our early work we showed that greater protection against ultra violet radiation with UV-C (5-50 $J/m^2$)- and anti-Fas (1-50 ng/ml CH-11)-induced apoptosis in vitro was obtained by inducing ceramide neutralization with anti-ceramide monoclonal antibody combined with cholesterol depletion induced by nystatin in Jurkat cells, than was obtained using either agent alone. H. Grassme, H. Schwarz, and E. Gulbins, Biochem Biophys Res Commun 284 (4), 1016 (2001), incorporated herein by reference. In these studies we showed that preincubation of Jurkat cells with anti-ceramide antibody in combination with nystatin inhibited raft clustering 1 min post 50 $J/m^2$ UV-C- or 50 ng/ml anti-Fas stimulation. Furthermore, inhibiting raft clustering by anti-ceramide and nystatin combination treatment attenuated UV-C (5-50 $J/m^2$)- and anti-Fas (1-50 ng/ml CH-11)-induced apoptosis 4 hours post stimulation (FIG. 2d) and enhanced cell viability by 2.46- and 2.42-fold, respectively, 7 days post stimulation with 50 $J/m^2$ UV-C or 50 ng anti-Fas. Importantly, we also observed that anti-ceramide and nystatin pretreatment yielded an approximate 1 log increase in clonogenic cell survival compared to vehicle controls after 5-50 $J/m^2$ UV-C or anti-Fas stimulation. Plotting these clonogenic survival data according to the single-hit multitarget model revealed that pretreatment with anti-ceramide and nystatin increased the $D_0$ of the dose response curve from 1.6±0.7 $J/m^2$ to 3.6±1.1 $J/m^2$, indicating significant (p<0.05) protection against the reproductive mode of UV-induced cell death, with a dose modifying value of 2.32 at the 10% survival level. Taken together, these results showed that ceramide-mediated raft clustering at the surface of Jurkat cells is obligate for apoptotic transmembrane signal transduction induced by UV-C, and that such protection is biologically-relevant as evidenced by improved clonogenic survival.

There is evidence for a conditional linkage between crypt stem cell clonogen lethality after single-dose radiation and the early wave of ASMase-mediated apoptosis in the endothelium of the intestinal microvascular system. Radiation induces rapid translocation of a secretory non-lysosomal form of ASMase into glycosphingolipid- and cholesterol-enriched rafts in the outer leaflet of the plasma membrane (E. Gulbins and R. Kolesnick, *Oncogene* 22 (45), 7070 (2003) where ceramide is rapidly generated, coordinating transmembrane signaling of apoptosis. Endothelial cells are 20-fold enriched in secretory ASMase compared with other cells in the body, and this cell type is particularly sensitive to radiation-induced apoptosis in vitro and in vivo. Genetic inactivation of ASMase in SV129/C57BL/6 mice, or intravenous treatment of C57BL/6 mice with the endothelial cell survival factor bFGF prior to whole body irradiation (TBI), attenuated radiation-induced endothelial apoptosis of the intestinal microvascular system, preserved crypt stem cell clonogens, and protected mice against lethality from the GI syndrome (F. Paris, Z. Fuks, A. Kang et al., *Science* 293 (5528), 293 (2001)). Given that the intestinal endothelium but not crypt epithelial cells expressed bFGF receptor transcripts before or after irradiation, vascular dysfunction appeared critical for radiation-induced GI damage.

ASMase- and Bax-Deficiency Protects Against Radiation Damage and GI Syndrome

This section describes our experiments showing that both asmase$^{-/-}$ and Bax$^{-/-}$ mice are resistant to endothelial apoptosis occurring within 4 hours of total body irradiation (TBI). This allows the repair of sublethal lesions incurred by crypt clonogens, regenerating the crypt-villus system and abrogating the lethal GI syndrome. The well-characterized parameters of the GI syndrome make this system an ideal model for study of ceramide targeting pharmaceuticals. Below we show that anti-ceramide antibody attenuated microvascular apoptosis to the level similar to that of the asmase$^{-/-}$ genotype, promoting clonogenic crypt stem cell survival and GI regeneration. Anti-ceramide protected 60% of mice receiving 15 Gy TBI and syngeneic BMT, demonstrating that the microvascular protection is biologically relevant.

Figure 2A:
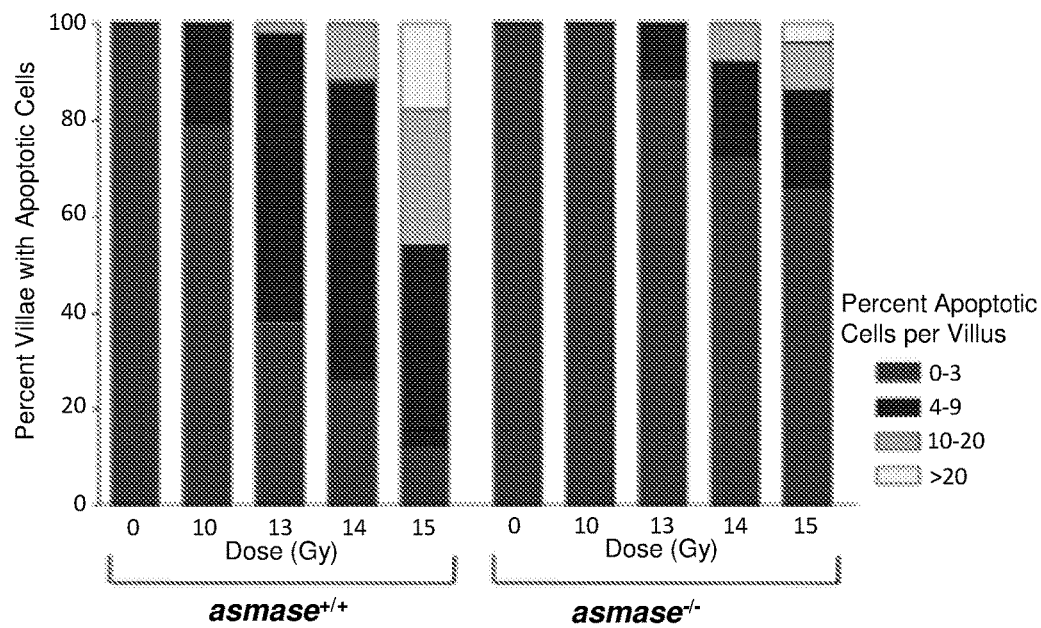
FIGS. 2A-2C. ASMase deficiency protects intestinal mucosa against radiation-induced microvascular endothelial apoptosis and crypt stem cell lethality.

Previous studies identified an endothelial-stem cell clonogen linkage in the GI radiation response of the C57BL/6 mouse strain and its SV129/C57BL/6 hybrid. Further, these studies characterized the role of ASMase in the GI radiation response in the SV129/C57BL/6 hybrid strain. F. Paris, et al. supra. To examine whether genetic inactivation of ASMase protects C57BL/6 from the vascular component in the intestinal response to radiation, several of the features that characterize the SV129/C57BL/6 mice intestinal response to radiation were evaluated in asmase$^{+/+}$ and asmase$^{-/-}$ C57BL/6 mice. Typical histologic examples of the pattern of endothelial response to radiation in asmase$^{+/+}$ and asmase$^{-/-}$ genotypes in this strain are shown (FIG. 1). Consistent with published observations on SV129/C57BL/6 mice, wild type C57BL/6 mice show extensive endothelial apoptosis at 4 hours after 15 Gy TBI (12 apoptotic endothelial nuclei in the villus lamina propria; FIG. 1 second panel), reduced in the asmase$^{-/-}$ and Bax$^{-/-}$ specimen to 3 apoptotic nuclei each (FIG. 1, third and fourth panel, respectively). Only occasional (1-3) apoptotic nuclei were observed in the lamina propria of an unirradiated control asmase$^{+/+}$ (FIG. 1, first panel), asmase$^{-/-}$ or Bax$^{-/-}$ (not shown). Endothelial cell apoptosis was detected in the wild type mucosa as early as at 3 hours after exposure to 15 Gy and reached a maximum at 4 hours (not shown). FIG. 2 A displays a frequency histogram of apoptotic nuclei in the intestinal lamina propria of C57BL/6 mice at 4 hours after exposure to escalating doses of TBI. A maximal effect was observed in the asmase$^{+/+}$ mucosa at 15 Gy, with 92% of the villae displaying >3 apoptotic nuclei/villus and 52% displaying extensive apoptosis (>10 apoptotic nuclei/villus), compared to ≤3 apoptotic nuclei/villus observed in control unirradiated mice (p<0.001; n=200 villae from 2 animals counted for each data point). ASMase deficiency significantly reduced the overall apoptotic response (>3 apoptotic nuclei/villus) to 38% and the frequency of extensive apoptosis to 20% of the total villae (p<0.001 each compared to wild type littermates, respectively; n=200 villae from 2 animals counted for each data point). Thus, the kinetics and dose-dependency of radiation-induced endothelial cell apoptosis in the C57BL/6 strain, and the requirement for ASMase, were qualitatively and quantitatively similar to those in the SV129/C57BL/6 mouse strain[1] although the peak incidence of the apoptotic response occurred 1 hour later than in the SV129/C57BL/6 strain.

Figure 2B:
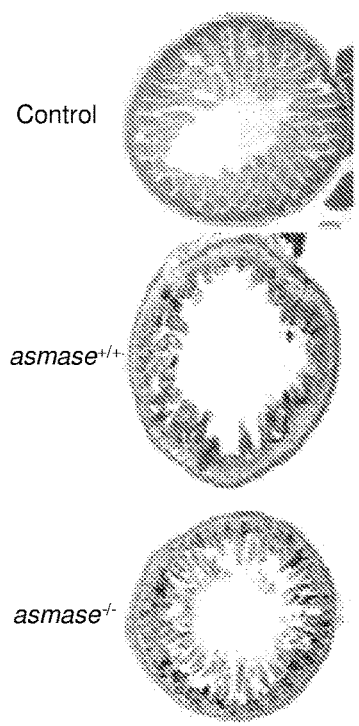

As reported for SV129/C57BL/6 mice (J. G. Maj, F. Paris, A. Haimovitz-Friedman et al., *Cancer Res* 63, 4338 (2003)), endothelial apoptosis closely correlated with survival of crypt stem cell clonogens after TBI. FIG. 2b shows typical cross sections of C57BL/6 mice proximal jejunum at 3.5 days after exposure to 15 Gy TBI. When unirradiated, the number of crypts/intestinal circumference in this strain was 155±1.1. After exposure to 15 Gy, a specimen from a C57BL/6$^{asmase+/+}$ mouse shown contained only 3 surviving regenerating crypts, compared with 27 in the specimen obtained from a C57BL/6$^{asmase-/-}$ littermate. ASMase deficiency significantly increased the crypt surviving fraction at each dose within the range of 10-15 Gy (p<0.05). Wild type mice 3.5 days following exposure to 15 Gy TBI are nearly completely depleted of functional proximal jejunal crypts (FIG. 2b, middle panel). Genetic inactivation of ASMase enhanced crypt survival as evidenced by increased expression of dark-purple stained regenerative, hyperchromatic crypts (FIG. 2b, bottom panel). The dose required to produce an isoeffect of 10% crypt survival ($D_{10}$) was 14.6±0.9 Gy for wild-type and 16.8±1.8 Gy for the ASMase-deficient mice (p<0.01), indicating a dose-modifying factor (DMF) of 1.15±0.14 for the asmase$^{-/-}$ genotype. This value was not different significantly from the DMF reported for protection of irradiated C57BL/6 crypt stem cell clonogens by bFGF[7].

Figure 2C:
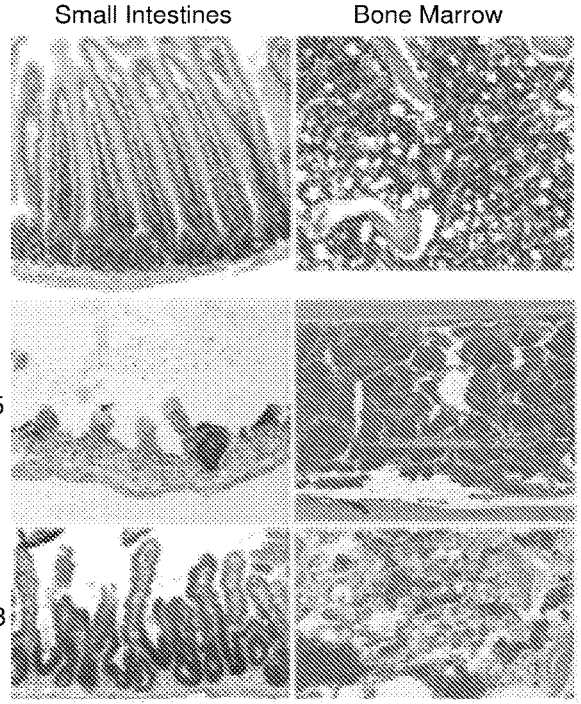

The stem cell clonogen protection afforded by ASMase deletion also translated into protection against C57BL/6 mouse death from the GI syndrome after 15 Gy TBI, similar to that reported for hybrid SV129/C57BL/6asmase-/- mice1. By contrast p53-deficient C57BL/6 mice were not protected from radiation damage (data not shown.) C57BL/6asmase+/+ mice died at 5-6 (mean 5.3±0.2) days after TBI (not shown). Autopsies revealed intestinal damage typical of the GI syndrome (extensive denudation of nearly all the crypts and villae) with only partial damage to the bone marrow (regions of hemorrhage and depletion of hematopoietic elements mixed with islands of normal hematopoietic tissue; FIG. 2c left and right middle panels, respectively;). Other organs were found intact, except for thymic and lymphatic tissues, and occasional micro-abscesses or focal hemorrhages in various organs, not considered as direct causes of death. In contrast C57BL/6$^{asmase-/-}$ mice died at 7.75±0.12 days (p<0.001 when compared to C57BL/6$^{asmase+/+}$ mice). Autopsies revealed typical characteristics of bone marrow death (widespread hemorrhage and extensive necrosis of the matrix, with complete depletion of hematopoietic elements; FIG. 2c, right lower panel). Further, in contrast to the complete destruction of the crypt/villus network in C57BL/6$^{asmase+/+}$ mice, the intestinal mucosa of C57BL/6$^{asmase-/-}$ littermates showed extensive regenerative activity with hyperplastic, chromophilic crypts covering most of the intestinal surface (FIG. 2c, left lower panel).

Bax Deficiency Phenocopies Asmase$^{-/-}$ Protection from Radiation Damage and GI Syndrome To eliminate the possibility that an event other than endothelial cell apoptosis, induced by radiation and regulated by ASMase, might impact the lethality of radiation-injured stem cell clonogens. Experiments were carried out with the apoptosis-refractory Bax-deficient C57BL/6 mice that express wild-type ASMase and mimic the asmase$^{-/-}$ radiation phenotype in tumor endothelium an in oocytes of young mice. Bax and Bak are prototypical proapoptotic Bcl-2 multidomain proteins. Double deletions (homozygous recessive Bax-/- and Bak-/- mutations) were previously believed to be required to endow resistance to apoptotic stimuli. Data for Bak- deficient mice is not shown.

The wild type C57BL/6$^{Bax+/+}$ strain used in these experiments displayed no detectable baseline endothelial cell apoptosis, and underwent a time-dependent increase after exposure to 15 Gy TBI that peaked at 4 hours (not shown). 85% of the villae contained >3 endothelial apoptotic nuclei/villus at 4 hours after 15 Gy, and 38% showed an extensive (>10 apoptotic nuclei/villus) apoptotic response (FIG. 3). Bax deficiency significantly reduced the overall radiation-induced apoptotic response to 45% (p<0.05), and the frequency of extensive apoptosis to 12% of the villae (p<0.001; n=200 villae from 2 animals counted for each data point), mimicking the previously reported asmase$^{-/-}$ radiation-response phenotype in C57BL/6 and SV129/C57BL/6. Attenuation of endothelial apoptosis by Bax deficiency protected crypt clonogens following exposure to 13, 14 and 15 Gy TBI (FIG. 3b). Surviving crypts in wild type C57BL/6 mice at 3.5 days following 13, 14 and 15 Gy TBI, reputedly a measure of surviving crypt stem cells, was decreased from 152±3 in unirradiated intestinal circumferences to 20.5±1.3, 10.8±0.6 and 2.3±0.3 respectively (surviving fractions of 13.4±0.9%, 7.0±0.4% and 1.47±0.2%, respectively, n=10-20 circumferences each from 4 animals per point). Bax deficiency increased the number of surviving crypts following 13, 14 and 15 Gy TBI vs. wild type controls to 42.3.7±2.0, 27.6±1.6 and 18.2±1.3, respectively (surviving fractions of 27.8±1.4%, 18.2±1.1% and 12.0±0.9%, respectively, P<0.001 vs. wild type C57BL/6, FIG. 3b). The fraction of surviving crypts in C57Bl/6$^{Bax-/-}$ mice following 13-15 Gy exceeded the 8.5±0.1% surviving crypts reported necessary to support mucosal recovery and prevent GI death in wild type C57Bl/6 mice treated with 12 Gy alone[62,71]. These data are consistent with the notion of a linkage between endothelial apoptosis and survival of crypt stem cell clonogens after radiation exposure. J. A. Rotolo, et al, Int. J. Radiation Oncology Biol. Phys., Vol. 70, No. 3, 804-815(2008), incorporated herein by reference.

Figure 3C:
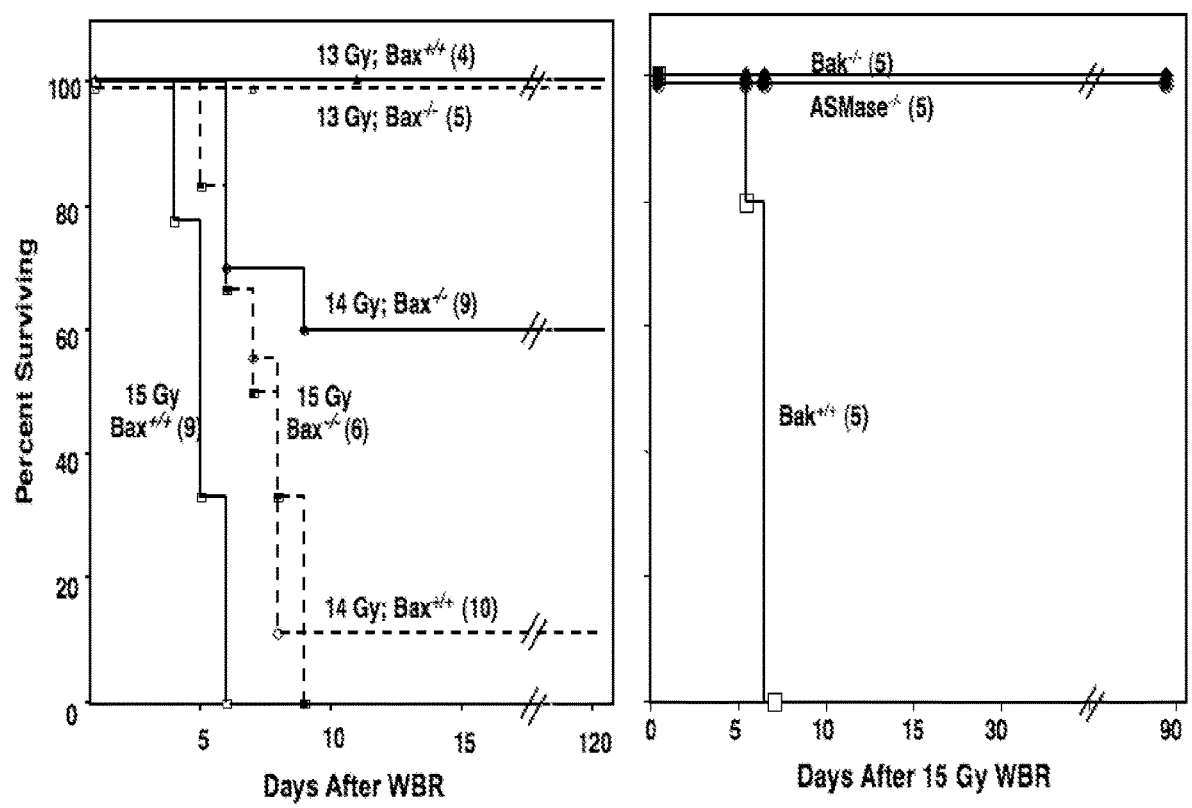

The stem cell clonogen protection provided by Bax deletion was associated with protection against mouse death from the GI syndrome, similar to that reported for SV129/C57BL/6 mice[1]. Autologous bone marrow transplantation (BMT) protected 100% of C57Bl/6$^{Bax+/+}$ and C57Bl/6$^{Bax-/-}$ mice exposed to 13 Gy TBI from BM death (FIG. 3c). Control animals exposed to these TBI doses but not receiving BMT succumbed to BM death with fully repaired (12 Gy) or near completely repaired (13 Gy) GI mucosa (Table 1). Table 1 shows that genetic inactivation of Bax or pharmacologic antagonism of ceramide by anti-ceramide antibody inhibits the lethal GI syndrome. Autopsies of total body irradiated C57BL/6 mice of Bax$^{+/+}$ or Bax$^{-/-}$ genotype and C57BL/6 mice administered anti-ceramide antibody or irrelevant IgM control revealed Bax and ceramide signaling are required for the lethal GI syndrome. BM and GI lethality was assessed by histopathologic examination of H&E stained, 5 μm sections of proximal jejunum and femur. GI lethality was characterized by complete denudation of villus and crypts, and BM lethality was characterized by depletion of hematopoietic elements from the BM cavity and massive hemorrhage. * denotes accelerated BM aplasia and mixed BM and GI death.

TABLE 1

Lethal Syndrome

| Genotype | TBI | BM | GI |
|---|---|---|---|
| C57BL/6$^{Bax+/+}$ | 12 Gy | 100% | — |
|  | 13 Gy | 100% | — |
|  | 14 Gy | 90% | 10% |
|  | 15 Gy | — | 100% |
| C57BL/6$^{Bax-/-}$ | 12 Gy | 100% | — |
|  | 13 Gy | 100% | — |
|  | 14 Gy | 100%* | — |
|  | 15 Gy | 100%* | — |
| C57BL/6 + IgM | 15 Gy | — | 100% |
| C57BL/6 + anti-ceramide | 15 Gy | 100% | — |

Figure 5A:
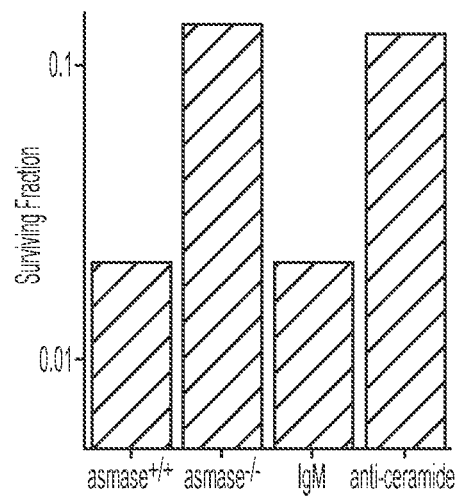
FIGS. 5A-5D. Sequestration of ceramide protects C57BL/6 intestinal mucosa against radiation-induced microvascular endothelial apoptosis, crypt stem cell death and lethal GI toxicity.
Figure 5B:
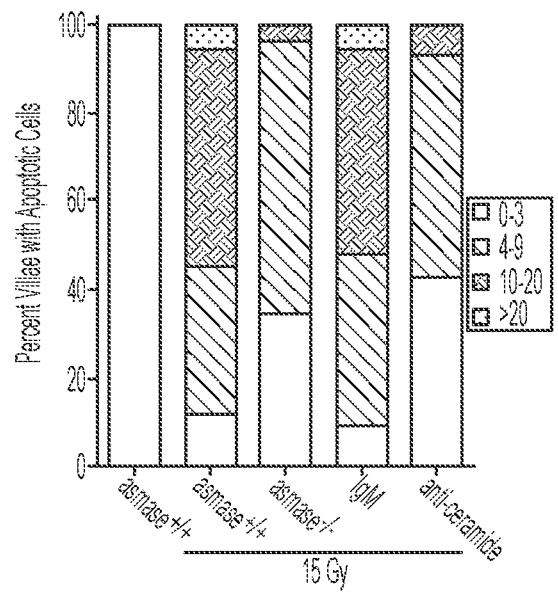
Figure 5C:
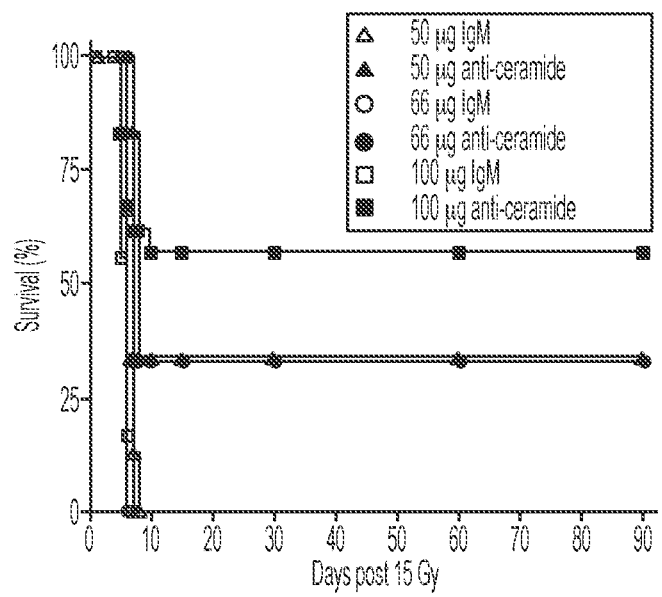

A switch to death from the GI syndrome occurred in C57Bl/6$^{Bax+/+}$ mice at 14 Gy TBI, with 90% of BMT-untreated mice succumbing to this mode of death at 7.7±0.8 days (FIG. 5c; Table 1). Thus, the C57BL/6 substrain harboring the Bax$^{-/-}$ genotype exhibited an approximate 1 Gy increase in GI radiosensitivity compared to previously reported data for a wild-type C57BL/6 mouse colony (F. Paris, Z. Fuks, A. Kang et al., Science 293 (5528), 293 (2001)). Bax deficiency protected from GI death after 14 Gy TBI (FIG. 5c, Table 1), with autopsies showing hyperplastic, chromophilic crypts covering most of the intestinal surface, indicative of advanced regeneration of the intestinal mucosa, and typical changes of BM death. These findings are consistent with the levels of crypt stem cell clonogen survival in C57Bl/6$^{Bax-/-}$ mice reported above (FIG. 3b) and the observation of a regenerating intestinal mucosa is probably associated with prolongation of survival of these mice (8.4±0.5 days; Table 1), which presumably enabled initiation of mucosal recovery. Autologous BMT permanently rescued 60% of C57Bl/6$^{Bax-/-}$ mice exposed to 14 Gy TBI (FIG. 3c; p<0.05), while the remaining animals failed engraftment and succumbed to bone marrow aplasia (Table 1). When the dose was escalated to 15 Gy TBI, C57Bl/6$^{Bax+/+}$ mice died at 5.5±0.4 days from autopsy-proven mixed GI and BM death (Table 1) and Bax deficiency failed to rescue the animals, despite the apparent availability of sufficient numbers of surviving crypts (FIG. 3b) as required for successful recovery of the GI mucosa. The latter phenomenon likely resulted from an accelerated development of BM aplasia and BM death, due to reasons uncertain, which occurred before mucosal regeneration became apparent. Consistent with this notion, autologous BMT into 15 Gy TBI-treated C57Bl/6$^{Bax-/-}$ mice extended mice survival to 9.0±0.0 days (FIG. 3c; p<0.05), and although the level of engraftment was insufficient to rescue the mice from BM matrix necrosis and complete depletion of hematopoietic elements (Table 1 and not shown), the intestinal mucosa revealed multiple areas of actively regenerating crypts. These data indicate that Bax deficiency mimics the protection against GI lethality conferred by ASMase deficiency. It should be noted that Bax and Bak deficiencies did not impact the p53 mediated epithelial apoptosis at crypt positions 4-5. Moreover, Bax and Bak do not overlap functionally in the intestinal microvascular system. Additional support can be found in J. A. Rotolo, et al, Int. J. Radiation Oncology Biol. Phys., Vol. 70, No. 3, 804-815(2008), incorporated herein by reference.

Certain embodiments of the invention are directed to methods for treating or preventing radiation damage or GI syndrome (and the other enumerated diseases that are discussed below) in a subject by administering an antisense nucleotide or siRNA that inhibits the endogenous expression of the target protein ASMase or Bak or Bax in the patient. Other embodiments are directed to methods to treat or prevent radiation disease or GI syndrome by administering imipramine in amounts that ameliorate one or more symptoms of the disease. A therapeutic amount of antisense that inhibits ASMase for example, or imipramine can be determined by routine experimentation as an amount that reduces ASMase activity or expression in a biological sample from a human (or mammalian) subject compared to pretreatment levels.

The respective antisense nucleotide is one wherein at least a portion of the antisense nucleotide, typically 8-50 consecutive nucleotides) is complementary to and specifically hybridizes with the gene or mRNA encoding the target ASMase, Bax or Bak. The GenBank accession number for ASMase is NP_000534, incorporated herein as SEQ ID NO: 1. The GenBank accession number for Bax is NP_004315.1, incorporated herein as SEQ ID NO: 2. The GenBank accession number for Bak is NP_001179.1, incorporated herein as SEQ ID NO: 3. As is described below, a person of skill in the art can design a variety of antisense nucleotides and siRNAs to disrupt either transcription or translation of the target gene or mRNA, respectively, to reduce expression of ASMase, Bax, or Bak. Antisense nucleic acids for use in this invention therapeutically to treat or prevent the enumerated diseases include cDNA, antisense DNA, antisense RNA, and small interfering RNA, that are sufficiently complementary to the target gene or mRNA encoding the target protein to permit specific hybridization to the respective gene or mRNA, thereby reducing expression of the target protein in the animal compared to pretreatment levels.

In particular embodiments the enumerated diseases are treated or prevented by administering a therapeutic amount of an antisense nucleic acid from 8-50 nucleotides in length that specifically hybridizes to SEQ ID NO. 2 which is the cDNA sequence for human ASMase Accession No. NM 000543; or SEQ ID NO. 4 which is the CDNA sequence for human Bax Accession No. NM 138761; or SEQ ID NO: 5 which is the cDNA sequence for human BAK Accession No. NM 001188. In another embodiment the antisense is directed to various regions of the respective genomic DNAs that would block transcription of the respective gene, ASMase SEQ ID NO. 7, Bax SEQ ID NO: 8, or Bak SEQ ID NO: 9. A patient could be treated with a combination of these antisense nucleic acids in a single preparation or in different preparationsadministered on the same or different days to reduce expression of ASMase (protein sequence SEQ ID NO. 1), or Bax (protein sequence SEQ ID NO.3); or Bak (protein sequence SEQ ID NO. 5). Alternatively, treatment could be achieved by administering the appropriate siRNA to reduce expression of one or more of the targeted proteins ASMase, Bax or Bak. More details regarding antisense technology are set forth below.

For the purpose of this invention, a therapeutically effective amount of a compound is an amount that achieves the desired biologic or therapeutic effect, namely an amount that prevents, reduces or ameliorates one or more symptoms of the enumerated diseases being treated or prevented. A starting point for determining an effective therapeutic amount of antisense or siRNA is an amount that reduces expression of the targeted protein ASMase, or Bax or Bak in a biological sample taken from a subject. The therapeutic amount of imipramine can be similarly determined.

Figure 4A:
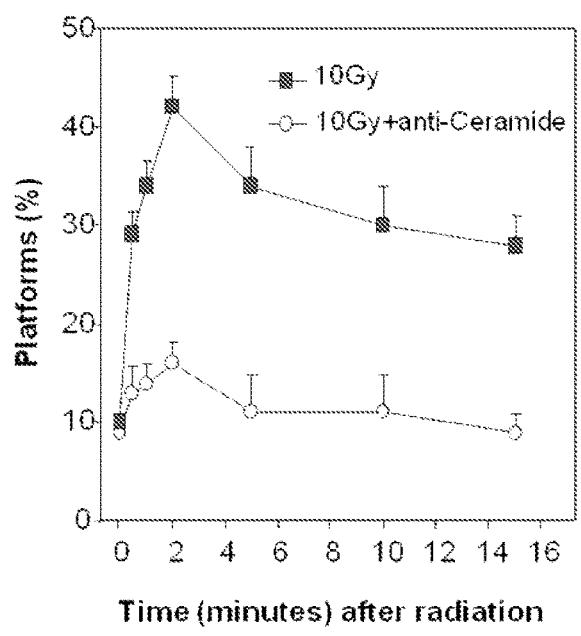
FIGS. 4A-4B. Neutralization of Ceramide Antagonizes Platform Generation, Attenuating Radiation-induced Apoptosis in vitro.
Figure 4B:
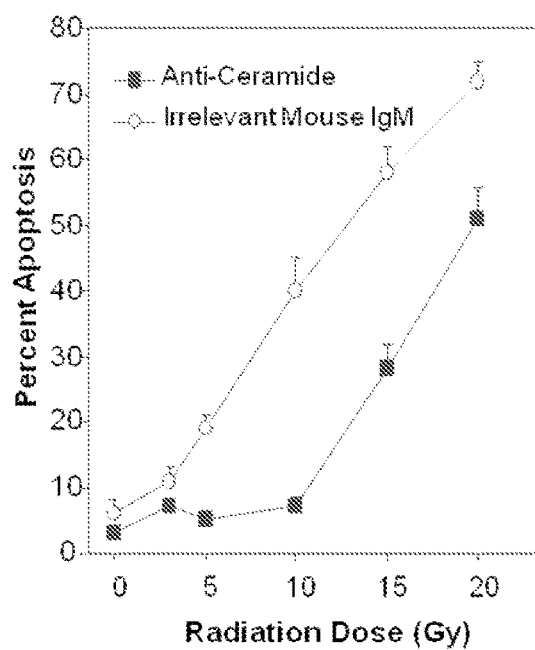

Treatment and Prevention of IR-Induced Diseases and GI Syndrome with Anti-Ceramide Antibodies We conducted in vitro studies in Jurkat T cells showing that sequestration of ceramide with anti-ceramide antibody inhibited ceramide-mediated raft clustering, thereby attenuating apoptosis and improving clonogenic survival (FIG. 4). To determine the in vivo effects of anti-ceramide on radiation-induced apoptosis, 100 μg the commercially sold mouse anti-ceramide antibody MID 15B4 or isotype control IgM was administered intravenously to C57BL/6 mice 30 min prior to 15 Gy TBI. Anti-ceramide infusion abrogated endothelial apoptosis 4 hrs post 15 Gy, decreasing the incidence of massive apoptosis (>10 apoptotic cells per villus) from 56.9% in IgM treated controls to 13.7% (FIGS. 5B and D), pharmacologically recapitulating the protection afforded by genetic inactivation of ASMase (14.9%). These findings showed that anti-ceramide-mediated protection of endothelium impacted GI stem cell lethality, and thereby enhance overall animal survival. Antagonism of endothelial apoptosis enhanced survival of crypt stem cell clonogens, evidenced by increased incidence of surviving crypts 3.5 days following 15 Gy irradiation. As anti-ceramide attenuated endothelial apoptosis, pharmacologically recapitulating the asmase$^{-/-}$ phenotype, we tested the impact on crypt survival. Pretreatment of C57BL/6 mice with anti-ceramide prior to 15 Gy TBI resulted in a crypt surviving fraction of 1.3×10−1, over 1 log of protection over the 9.3×10−3 surviving fraction exhibited by littermates treated with irrelevant IgM prior to 15 Gy TBI (FIG. 5A). Irrelevant IgM antibody did not impact crypt survival compared with untreated C57BL/6 controls. Anti-ceramide antibody increased crypt survival to similar levels as genetic inhibition of ASMase (1.2×10−1), demonstrating that pharmacologic inhibition of ceramide signaling mimics the protection afforded by genetic inactivation of ASMase on crypt clonogen lethality in vivo. It should be noted that Bax and Bak deficiencies did not impact the p53 mediated epithelial apoptosis at crypt positions 4-5. Moreover, Bax and Bak do not overlap functionally in the intestinal microvascular system. Additional support can be found in J. A. Rotolo, et al, Int. J. Radiation Oncology Biol. Phys., Vol. 70, No. 3, 804-815(2008), incorporated herein by reference.

Figure 5D:
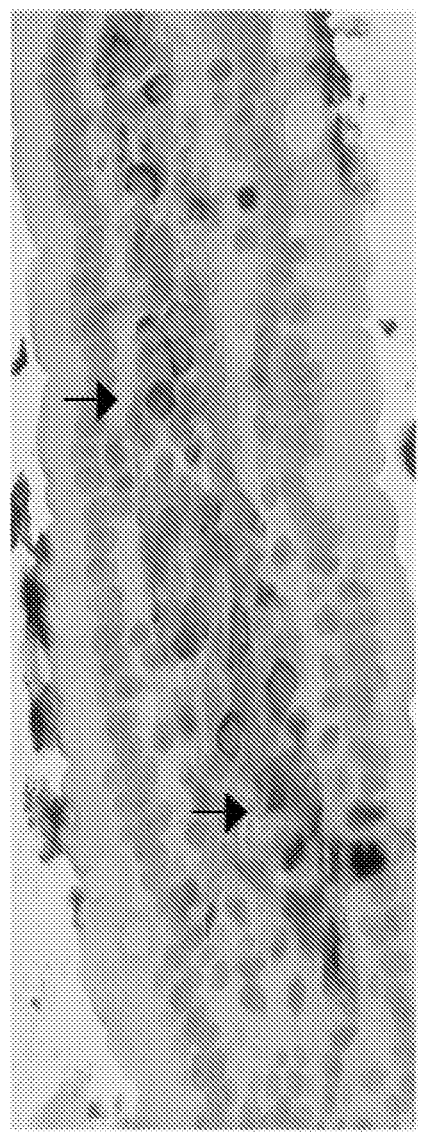
Figure 5D:
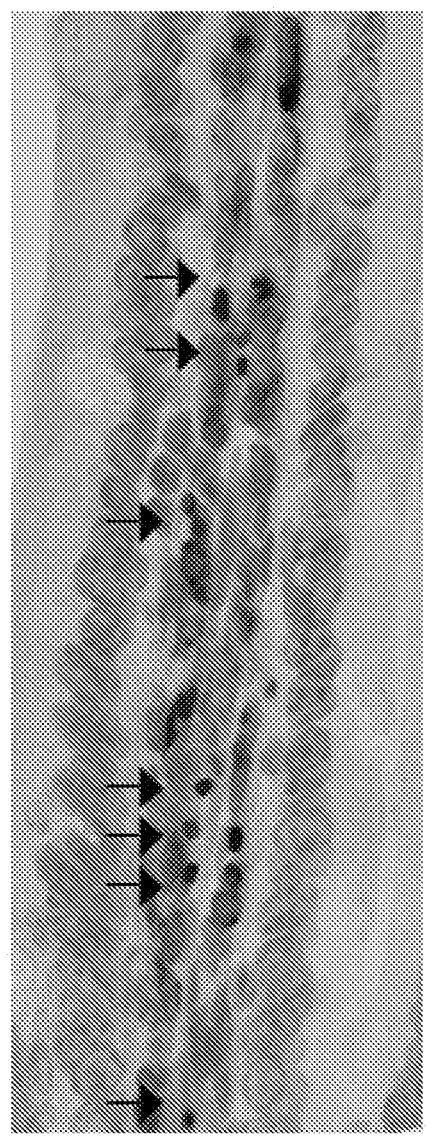

To assess whether anti-ceramide administration could recapitulate the asmase$^{-/-}$ phenotype and increase animal survival following 15 Gy, C57BL/6 mice were pretreated with 50-100 μg anti-ceramide antibody or irrelevant IgM control and subjected to 15 Gy TBI. Within 16 hrs of irradiation, mice were administered 3×10$^6$ autologous bone marrow cells intravenously. Consistent with previously published data, 15 Gy was 100% lethal in C57BL/6 control of IgM treated mice by day 7. Anti-ceramide antibody increased survival in a dose-dependent manner, with 100 μg anti-ceramide pretreatment resulting in 60% survival 120 days following irradiation (FIG. 5C). These findings correlate closely to the survival of asmase$^{-/-}$ mice administered autologous BMT following 15 Gy (F. Paris, Z. Fuks, A. Kang et al., Science 293 (5528), 293 (2001)). Autopsies revealed that mice receiving control IgM died with extensive intestinal damage, including completely denuded crypts and villi, with only partial damage to the bone marrow (not shown). These findings are consistent with death from the GI syndrome. Conversely, autopsies of mice that died following anti-ceramide pretreatment revealed typical characteristics of bone marrow death, including extensive hemorrhage and near complete depletion of hematopoietic elements (not shown). These mice exhibited intestinal mucosa in regenerative states, containing hyperplastic, chromophilic crypts covering most of the intestinal surface. FIG. 5D shows micrographs of small intestine obtained 4 hrs following 15 Gy-irradiation were stained by TUNEL. Apoptotic cells are indicated by brown-stained nuclei. Data (mean±SEM) were obtained from minimum 150 villi from two independent experiments. These data demonstrate that anti-ceramide antibody effectively antagonizes ceramide signaling in vivo, recapitulating the asmase$^{-/-}$ phenotype pharmacologically and protecting against radiation-induced disease and GI syndrome Based on this evidence for the role of extracellular ceramide in apoptosis, certain embodiments of the invention are directed to methods for treating or preventing radiation-induced disease and GI syndrome by administering a therapeutic amount of one or more anti-ceramide antibodies or a biologically active fragment thereof, preferably humanized forms. These antibodies can be polyclonal or monoclonal. In a preferred embodiment the anti-ceramide antibody is monoclonal 2A2 antibody or a biologically active fragment thereof, described below, preferably in humanized form. A new and effective monoclonal anti-ceramide antibody we discovered called 2A2 IgM is described in detail below. Previous work described above showed that statins (nystatin) also had beneficial effects in reducing apoptosis in in vitro models. Therefore certain other embodiments include administering a therapeutic amount of an anti-ceramide antibody or biologically active fragment thereof, and one or more statins, administered alone or in combination to treat or prevent GI syndrome. The therapeutic agents described herein for combination therapy can be administered on the same or on consecutive days.

Statins include any of a group of drugs that lower the amount of cholesterol and certain fats in the blood. Statins inhibit a key enzyme that helps make cholesterol. The statins are divided into two groups: fermentation-derived and synthetic. The statins include, in alphabetical order (brand names vary in different countries):

| Statin | Brand name | Derivation |
| --- | --- | --- |
| Atorvastatin | Lipitor, Torvast | Synthetic |
| Cerivastatin | Lipobay, Baycol. (Withdrawn from the market in August, 2001 due to risk of serious adverse effects) | Synthetic |
| Fluvastatin | Lescol, Lescol XL | Synthetic |
| Lovastatin | Mevacor, Altocor | Fermentation-derived |
| Mevastatin | — | Naturally-occurring compound. Found in red yeast rice. |
| Pitavastatin | Pravachol, Selektine, Lipostat | Fermentation-derived |
| Rosuvastatin | Crestor | Synthetic |
| Simvastatin | Zocor, Lipex | Fermentation-derived. (Simvastatin is a synthetic derivate of a fermentation product) |
| Simvastatin + Ezetimibe | Vytorin | Combination therapy |
| Lovastatin + Niacin extended-release | Advicor | Combination therapy |
| Atorvastatin + Amlodipine Besylate | Caduet | Combination therapy Cholesterol + Blood Pressure |

Figure 6:
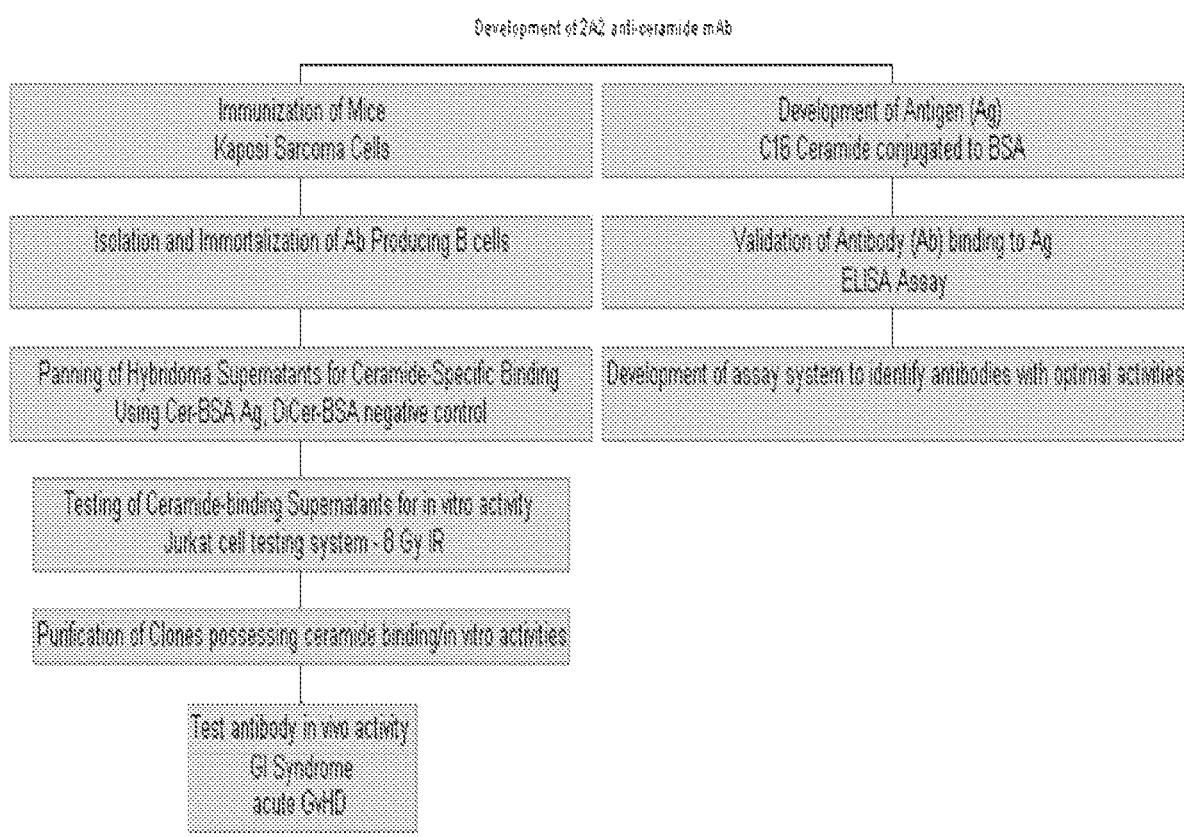
FIG. 6. Flow chart showing the strategy used to generate humanizable anti-ceramide monoclonal antibody.
Figure 7:
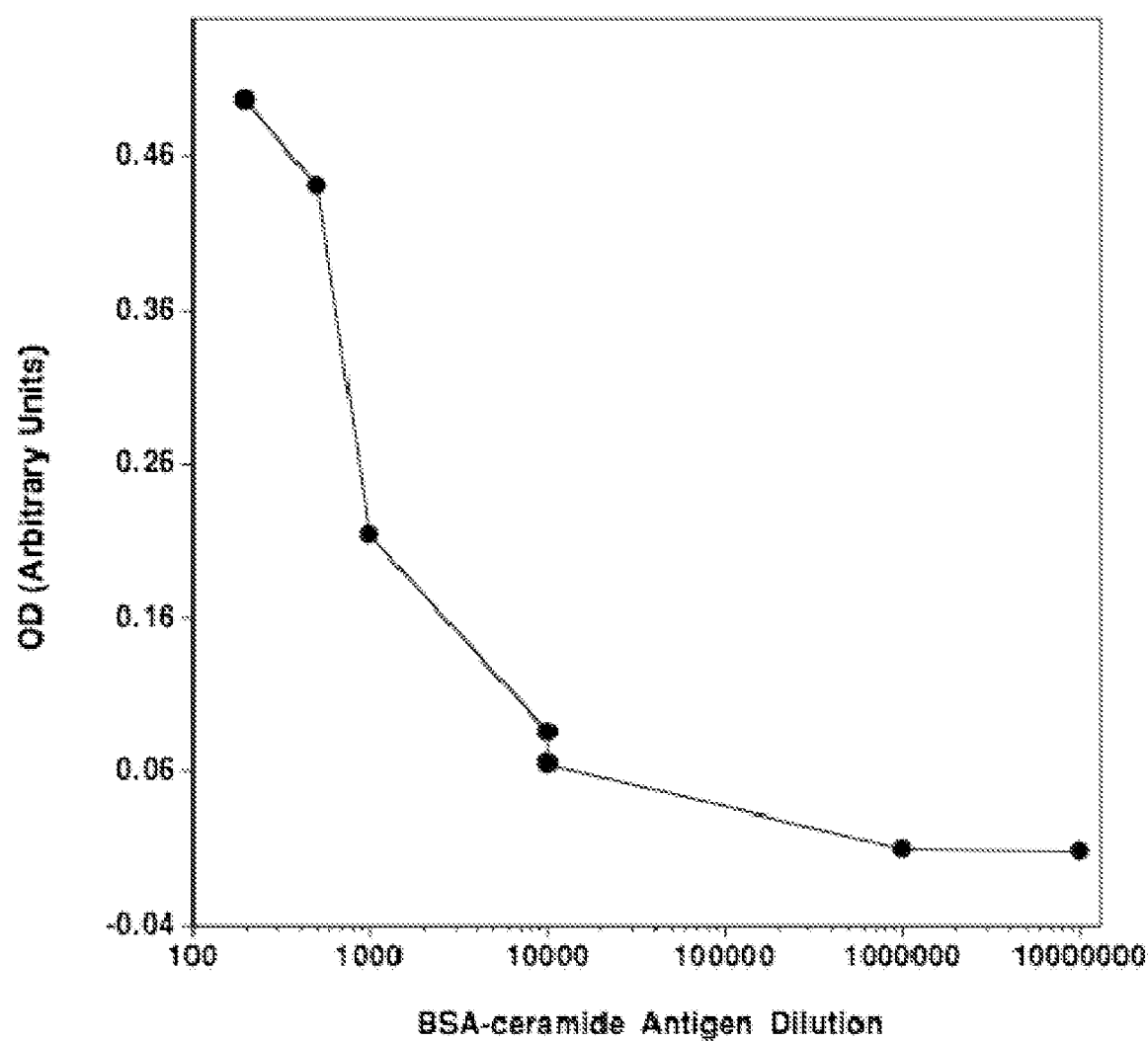
FIG. 7. Development of antigen (Ag), Validation of ELISA for Screening. (Inset) BSA-conjugated ceramide was generated by synthesizing BSA-conjugated $C_{16}$ fatty acid onto a sphingoid base. Validation of the Ag for antibody screening was performed by ELISA assay, in which decreasing amounts of Ag were fixed to a plate, and following blocking each well was incubated with anti-ceramide MID15B4 antibody (1:100) followed by horseradish peroxidase-conjugated anti-mouse IgM. OD was assessed following administration of (horseradish peroxidase) HRP substrate at 650 nm.
Figure 8:
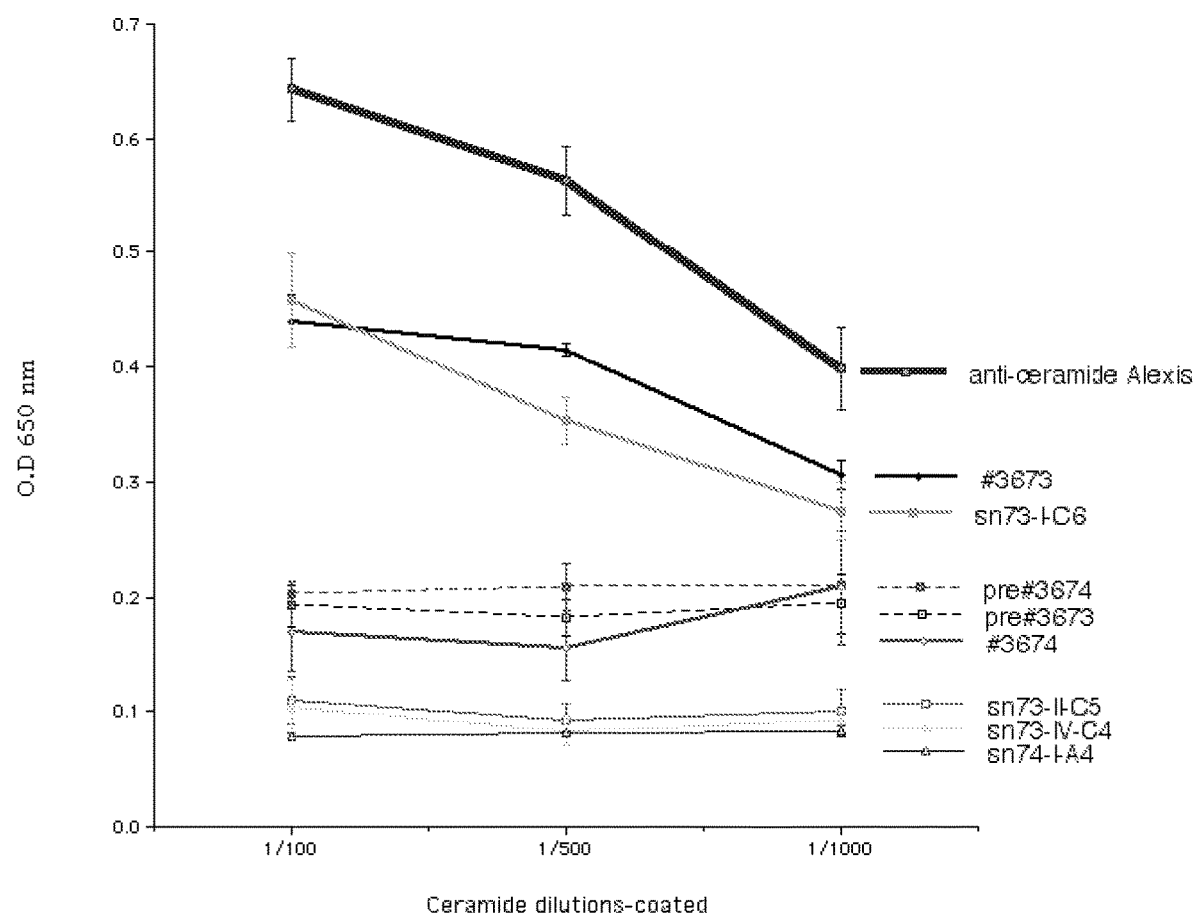
FIG. 8. BSA-ceramide ELISA identified enhanced binding activity in supernatant #3673 following immunization with Kaposi sarcoma cells. Binding of plasma samples obtained from immunized mice by ELISA at 1:100 dilution identified higher binding of ceramide by sample #3673 vs. #3674. Binding activity remained following immortalization of antibody producing B cells (sn73-I-C6), enabling the isolation of monoclonal 2A2 IgM with anti-ceramide binding activity (not shown).

LDL-lowering potency varies between agents. Cerivastatin is the most potent, followed by (in order of decreasing potency) rosuvastatin, atorvastatin, simvastatin, lovastatin, pravastatin, 2A2 Anti-Ceramide Monoclonal IgM Antibody A flow chart of the strategy used to generate novel anti-ceramide antibodies with potent in vivo activity is shown in FIG. 6. In order to make the antibody, we first needed to develop an antigen that was immunogenic enough to generate a strong antibody response from an inoculated host. BSA-conjugated ceramide was generated by synthesizing BSA-conjugated $C_{16}$ fatty acid onto a sphingoid base. FIG. 7) inset. Validation of the Antigen for antibody screening was performed by ELISA assay, in which decreasing amounts of Antigen were fixed to a plate. After blocking each well, the plate was then incubated with anti-ceramide MID15B4 antibody (1:100) commercially available from Axxora LLC, San Diego Calif. followed by horseradish peroxidase-conjugated anti-mouse IgM. OD was assessed following administration of HRP substrate at 650 nm. The BSA-ceramide ELISA identified enhanced binding activity in supernatant #3673 following immunization with Kaposi sarcoma cells. FIG. 8. Binding of plasma samples obtained from immunized mice by ELISA at 1:100 dilution identified higher binding of ceramide by sample #3673 vs. #3674. Binding activity remained following immortalization of antibody producing B cells (sn73-I-C6), enabling the isolation of monoclonal 2A2 IgM with anti-ceramide binding activity (not shown). Karposi immunization was intended to generate a strong immune response which would result in generation of a panel of antibody-producing B cells. The antibody-containing supernatant from the hybridomas generated from these B cells was then screened against the BSA-ceramide ELISA. Supernatants that tested positive in the assay were isolated, eventually resulting in purification of clone 2A2. More details are set forth in Example 4.

Figure 9:
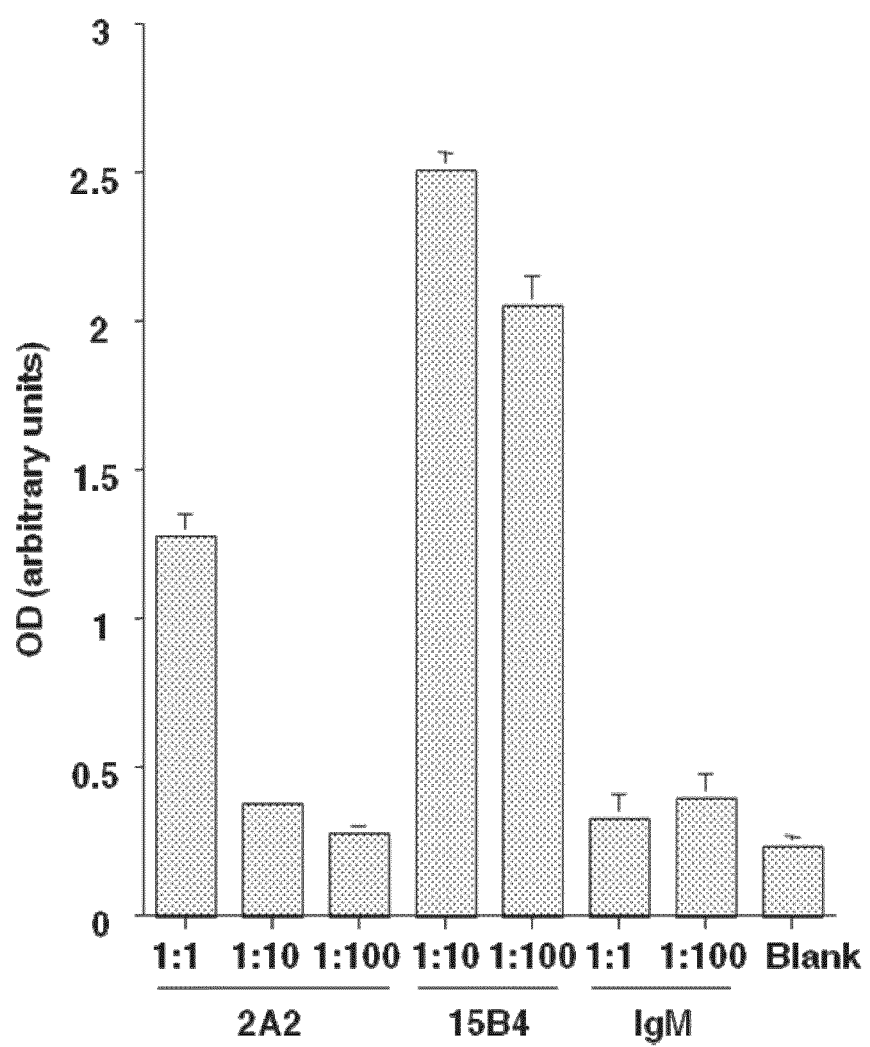
FIG. 9. Purified monoclonal 2A2 antibody binds to BSA-ceramide. Elisa revealed that 2A2 mouse monoclonal IgM binds to BSA-ceramide. Elisa shows significantly more binding capacity of 2A2 vs. control IgM, performed as in FIG. 7. 2A2 binds ceramide 5-10× less efficiently than MID15B4 mouse IgM.

Purified monoclonal 2A2 antibody was isolated from supernatant #3673. Elisa revealed that the 2A2 mouse monoclonal IgM bound to BSA-ceramide. FIG. 9. Elisa showed significantly more binding capacity of 2A2 vs. control IgM. We show that the 2A2 antibody works in vivo and we were able to humanize it for clinical use. Methods for humanizing the antibody and others are set forth in Example 1.

Figure 10:
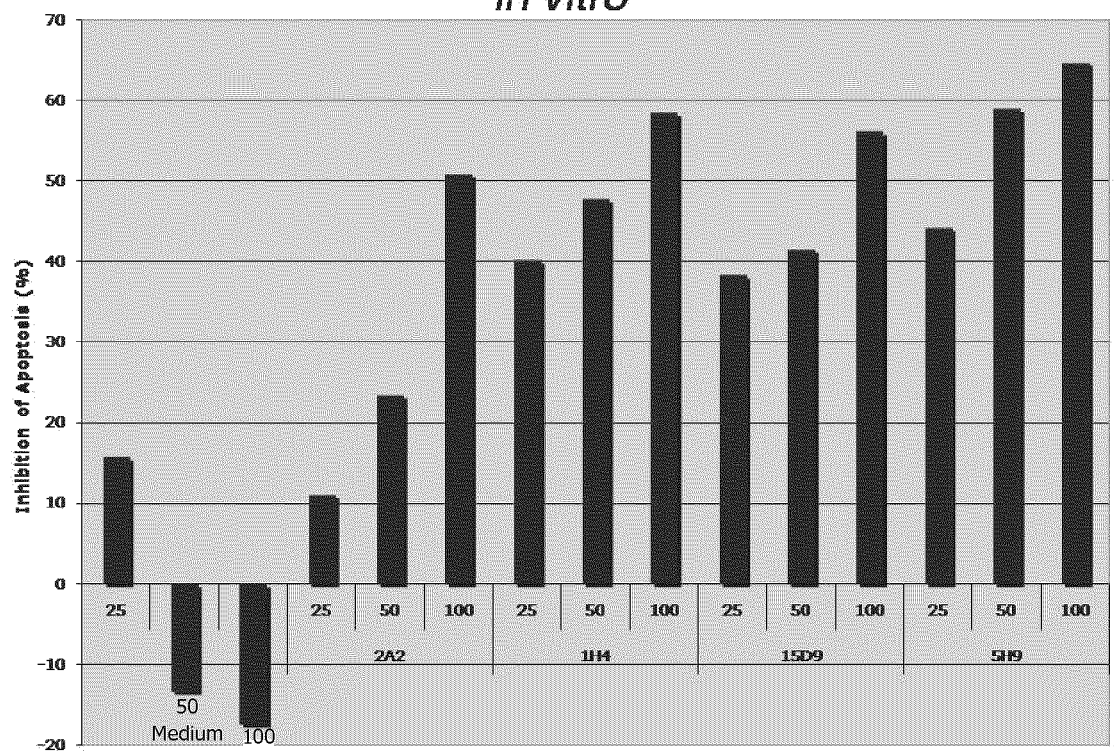
FIG. 10. 2A2 antagonizes radiation-induced apoptosis in vitro. Pre-incubation of Jurkat T cells with anti-ceramide 2A2 (0-100 microgram/ml) 15 min prior to 8 Gy IR. Apoptosis was quantified in Jurkat cells by nuclear morphologic analysis following Hoeschst bisbenzimide staining with or without preincubation with anti-ceramide antibody. Data are derived from minimum 150 cells obtained from three independent experiments FIGS. 11A-11B. 2A2 Enhanced Crypt Survival Following 15 Gy in vivo.

Consistent with our earlier observations in vitro with commercial antibodies, purified 2A2 antibody antagonized radiation-induced apoptosis in vitro. Preincubation of Jurkat cells with 2A2 monoclonal anti-ceramide antibody (25-100 micrograms/mL) inhibited 8 Gy-induced apoptosis. FIG. 10; quantified as in FIG. 4B. Calculation of apoptosis inhibition was performed relative to the mean apoptosis of untreated Jurkat cells prior to 8 Gy. Other anti-ceramide antibodies 1H4, 15D9 and 5H9, generated by immunization of mice with $C_{16}$ ceramide, can be humanized using techniques known in the art, and come within the scope of this invention for treatment or prevention of GI syndrome, and also GvHD, autoimmune diseases and inflammation which are discussed below.

Figure 11A:
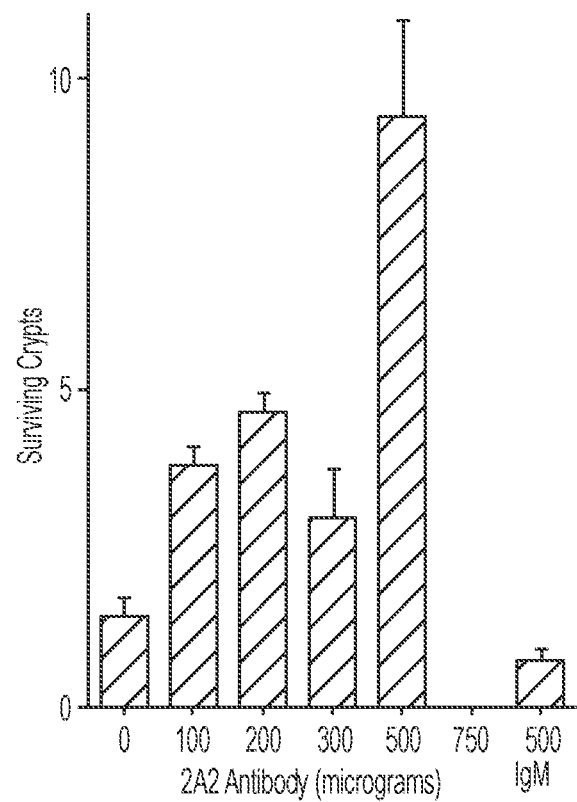
FIG. 11A: Pretreatment of C57BL/6 mice with increasing doses of 2A2 anti-ceramide (0-750 micrograms) improves crypt survival 3.5 d following 15 Gy TBI.
Figure 11B:
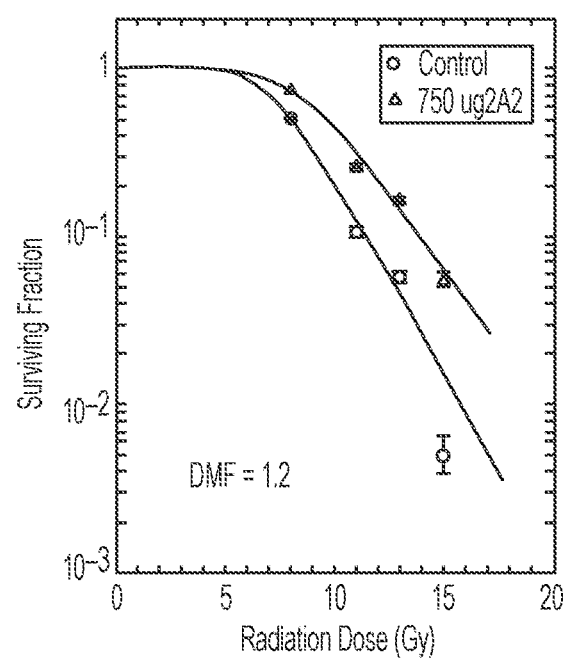
FIG. 11B: 2A2 anti-ceramide antibody increases crypt survival following 8-15 Gy total body irradiation by a dose-modifying factor (DMF) of 1.2 (in previous studies, ASMase deficiency increased crypt survival by a DMF of 1.2 in C57BL/6 mice). Crypt survival was determined as in FIG. 5C.
Figure 12A:
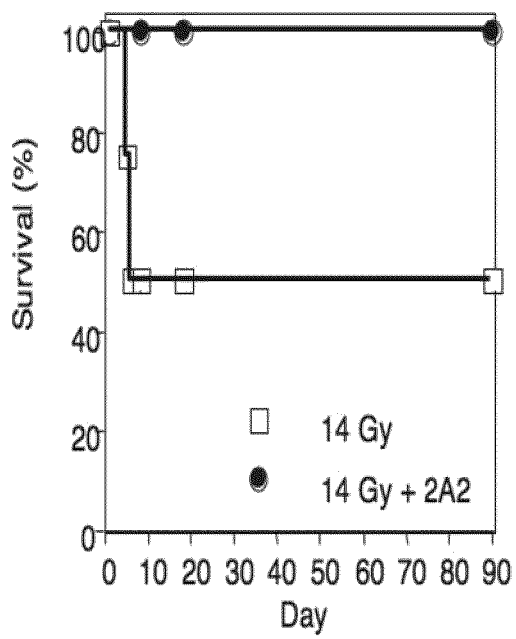
FIGS. 12A-12D. 2A2 antibody improves survival of C57BL/6 mice exposed to 14-17 Gy single-dose radiation. C57BL/6 mice were irradiated with 14, 15, 16, or 17 Gy TBI (as shown in FIGS. 12A, 12B, 12C, and 12D respectively) with or without 750 micrograms 2A2 15 min prior to IR. Mice were infused with 3×10$^6$ autologous bone marrow cells within 16 hour of IR. Survival was monitored and expressed via Kaplan-Meier parameters. Statistical significance (P<0.05) was achieved at each dose.
Figure 12B:
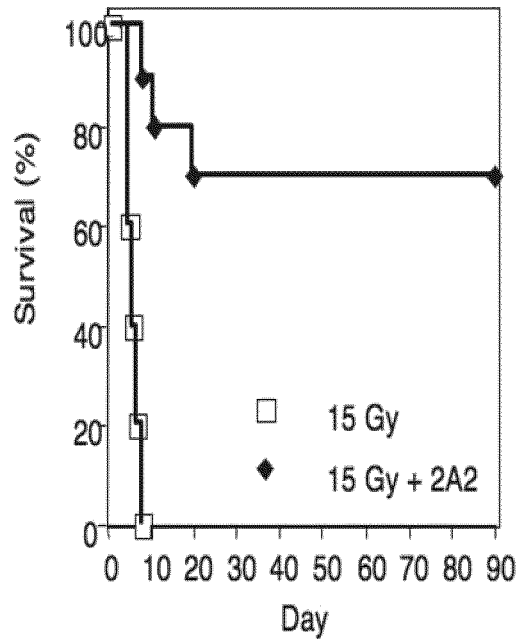
Figure 12C:
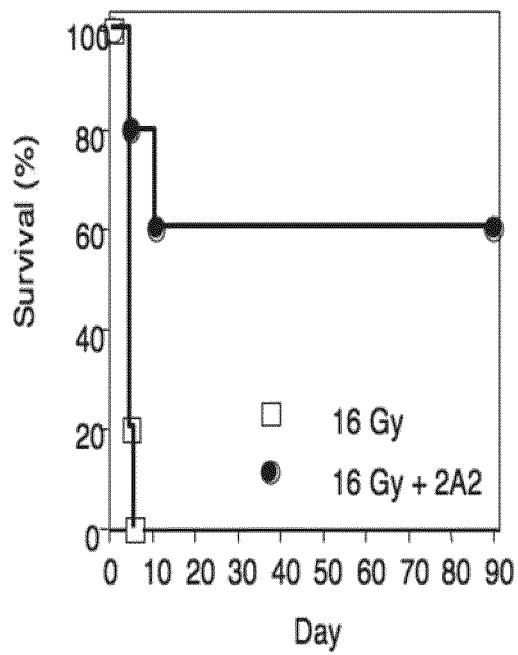
Figure 12D:
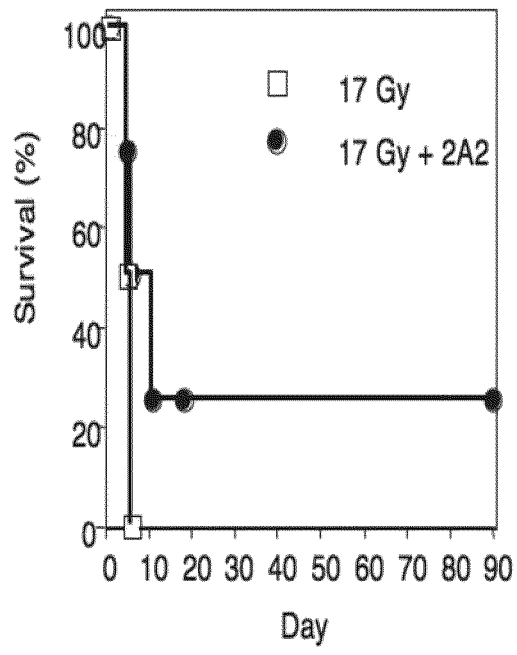

In the next series of experiments we showed that 2A2 enhanced crypt survival following 15 Gy in vivo. Pretreatment of C57BL/6 mice with increasing doses of 2A2 anti-ceramide (0-750 micrograms) improved crypt survival at the critical 3.5 day time point following 15 Gy TBI. FIG. 11(A). 2A2 anti-ceramide antibody increased crypt survival following 8-15 Gy total body irradiation by a dose-modifying factor (DMF) of 1.2. FIG. 11(B). Crypt survival was determined as in FIG. 5C. In our animal experiments we used 750 micrograms of antibody per 35 gram mouse. The location of ceramide on the surface of activated T cells is particularly important for treating or preventing any of the enumerated diseases using antibody therapy because this target protein is accessible to the antibodies.

In other experiments we discovered that anti 2A2 antibody also improved survival of C57BL/6 mice exposed to 14-17 Gy single-dose radiation. FIG. 12. C57BL/6 mice were irradiated with 14-17 Gy TBI with or without 750 micrograms 2A2 15 min prior to IR. Mice were infused with $3 \times 10^6$ autologous bone marrow cells within 16 hour of IR. Survival was monitored and expressed via Kaplan-Meier parameters. Statistical significance ($P<0.05$) was achieved at each dose.

Over a range of exposures, we found that 2A2 antibody attenuated radiation-induced GI death in vivo, recapitulating the asmase$^{-/-}$ phenotype. Necropsy results of mice sacrificed when moribund from survival studies performed in FIG. 13. GI death was assessed when proximal jejunum specimen appear >90% denuded of crypt-villi units and crypt regeneration is absent. Bone marrow (BM) death was assessed when decalcified femur sections reveal depletion of hematopoietic elements and massive hemorrhage.

These results support embodiments of the present invention directed to the 2A2 antibody itself, or fragment or variant thereof, preferably in humanized form. In another preferred embodiment the human 2A2 antibody, or fragment thereof is administered in a therapeutically effective amount to treat or prevent radiation damage or GI syndrome. Where antibody is used herein, it is also meant to include antibody fragments or variants as described below. Certain other embodiments are directed to a composition comprising an anti-ceramide antibody, preferably humanized, more preferably 2A2, and a statin in an amount that decreases circulating cholesterol levels thereby increasing the efficacy of the anti-ceramide antibody. Another embodiment is directed to treating or preventing radiation damage or GI syndrome by administering imipramine, and ASMase inhibitor presently used as an antipsychotic agent, either alone or in combination with anti-ceramide antibodies and/or statins. Another embodiment is a composition that includes the 2A2 antibody and imipramine or antisense or siRNA that targets ASMase or Bak.

Routine experimentation will determine the therapeutically effective amount of humanized monoclonal anti-ceramide antibody to use. The amount of anti-ceramide antibody to be administered therapeutically ranges from about 1 ug to 100 ug/ml. This amount typically varies and can be an amount sufficient to achieve serum therapeutic agent levels typically of between about 1 microgram per milliliter and about 10 micrograms per milliliter in the subject. In the context of the present invention, anti-ceramide antibodies are a type of neutralizing antibody that prevents ceramide from blocking apoptosis.

As will be described below, we also discovered that 2A2 antibody improved survival after BMT by reducing GvHD and reduced the typical cytokine storm seen with GvHD.

Figure 25:
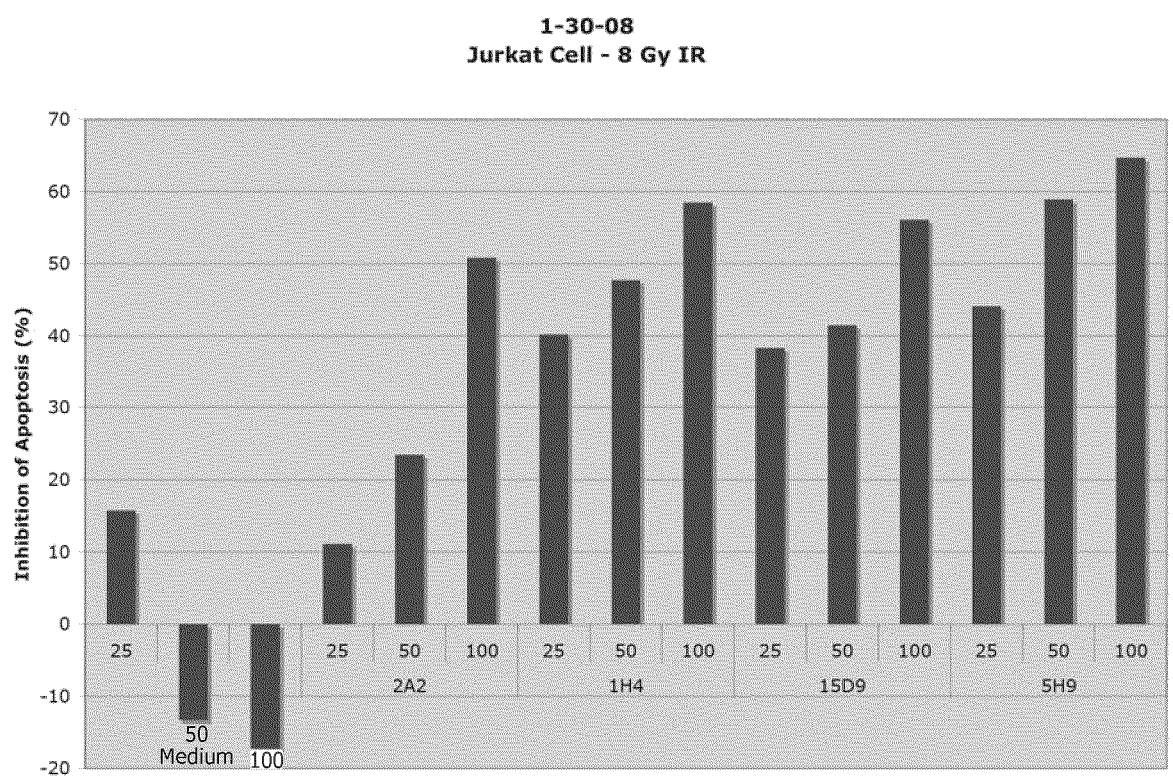

We discovered other monoclonal antibodies made in mice that were immunized with BSA-ceramide that when screened in a Jurkat cell apoptosis inhibition assay and showed protective effects that were dose dependent and comparable to 2A2. The isotypes of the three antibodies have been established. 15D9 mAb is IgM, kappa. 1H4 and 5H9 mAbs are mIgG3, kappa. FIG. 25.

Certain embodiments of the invention are directed to these monoclonal antibodies 15D9, 1H4 and 5H9, and to fragments or variants thereof, preferably humanized for therapeutic use to treat radiation induced diseases or GI syndrome, and as will be shown below also GvHD, other autoimmune diseases and inflammation. Other embodiments are directed to pharmaceutical compositions that include these monoclonal antibodies, fragments or variants, preferably in humanized form, and optional also imipramine or statins or both.

One of the discoveries we made is that immunizing the host mice with Karposi Sarcoma cells as described in Example 4, generated effective anti-ceramide monoclonal antibodies with dramatic therapeutic effects as shown for example with the 2A2 antibody. We chose KS cells because for immunization because they recapitulate activated endothelium which we have shown is ceramide-rich. Because we immunized with activated cells and not just with a pure ceramide antigen, the monoclonals we generated may cross react with other proteins besides ceramide. By cross react in this application is meant that the monoclonals may react with other proteins or protein complexes besides ceramide. For example the epitope on ceramide that these monoclonals react with (i.e. have affinity for) may be shared with other cell surface proteins. Alternatively other proteins may have a similar conformation at the antigenic site or the epitope may be part of a complex that displays the ceramide. Therefore certain other embodiments of the invention are directed broadly to monoclonal antibodies that cross-react with ceramide, wherein the antibodies are obtained by immunizing the host with whole cells. Humanized monoclonals including fragments are a preferred embodiment. The immunoglobulin subtype can be any subtype, IgG, IgM are preferred but also IgA, IgE etc. may be effective.

Treatment and Prevention of Graft-Vs.-Host Disease and Autoimmune Disorders

The results presented below show for the first time that ASMase-generated ceramide is required for GVHD, therefore certain embodiments are directed to pharmacological methods to treat or prevent GVHD by blocking ASMase (for example with imipramine or with antisense nucleic acids) or inactivate this cell surface ceramide (for example with anti-ceramide antibodies).

Figure 14:
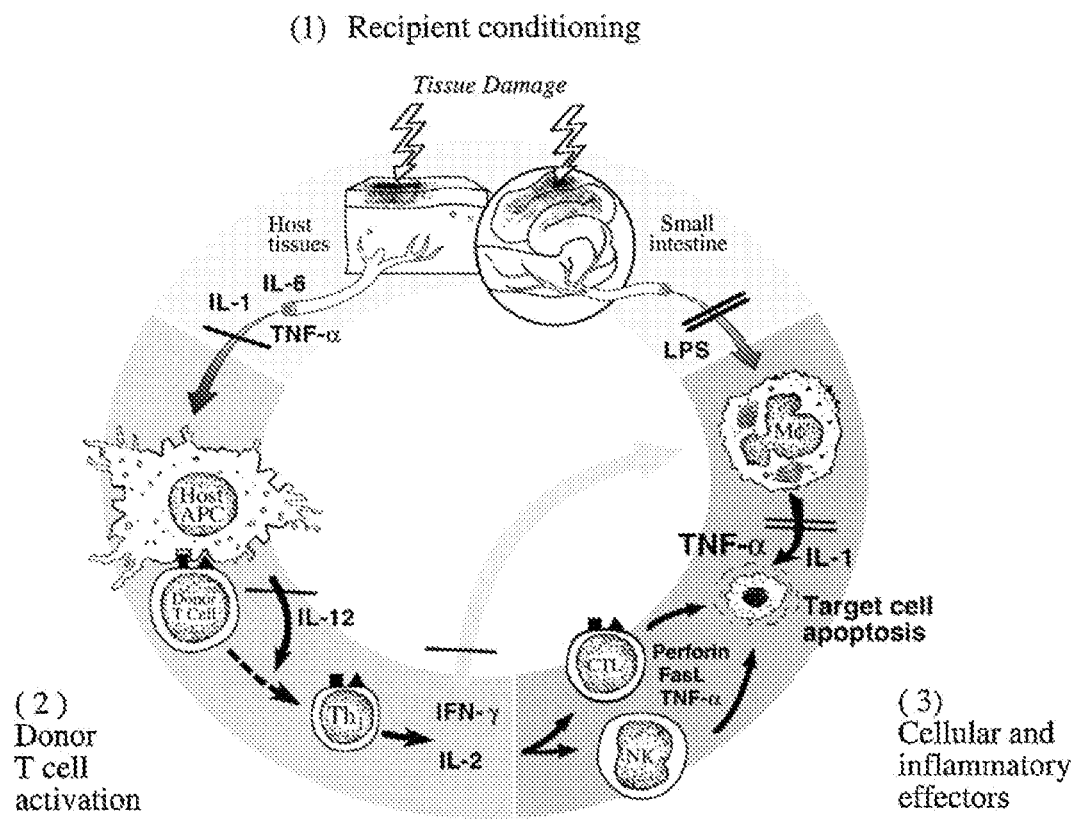
FIG. 14. A cartoon illustrating the immunopathophysiology of acute GvHD.

Autoimmune disorders are sustained adaptive immune responses directed against self antigens. T cells recognize self antigens as foreign due to incompatibilities between T cell and tissue major histocompatibility complex (MHC) molecules and/or minor histocompatibilty antigens (mHAGs), cell surface molecules expressed on most cell types. Activated T cells directed against self antigens inflict tissue damage and chronic inflammation directly (via cytotoxic T cells, CTLs) or indirectly (via antibody generation by T cell help to self-reactive B cells). Acute graft-versus-host disease (GvHD), the primary complication of hematopoietic stem cell transplantation, is a unique autoimmune-like disorder arising from the differentiation and activation of alloreactive donor T cells infused into an immunoablated host. In acute GvHD, recognition of alloantigens (major or minor mismatched) of the host by donor T cells initiates an adaptive immune response including incipient damage to host tissue and Type I cytokine (IFN-γ and IL-2) generation. This results in CTL clonal expansion and activation, that along with a developing macrophage-dependent "cytokine storm" comprised of inflammatory cytokines (TNF-α and IL-1β) (D. A. Wall and K. C. Sheehan, *Transplantation* 57 (2), 273 (1994); G. R. Hill, W. Krenger, and J. L. Ferrara, *Cytokines Cell Mol Ther* 3 (4), 257 (1997); J. L. Ferrara, Bone Marrow Transplant 21 Suppl 3, S13 (1998), induces apoptosis in a select set of target cells (A. C. Gilliam, D. Whitaker-Menezes, R. Korngold et al., *J Invest Dermatol* 107 (3), 377 (1996)), and consequent damage to associated target organs (liver, intestines and skin) D. A. Wall, supra; G. F. Murphy, D. Whitaker, J. Sprent et al., *Am J Pathol* 138 (4), 983 (1991)). Common symptoms of acute GvHD include severe weight loss, diarrhea, liver disease, rash and jaundice. FIG. 14 is a cartoon illustrating the immunopathology of GvHD.

High dose chemotherapy and radiation used in the treatment of many types of leukemia and lymphomas additionally kill rapidly dividing bone marrow cells stem cells, resulting in immunoablation and necessitating reconstitution of haematopoietic elements. Bone marrow transplantation (BMT) is a common and effective therapy for immune reconstitution in these patients, as well as treatment for immune disorders including aplastic anemia and severe combined immunodeficiency, in which infusion of bone marrow stem cells can correct deficiencies in red blood, T and/or B cells. GvHD is the major complication associated with BMT, occurring in 30% of MHC matched, 50% of single MHC disparate and 70% of double MHC disparate BMTs from related donors, and even higher when a non-related donor is used[86]. Despite extensive research, there is no good treatment. Acute GvHD typically develops within 3 months of BMT, during which specific organs including the gut, skin and liver are targeted by cytotoxic T cells. Until now, the clinically relevant strategies available to control GvHD are limited to T cell depletion from the allograft or non-specific immunosuppression aimed to control donor T cell expansion and activation, approaches that increase the likelihood of infection or neoplastic relapse in already immunocompromised patients.

Pharmacologic and genetic tools have enabled identification of several key mediators of CTL-induced apoptotic cell death at the cellular level. Liver, intestinal and skin apoptosis during acute GvHD is primarily mediated via CTL attack of host tissue via Fas-Fas ligand (FasL) (H. Kuwahara, Y. Tani, Y. Ogawa et al., *Clin Immunol* 99 (3), 340 (2001); C. Schmaltz, O. Alpdogan, K. J. Horndasch et al., *Blood* 97 (9), 2886 (2001); K. Hattori, T. Hirano, H. Miyajima et al., *Blood* 91 (11), 4051 (1998)) and TNF-TNFR pathways, with minimal contribution from perforin/granzyme-mediated cell lysis. Inhibition of TNF-superfamily receptor signaling largely attenuated acute GvHD-associated mortality in major and minor mismatched models of murine allogeneic BMT, either by genetic inactivation of donor T cell Fas ligand or TNF-α, or antibody-mediated neutralization of their cognate receptors CD95/Fas and TNFR, respectively. These studies established an essential role for death receptor signaling in donor CTL function in the pathogenesis of acute GvHD, and suggested that promiscuous inhibition of TNF-superfamily signaling might provide potent protection from GvH-associated pathology.

A number of recent studies identify a role for the sphingomyelin pathway and its second messenger ceramide in autoimmune, liver and GI toxicities. Genetic inactivation of ASMase abrogates autoimmune mouse models of phytohemagglutin (PHA)-induced Fas-dependent autoimmune hepatitis, during which induction of FasL on lymphocytes results in selective killing of hepatocytes expressing Fas, and activation of the HIV receptor gp120 by anti-CD4 antibody, in which depletion of CD4$^+$ T cells occurs due to upregulation of Fas and FasL on these cells. Further, evidence indicates that ceramide generation on the exoplasmic leaflet of the cell membrane occurs rapidly in the course of ischemia-reperfusion injury L. Llacuna, M. Mari, C. Garcia-Ruiz et al., *Hepatology* 44 (3), 561 (2006)), and TNF-induced hepatocyte apoptosis that leads to cirrhosis[93] and radiation-induced GI toxicity that has already been discussed using standardized animal models for these disease entities.

Acute GvHD, the primary complication of hematopoietic stem cell transplantation, is a well-defined autoimmune-like disorder mediated by donor cytolytic T cell attack on host tissue. To evaluate the contribution of target cell ASMase and ceramide in CTL-mediated tissue injury and mortality during acute GvHD, a minor histocompatability-incompatible allogeneic BM transplantation model of LP/J donor (H-2$^b$) into C57BL/6 recipient (H-2$^b$) was selected. Lethally-irradiated C57BL/6 hosts of asmase$^{+/+}$ or asmase$^{-/-}$ background received 5×10$^6$ T-cell depleted (TCD) LP/J BM cells, and GvHD was induced by the addition of 3×10$^6$ LP/J donor splenic T cells to the allograft. Transplantation of donor LP/J BM and T cells induced the development of GvHD in all recipients, albeit with reduced effect in asmase$^{-/-}$ recipients as determined by Kaplan-Meier survival (FIG. 15A) and clinical GvHD score (FIG. 15B) curves. GvHD survival was increased from 28.6% in asmase$^{+/+}$ recipients of BM and T cells to 84.6% in asmase$^{-/-}$ recipients (p<0.005), and was accompanied by consistently lower clinical scoring through day 90 in the asmase$^{-/-}$ recipients (FIG. 15B and not shown), indicative of attenuated GvHD in asmase$^{-/-}$ recipients. These results identify a role for ASMase in acute GvHD-induced mortality in a minor MHC-disparate allogeneic BMT model.

GvH-induced mortality is associated with injury to select organs including the ileum, liver and skin. Example 2 describes experiments showing that ASMase is required for GvHD target organ injury and apoptosis. Experiments in Example 2 show that ASMase deficiency largely protected GvHD-associated organ damage, decreasing scoring to 10.2±0.5 and 7±0.1 in liver and small intestines, respectively (Table 1, p<0.005 each for liver and intestine vs. asmase$^{+/+}$ littermates). ASMase deficiency also protected hosts from cutaneous keratinocyte apoptosis following minor antigen-mismatched allogeneic BMT. Further GvHD-associated organ injury was shown to be associated with prominent intestine and skin apoptosis. These data identify a significant attenuation of GvHD-associated target organ damage and apoptosis, closely correlating with protection against GvHD morbidity and mortality, in asmase$^{-/-}$ hosts compared to wild type littermates across both minor and major antigen disparities.

Additional experiments described in Example 3 show that ASMase deficiency attenuated the cytokine storm associated with GvHD and inflammation generally, thus protecting the host from inflammation. The experiments showed that ASMase inactivation attenuated Th1/Th2 cytokine profile and CD8$^+$ T cell proliferation in acute GvHD in recipients of allogeneic BM and T cells. Our data showed deficient in vivo CD8$^+$ CTL proliferation in asmase$^{-/-}$ hosts, and biologically-relevant consequences to the attenuation of serum proinflammatory cytokine levels in these BMT recipients having GvHD. Thus, the in vivo data confirm a role for ASMase in GvH-associated morbidity, mortality and target organ damage. The impact of host ASMase deficiency affects GvHD pathophysiology primarily by to altering systemic factors (i.e. cytokines, number of circulating T cells) and not by inactivation of T cell killing.

Administration of Anti-Ceramide Antibody Prevents GvHD

Figure 16A:
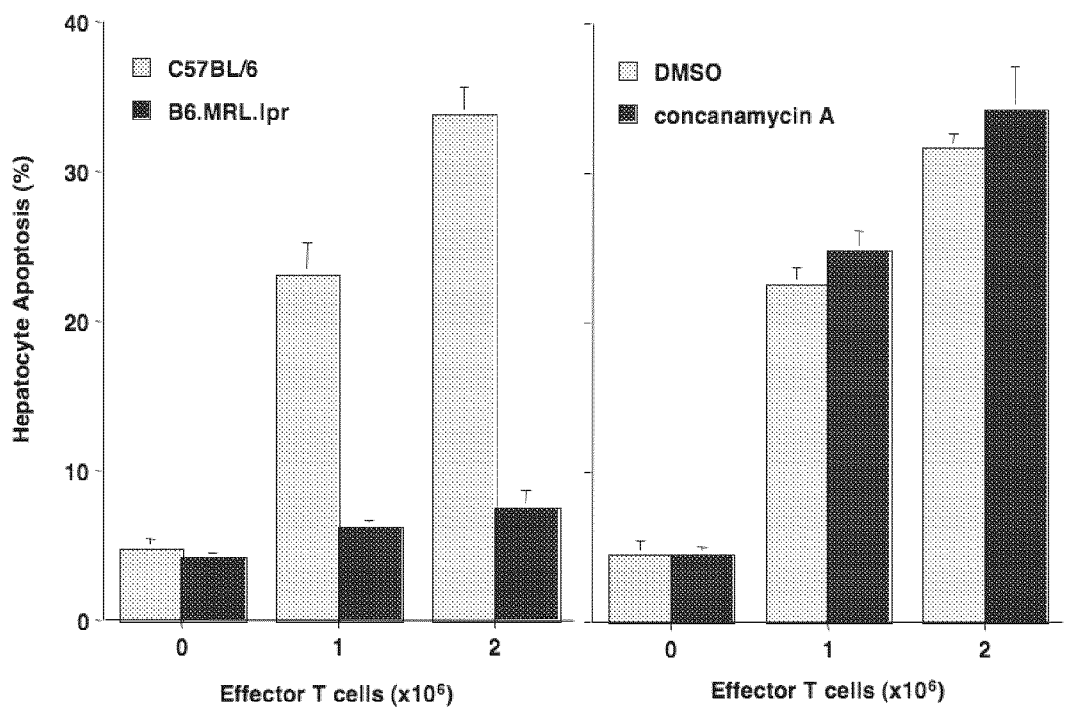
FIGS. 16A-16F. In vivo activated allogeneic CTLs require target hepatocyte ASMase for efficient killing ex vivo. Hepatocytes, isolated as described in Example 1, were coincubated with splenic T cells harvested from lethally-irradiated wild type C57BL/6 recipients 10-14 days following transplantation of LP BM+T cells.
Figure 16B:
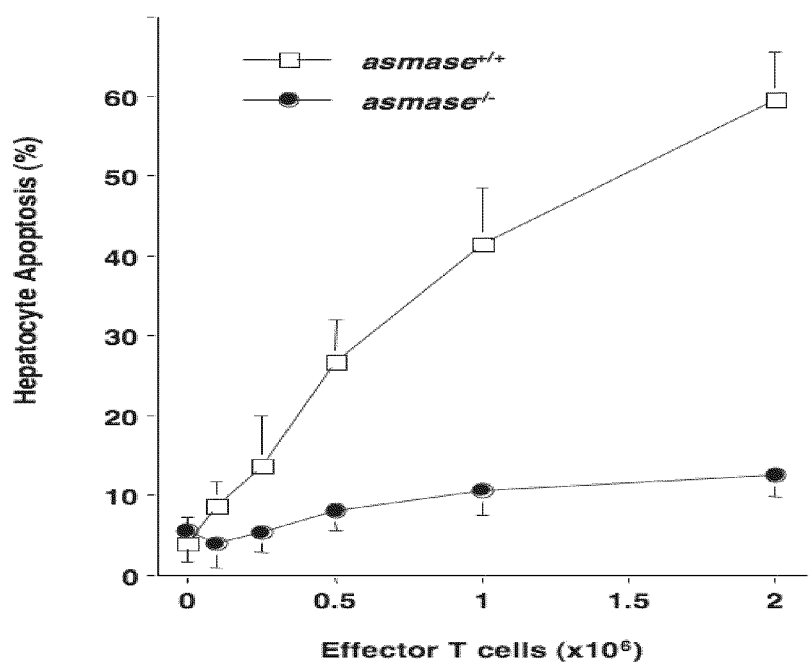

To assess whether ceramide-mediated raft clustering into membrane platforms is an essential component of cytolytic T cell (CTL)-induced apoptosis of hepatocytes, we blocked raft clustering pharmacologically and examined the impact on alloactivated CTL-induced hepatocyte apoptosis in vitro. To investigate whether ASMase deficiency renders target cells directly resistant to CTL-induced apoptosis, GvHD-mediated target cell lysis was deconstructed in a 2-cell ex vivo model using alloactivated splenic CTL effectors freshly-isolated from mice exhibiting active GvHD and naive C57BL/6 hepatocytes. Hepatocytes were chosen as target cells in this assay because they are a critical target for GvHD and utilize the sphingomyelin pathway for apoptosis. Under the conditions of our assay, 0.5×10$^6$ hepatocytes were co-incubated with 0-2×10$^6$ alloactive splenic T cells isolated from LP/J BM+T cells→B6 recipients. Co-incubation induced increased hepatocyte apoptosis from a baseline of 4.7±0.7% to 33.8±1.9% by 16 hr, as detected by nuclear morphologic changes (FIG. 16A). Consistent with data from a number of in vivo studies, B6.MRL.lpr hepatocytes lacking a functional Fas receptor were resistant to this mode of CTL-induced apoptosis (FIG. 16A, left panel), while selective inhibition of the granule exocytosis-mediated cytolytic pathway by 2 hr incubation with 100 ng/ml CMA had no effect on hepatocyte apoptosis (FIG. 16A, right panel). These studies indicate that CTL-mediated hepatocyte apoptosis in this model requires Fas but not perforin/granzyme signaling. Although prior studies showed that Fas levels were unaltered in asmase$^{-/-}$ hepatocytes, asmase$^{-/-}$ hepatocytes were nonetheless resistant to apoptosis in the ex vivo GvHD model at all doses of allogeneic effector T cells from 0.1-2×10$^6$ (FIG. 16B), and at all times from 4-48 hr (data not shown).

Figure 16C:
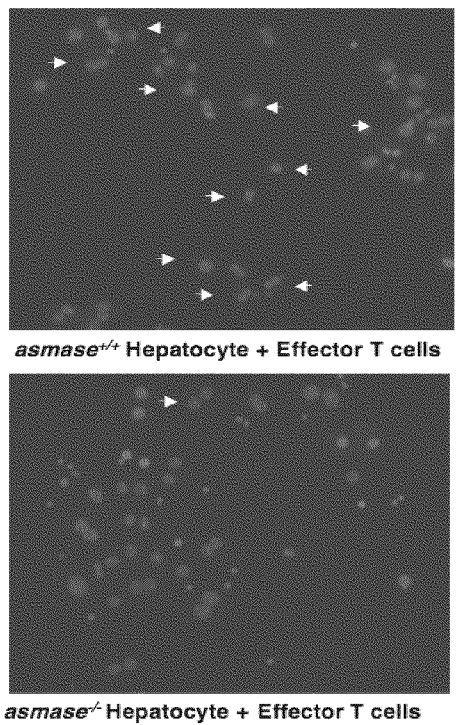
Figure 16D:
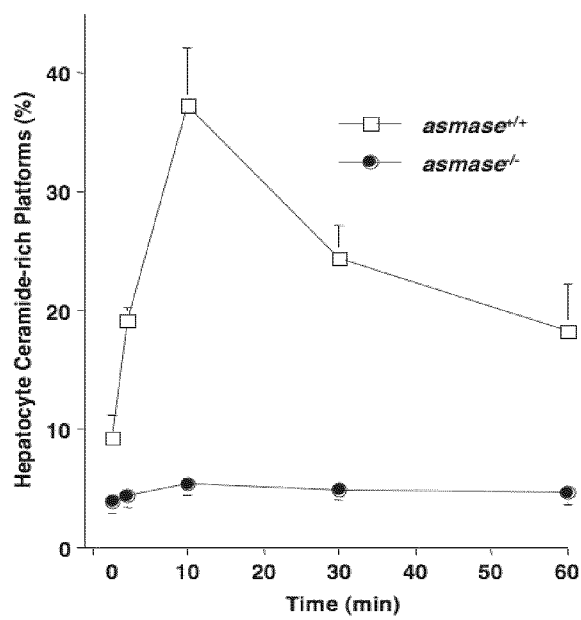

Whereas Fas-mediated apoptotic death receptor activation requires generation of ceramide-rich platforms in some cell systems, CTL-induced platform generation was assessed in asmase$^{+/+}$ and asmase$^{-/-}$ hepatocytes in the ex vivo model of GvHD. Alloactivated T cells induced rapid generation of ceramide-rich platforms on the surface of the target hepatocytes 10 min following co-incubation (FIG. 16C). Platform generation increased within one minute, peaked at 10 min, and persisted for over 60 min (FIG. 16D). Fas, required for apoptosis in this system, concentrated within the ceramide-rich platform as determined by confocal microscopy. In contrast, asmase$^{-/-}$ hepatocytes were completely resistant to ceramide-rich platform formation (FIG. 16C and quantified in FIG. 16D) and Fas concentration therein, demonstrating that CTL-induced platform generation in hepatocytes was ASMase-dependent. Concomitantly, CTLs induced a 1.5±0.1 fold overall increase in ceramide signal as determined by mean fluorescence intensity per pixel in asmase$^{+/+}$ hepatocytes (p<0.005 compared to unstimulated controls) which did not occur in asmase$^{-/-}$ hepatocytes, accounting for the difference in intensity of the ceramide staining in the upper vs. lower panels of FIG. 16C.

Figure 16E:
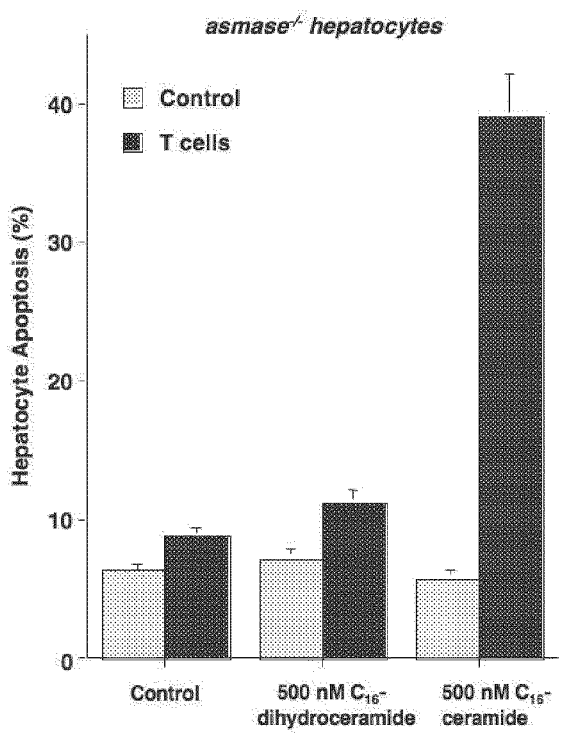
Figure 16F:
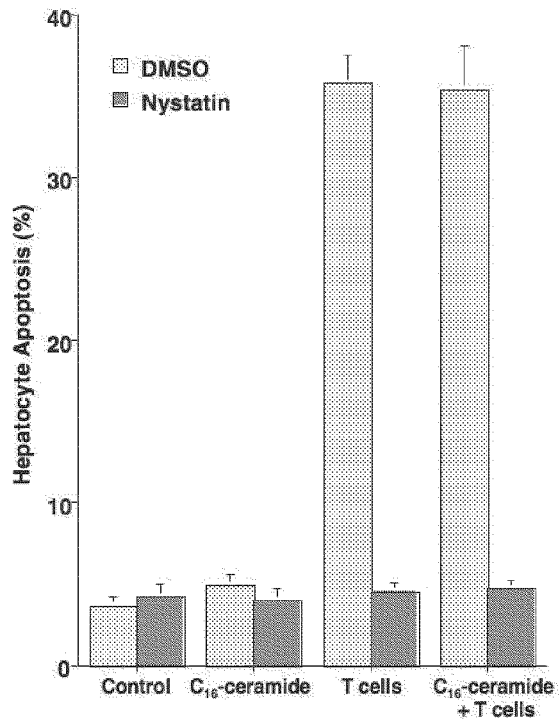

To demonstrate that hepatocyte apoptosis was specifically ceramide-dependent and not a consequence of ASMase deficiency, we added sub-apoptotic concentrations of exogenous C16-ceramide (up to 500 nM) to asmase$^{-/-}$ hepatocytes in the ex vivo GvHD assay. Consistent with restoration of platform generation in human asmase$^{-/-}$ lymphocytes by low dose long chain natural ceramide, a sublethal dose of exogenous $C_{16}$-ceramide (≥200 nM) restored platform formation in CTL-treated asmase$^{-/-}$ hepatocytes to 46.3±1.3% of cells, demonstrating that ASMase-mediated ceramide generation drives platform formation. $C_{16}$-ceramide nearly completely restored CTL-induced apoptosis to asmase$^{-/-}$ hepatocytes (FIG. 16E), bypassing the requirement for target cell ASMase. In contrast, $C_{16}$-dihydroceramide, the biologically-inactive analog of $C_{16}$-ceramide, failed to restore CTL-induced platform generation (not shown) or hepatocyte apoptosis (FIG. 16E). These data demonstrate unequivocally that CTL-induced hepatocyte apoptosis ex vivo requires target cell ceramide generation for efficient cell death induction, consistent with in vivo protection from acute GvHD observed in asmase$^{-/-}$ mice. Furthermore, pharmacologic disruption of cell surface rafts, sites of sphingomyelin concentration, with the cholesterol-chelating agent nystatin abrogated CTL-induced ceramide-rich platform generation (not shown) and completely inhibited 2×10$^6$ alloactivated CTL-induced hepatocyte apoptosis (FIG. 16F). Exogenous $C_{16}$-ceramide was unable to overcome cholesterol chelation (FIG. 16F), suggesting that ceramide-rich platform formation requires functional rafts for signaling, possibly serving as a site for pre-assembly of the apoptotic machinery.

Figure 17:
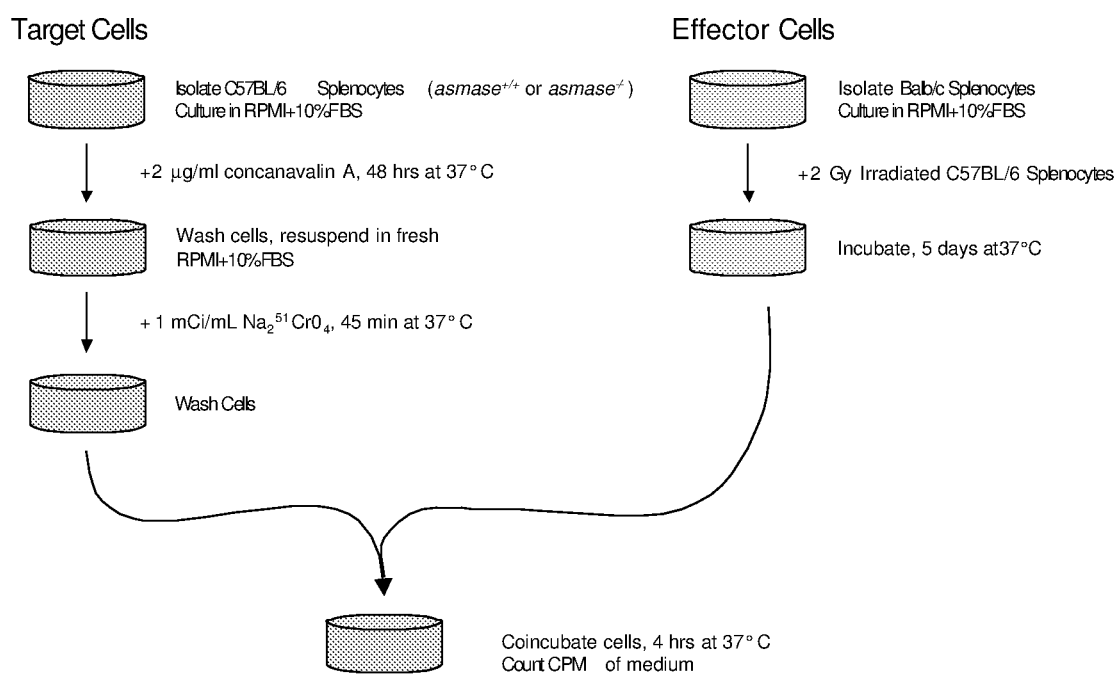
FIG. 17. Schematic of the in vitro mixed lymphocyte reaction (MLR) assay.
Figure 18:
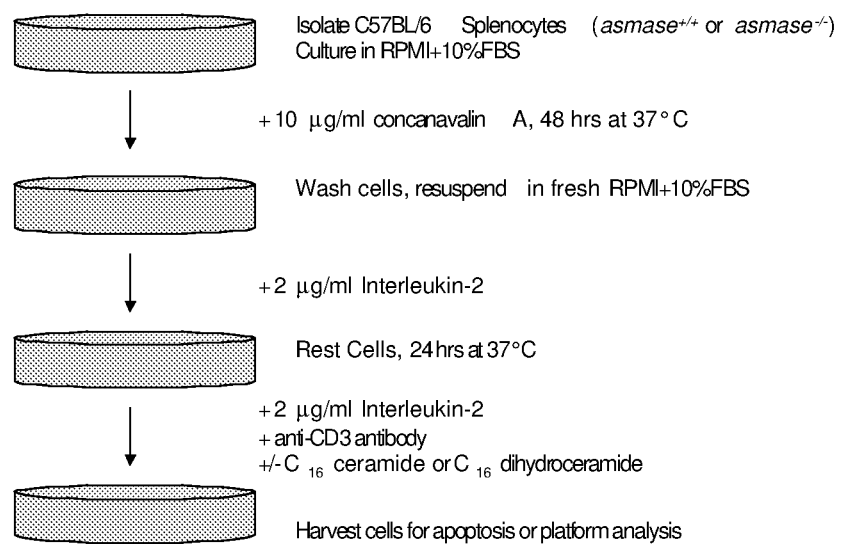
FIG. 18. Schematic of the in vitro activation-induced cell death (AICD) assay.
Figure 19A:
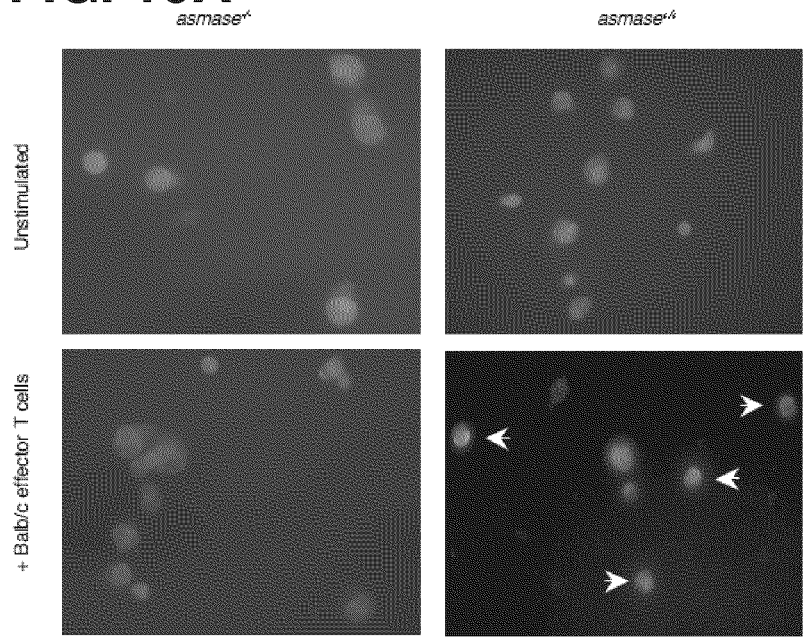
FIGS. 19A-19G. In vitro activated CTLs require target splenocyte ASMase for efficient killing.

To show the generic role of target cell ASMase in T cell-induced lysis, we used two standardized assays for T cell function; MLR-primed CTL-induced splenocyte lysis (FIG. 17) and in vitro activation-induced cell death (AICD) of T cells (FIG. 18). The role of target cell ASMase was assessed in an in vitro activated MLR, in which C57BL/6 splenocyte target cells of asmase$^{+/+}$ or asmase$^{-/-}$ genotype were stimulated for 48 hrs with mitogen, washed and chromium labeled. These cells were then coincubated with effector Balb/c splenocytes activated for 5 days by culture with irradiated C57BL/6 splenocytes. Chromium release was quantified and the % lysis was calculated. To test the ability of in vitro activated splenocytes to lyse asmase$^{-/-}$ target cells, Balb/c effector T cells were activated by culture for 5 days with 5×10$^6$ irradiated (2 Gy) C57BL/6 splenocytes. Target asmase$^{+/+}$ or asmase$^{-/-}$ C57BL/6 splenocytes were prepared by stimulation with 10 mg/ml conA for 48 hrs and $^{51}$Cr labeled to assess CTL-mediated chromium release. Washed splenocytes cells were coincubated with increasing ratios of activated effector Balb/c T cells, and $^{51}$Cr release was quantified 6 hour thereafter. FIG. 19A.

Figure 19B:
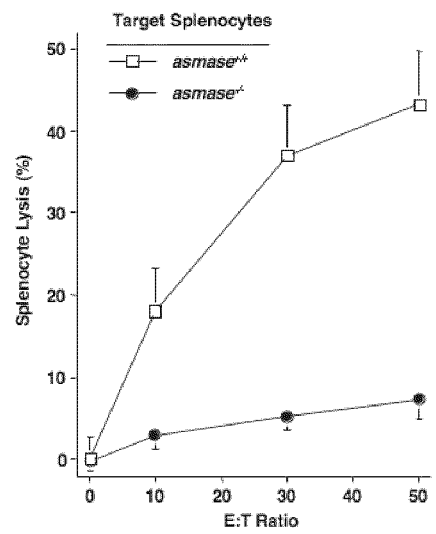
Figure 19C:
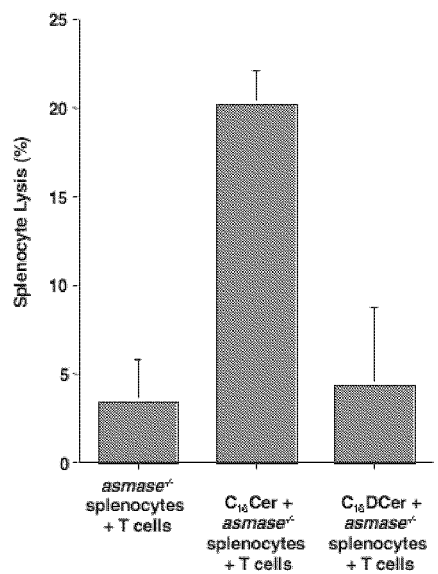

To evaluate a potential generic role for target cell ASMase in platform generation in T cell-induced lysis, we tested two standardized assays for T cell-mediated cytolysis, MLR-primed CTL-induced splenocyte lysis, and in vitro AICD of T cells. For the in vitro activated splenocyte lysis assay, BALB/c effector T cells were stimulated by culture for 5 days with 5×10$^6$ irradiated (2 Gy) C57BL/6 splenocytes, and thereafter coincubated with asmase$^{+/+}$ or asmase$^{-/-}$ target C57BL/6 splenocytes prepared by stimulation with 10 g/ml conA for 48 hr. Co-incubation of effector T cells with asmase$^{+/+}$ target splenocytes, Mitotracker Red-labeled for detection, resulted in rapid generation on target cells of ceramide-rich platforms. Within 5 min of co-incubation, platform incidence on target asmase$^{+/+}$ splenocytes increased from 4.7±2.1 to 25.8±6.6% (p<0.01; FIG. 19A). Fas colocalized within these ceramide-rich platforms (data not shown). Platform generation was absent in asmase$^{-/-}$ splenocytes, apparent in only 5.9±3.5% of the population 10 min post stimulation. Furthermore, MLR-primed CTLs induced 43.2±6.5% asmase$^{+/+}$ splenocyte lysis at an effector:target ratio of 50:1 (FIG. 19B), attenuated to 7.3±2.5% lysis in asmase$^{-/-}$ target cells, as quantified by $^{51}$Cr-release assay. Sublethal exogenous 500 nM $C_{16}$-ceramide restored both platform generation and CTL-induced lysis of asmase$^{-/-}$ target splenocytes, whereas $C_{16}$-dihydroceramide was ineffective in both events (not shown and FIG. 19C). These data indicate that in vitro-primed CTL lysis of conA blasts activates target cell platform generation in an ASMase-dependent manner, and that platforms are required for efficient lysis of target cells in these models.

Figure 19D:
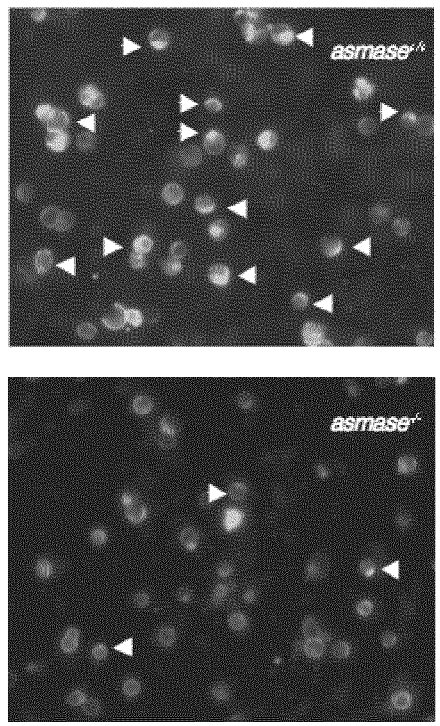
Figure 19E:
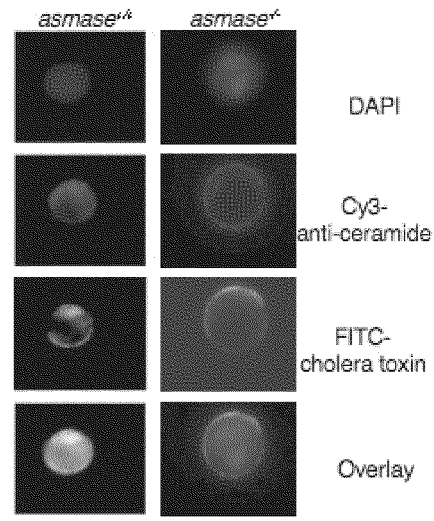

To define a role for target cell ASMase in AICD, asmase$^{+/+}$, asmase$^{-/-}$ or MRL.lpr (FasR$^{-/-}$) T cells were stimulated for 24 hr with 10 microgam/ml ConA, washed, rested in medium containing 20 U/ml rIL-2 for 24 hr, and finally AICD was initiated by restimulation in medium containing 20 U/ml rIL-2 and increasing concentrations of plate bound anti-CD3 mAb for 24 hr. AICD induction by anti-CD3 mAb conferred ceramide-rich platform generation 4 hr following stimulation (FIG. 19D), evident in 26.4±1.6% of the population of asmase$^{+/+}$ T cells compared to 5.1±1.0% of asmase$^{-/-}$ T cells (p<0.005). Confocal analysis identified colocalization of the sphingolipid $GM_1$ (FIG. 19E) and Fas within ceramide-rich platforms in asmase$^{+/+}$ T cells.

Figure 19F:
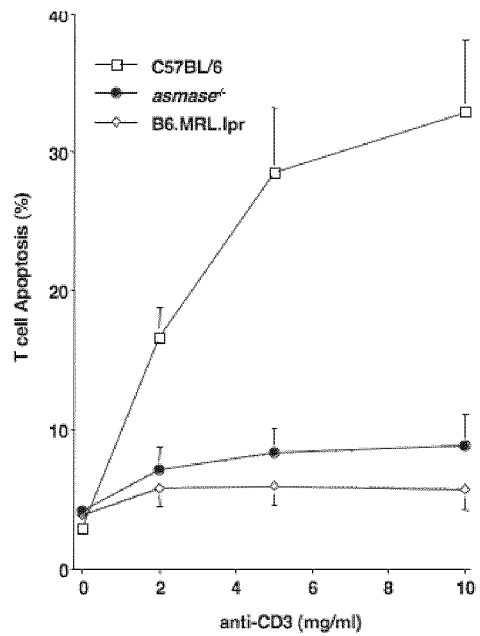
Figure 19G:
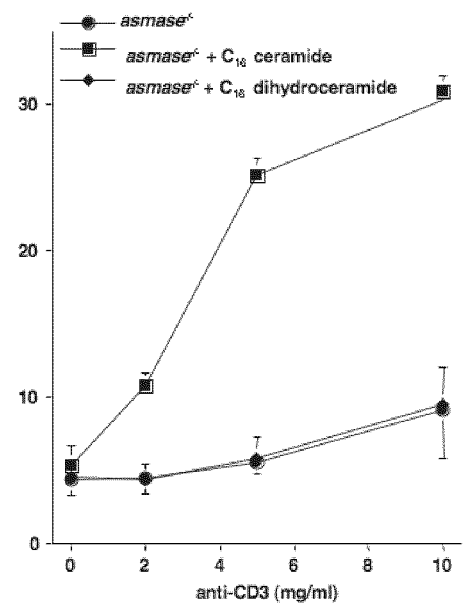

To characterize the impact of platform generation on AICD, asmase$^{+/+}$ and asmase$^{-/-}$ T cells were induced to undergo AICD and apoptosis was quantified 16 hr thereafter. Apoptosis in asmase$^{+/+}$ T cells was anti-CD3 mAb dose-dependent, reaching 32.9±5.2% apoptosis 16 hr post induction (FIG. 19F). In contrast, apoptosis was abrogated in MRL.lpr (FasR$^{-/-}$) T cells (FIG. 19F), confirming the requirement for Fas/FasL interaction in this system. While asmase$^{-/-}$ i T cells were induced to proliferate by anti-CD3 mAb equally well as asmase$^{+/+}$ T cells, and were equally effective as asmase$^{+/+}$ T cells in lysis of tumor cells, they displayed near complete resistance to AICD-induced apoptosis in vitro. asmase$^{-/-}$ splenocytes failed to undergo detectable apoptosis above background (8.8%) in response to up to 10 ng/ml anti-CD3 (p<0.05 vs. asmase$^{+/+}$ at 10 ng/ml anti-CD3; FIG. 19F). This occurred despite normal upregulation of Fas and FasL (not shown). Natural long chain $C_{16}$-ceramide, but not $C_{16}$-dihydoceramide, completely restored platform generation in (not shown) and apoptosis of asmase$^{-/-}$ T cells stimulated to undergo AICD (FIG. 19G). These data provide compelling evidence that target cell ASMase-mediated ceramide-rich platform formation is required for T cell-induced apoptosis in both antigen-disparate and fratricidic settings.

Treatment and Prevention of GvHD with Anti-Ceramide Antibody

Figure 20:
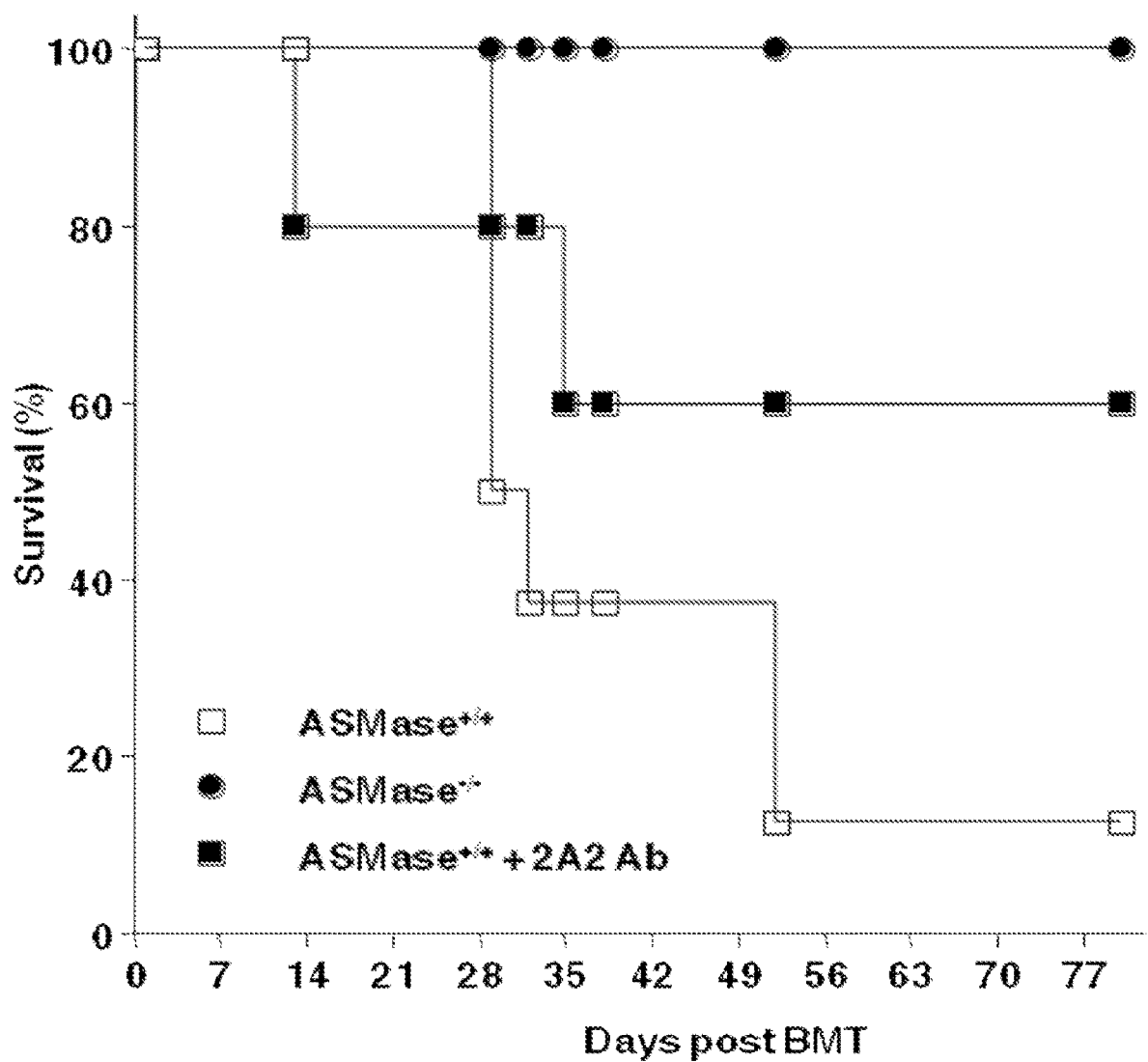
FIG. 20. 2A2 Antibody Impacts acute GvHD in vivo, partially recapitulating the asmase$^{-/-}$ phenotype. Kaplan-Meier survival analysis following transplantation of LP BM and T cells as described in FIG. 14. The group receiving 2A2 antibody received 750 micrograms antibody 15 min prior to the first half of 1100 cGy split-dose TBI.

We next looked at the effect of treatment with 2A2 anti-ceramide antibody IgM on survival following allogeneic bone marrow and T cell transplantation (FIG. 20). Using the same of LP/J donor (H-2b) into C57BL/6 recipient (H-2b) model described in FIG. 15, we demonstrate that 2A2 antibody treatment significantly reduced objective indicia of acute graft-versus-host disease in vivo, partially recapitulating the asmase–/– phenotype. C57BL/6asmase+/+ or C57BL/6asmase–/– were lethally irradiated with a split dose of 1100 cGy TBI. The C57BL/6asmase+/+ group receiving 2A2 antibody received 750 micrograms antibody 15 min prior to the first half of split-dose TBI. Thereafter, all mice received intravenous injection of minor antigen-mismatched LP TCD-BM cells (5×106) with splenic T cells (3×106). Survival was monitored daily, and results were expressed by Kaplan-Meier survival analysis. Administration of 2A2 increased animal survival 100 days following transplantation from 12.5% to 60% (FIG. 20).

Figure 21:
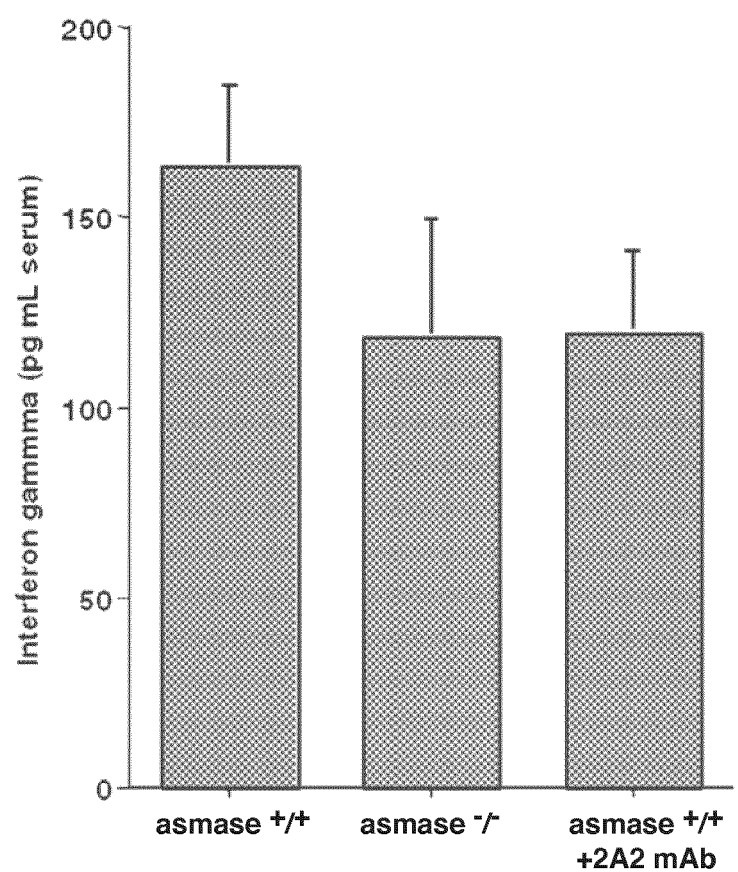
FIG. 21. 2A2 Antibody Attenuates Serum Cytokine Storm Associated with acute GvHD. Serum was harvested on day 7 following BMT from mice undergoing experimental acute GvHD from FIG. 15. Serum interferon-gamma was quantified by ELISA, according to manufacturer's protocol (R&D Systems).

Given the role that ASMase plays in GvHD cytokine storm generation, we next studied the ability of 2A2 Antibody to attenuate this adverse response. Serum was harvested from wild type, asmase$^{-/-}$ and 2A2-treated animals on day 7 following BMT from the group analyzed as described above (FIG. 21). Serum interferon-gamma was quantified by ELISA, according to manufacturer's protocol (R&D Systems). Our results show that WT mice treated with 2A2 mAb responded similarly to ASMase deficient mice, with an approximate 25% reduction in serum interferon gamma.

These results show that GvHD and other T cell-mediated autoimmune diseases associated with an increase in pro-inflammatory cytokines can be treated by administering a therapeutic amount of an anti-ceramide antibody, preferably 2A2 anti-ceramide monoclonal IgM or a biologically active fragment thereof as is described herein. Our in vitro results showed that nystatin also decreased T cell cytolysis ex vivo support certain embodiments wherein GvHD and autoimmune diseases are treated or prevented by administering one or more statins, preferably together with a humanized anti-ceramide antibody such as 2A2. Other embodiments are directed to new compositions of one or more statins and one or more anti-ceramide antibodies. As for treating GI syndrome, routine experimentation will determine the effective amount of humanized monoclonal anti-ceramide antibody to use. The amount of anti-ceramide antibody to be administered therapeutically ranges from about 1 ug to 100 ug/ml. This amount typically varies and can be an amount sufficient to achieve serum therapeutic agent levels typically of between about 1 microgram per milliliter and about 10 micrograms per milliliter in the subject.

The present studies define formation of ceramide-rich membrane platforms in the exoplasmic leaflet of the plasma membrane of target cells as a critical step in both microvascular apoptosis of the GI following ionizing radiation and lytic attack by CTLs upon immune targets. These structures, which form within seconds of stimulation, are readily detected by confocal or conventional microscopy as they are quite large, often reaching three microns in diameter. We have shown that genetic or pharmacologic disruption of platforms, for example by blocking ASMase or Bax and by administering anti-ceramide antibodies, prevents radiation-induced cell death in vitro and in vivo, as well as CTL-mediated death in three distinct cellular models of CTL-induced cell killing. Treatment with monoclonal anti-ceramide antibodies markedly reduced multiple aspects of the pathophysiologic response in gastrointestinal radiation toxicity and standardized major and minor mismatch models of GvHD.

Summary

The present studies provide new evidence that linkage between microvascular endothelial apoptosis and stem cell clonogen lethality is a generic mechanism for induction of radiation damage to the mouse intestines. Bax deficient mice provide evidence that it is the endothelial apoptotic response, rather than another event regulated by ASMase signaling, that impacts the fate of irradiated crypt stem cell clonogens. The availability of a pharmacologic that can inhibit ASMase (such as imipramine, antisense nucleic acids or siRNA) is a valuable therapeutic in patients requiring high dose abdominal radiation, with the potential of selectively antagonizing GI toxicity without impacting tumor cell kill. Another valuable therapy is the use of ceramide-targeting pharmacologics such as anti-ceramide antibody to antagonize raft clustering and apoptosis of the GI early in the response to accidental radiation exposure or large-scale radiological incident. Lethal GI toxicity following radiation exposure, for which there is no current therapeutic option, is a primary concern of the National Institute of Health in lieu of the current state of world affairs.

As the results we presented here show, ceramide-rich platforms are required for T cell-mediated autoimmune syndromes in vivo. ASMase had been shown to regulate hepatocyte apoptosis in phytohemagglutin (PHA)-induced hepatitis, a model for acute T-cell mediated autoaggressive liver disorder (S. Kirschnek, F. Paris, M. Weller et al., *J Biol Chem* 275 (35), 27316 (2000)). PHA stimulates FasL induction on lymphocytes and upon their migration to the liver, hepatocytes are killed by apoptosis, prompting hepatitis (K. Seino, N. Kayagaki, K. Takeda et al., *Gastroenterology* 113 (4), 1315 (1997)). ASMase deficiency protected hepatocytes from apoptosis despite normal upregulation of lymphocyte FasL. A role for ASMase in CD4-activated T cell-induced cytolysis has been reported (Z. Q. Wang, A. Dudhane, T. Orlikowsky et al., *Eur J Immunol* 24 (7), 1549 (1994)). CD4 activation by the HIV receptor molecule gp120, or by an agonistic anti-CD4 antibody, activates the Fas/FasL system and initiates apoptosis, whereas CD4$^+$ T cells deficient in ASMase were unable to undergo apoptosis upon in vivo injection of anti-CD4 antibody (S. Kirschnek, F. Paris, M. Weller et al., *J Biol Chem* 275 (35), 27316 (2000)). We have now shown that ASMase-generated ceramide is universally required in cytokine-mediated T cell-induced apoptosis, and in preventing apoptosis of endothelial microvasculature which underlies the pathology of GI syndrome). We have shown that blocking ASMase-generated ceramide with anti-ceramide antibodies also decreased serum proinflammatory cytokine expression. Thus any disease working through TNF superfamily receptor signaling including Fas/FasL and TNF/TNFR interactions can be treated or prevented by administering a therapeutic amount of an antibody that binds to the ASMase-generated ceramide or by inhibition of ASMase or Bax.

The experiments described herein show for the first time that activation of host ASMase and formation of ceramide-rich platforms are critical events in instigation of acute GvHD. We showed this by the marked reduction in Type I cytokine production and CTL clonal expansion, steps necessary to feed forward GvHD, when mismatched alloactivated CTLs are added to marrow transplants into asmase$^{-/-}$ mice. As with GI syndrome, although different etiologies, GvHD responded to treatment with anti-ceramide antibodies and blocking ASMase or Bax expression.

The benefit of inactivation of ceramide-rich platforms is not restricted to Fas-mediated biologic effects because other inflammatory cytokines including but not limited to TNF, IL-1 and TRAIL similarly use ASMase for transmembrane signal transmission. Hence, ASMase-generated ceramide-rich platforms represent a promiscuous target for GvHD and other immune disorders that utilize multiple cytokines to instigate pathophysiology.

Antibodies

An "antibody" refers to an intact immunoglobulin or to an antigen-binding portion thereof that competes with the intact antibody for specific binding. Antigen-binding portions may be produced by recombinant DNA techniques or by enzymatic or chemical cleavage of intact antibodies. Antigen-binding portions include, inter alia, Fab, Fab', F(ab').sub.2, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide.

An "immunoglobulin" is a tetrameric molecule. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as .kappa. and .lamda. light chains. Heavy chains are classified as .mu., .DELTA., .gamma., .alpha., or .epsilon., and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites. Immunoglobulin chains exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminus to C-terminus, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901 917 (1987); Chothia et al. Nature 342:878 883 (1989).

An Fab fragment is a monovalent fragment consisting of the VL, VH, CL and CH I domains; a F(ab').sub.2 fragment is a bivalent fragment comprising two Fab fragments linked by a disulfide bridge at the hinge region; a Fd fragment consists of the VH and CH1 domains; an Fv fragment consists of the VL and VH domains of a single arm of an antibody; and a dAb fragment (Ward et al., Nature 341:544 546, 1989) consists of a VH domain. A single-chain antibody (scFv) is an antibody in which a VL and VH regions are paired to form a monovalent molecules via a synthetic linker that enables them to be made as a single protein chain (Bird et al., Science 242:423 426, 1988 and Huston et al., Proc. Natl. Acad. Sci. USA 85:5879 5883, 1988). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., Proc. Natl. Acad. Sci. USA 90:6444 6448, 1993, and Poljak, R. J., et al., Structure 2:1121 1123, 1994). One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a "bispecific" or "bifunctional" antibody has two different binding sites.

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature.

The term "human antibody" includes all antibodies that have one or more variable and constant regions derived from human immunoglobulin sequences. In a preferred embodiment, all of the variable and constant domains are derived from human immunoglobulin sequences (a fully human antibody). These antibodies may be prepared in a variety of ways, as described below.

A humanized antibody is an antibody that is derived from a non-human species, in which certain amino acids in the framework and constant domains of the heavy and light chains have been mutated so as to avoid or abrogate an immune response in humans. Alternatively, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293, incorporated herein by reference.

The term "chimeric antibody" refers to an antibody that contains one or more regions from one antibody and one or more regions from one or more other antibodies.

Fragments or analogs of antibodies can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991).

Small Interfering RNA

Small interfering RNA can also be used therapeutically to treat or prevent GVHD, radiation induced diseases including GI syndrome, inflammation and autoimmune diseases in a subject by administering an si RNA at least a portion of which is complementary to and specifically hybridizes with the mRNA encoding ASMase or Bax, in order to reduce or inhibit the respective expression, thereby blocking apoptosis.

US Patent Application 20040023390 (incorporated herein by reference) teaches that double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shut-down of protein synthesis and even cell death through apoptosis. Recent work shows that RNA fragments are the sequence-specific mediators of RNAi (Elbashir et al., 2001). Interference of gene expression by these small interfering RNA (siRNA) is now recognized as a naturally occurring strategy for silencing genes in *C. elegans, Drosophila*, plants, and in mouse embryonic stem cells, oocytes and early embryos (Cogoni et al., 1994; Baulcombe, 1996; Kennerdell, 1998; Timmons, 1998; Waterhouse et al., 1998; Wianny and Zernicka-Goetz, 2000; Yang et al., 2001; Svoboda et al., 2000).

In mammalian cell culture, a siRNA-mediated reduction in gene expression has been accomplished by transfecting cells with synthetic RNA nucleic acids (Caplan et al., 2001; Elbashir et al., 2001). The 20040023390 application, the entire contents of which are hereby incorporated by reference as if fully set forth herein, provides methods using a viral vector containing an expression cassette containing a pol II promoter operably-linked to a nucleic acid sequence encoding a small interfering RNA molecule (siRNA) targeted against a gene of interest.

As used herein RNAi is the process of RNA interference. A typical mRNA produces approximately 5,000 copies of a protein. RNAi is a process that interferes with or significantly reduces the number of protein copies made by an mRNA. For example, a double-stranded short interfering RNA (siRNA) molecule is engineered to complement and match the protein-encoding nucleotide sequence of the target mRNA to be interfered with. Following intracellular delivery, the siRNA molecule associates with an RNA-induced silencing complex (RISC). The siRNA-associated RISC binds the target mRNA (such as mRNA encoding ASMase or Bax) through a base-pairing interaction and degrades it. The RISC remains capable of degrading additional copies of the targeted mRNA. Other forms of RNA can be used such as short hairpin RNA and longer RNA molecules. Longer molecules cause cell death, for example by instigating apoptosis and inducing an interferon response. Cell death was the major hurdle to achieving RNAi in mammals because dsRNAs longer than 30 nucleotides activated defense mechanisms that resulted in non-specific degradation of RNA transcripts and a general shutdown of the host cell. Using from about 20 to about 29 nucleotide siRNAs to mediate gene-specific suppression in mammalian cells has apparently overcome this obstacle. These siRNAs are long enough to cause gene suppression but not of a length that induces an interferon response.

The invention has been described in the foregoing specification with reference to specific embodiments. It will however be evident that various modifications and changes may be made to the embodiments without departing from the broader spirit and scope of the invention. The specification and drawings are to be regarded in an illustrative rather than a restrictive sense.

Antisense Nucleic Acids

As used herein, the term "nucleic acid" refers to both RNA and DNA, including cDNA, genomic DNA, and synthetic (e.g., chemically synthesized) DNA. The nucleic acid can be double-stranded or single-stranded (i.e., a sense or an antisense single strand). As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that flank an ARPKD gene). The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Other embodiments of the present invention are directed to the use of antisense nucleic acids (either DNA or RNA) or small interfering RNA to inhibit expression of ASMase or Bax or Bak or a biologically active fragment or variant thereof. The antisense nucleic acid can be antisense RNA, antisense DNA or small interfering RNA. Based on the known sequence of ASMase or Bax or Bak, antisense DNA or RNA that hybridize sufficiently to the respective gene or mRNA to turn off expression can be readily designed and engineered using methods known in the art.

The isolated antisense or siRNA nucleic acid molecules for use in the invention comprise a nucleic acid molecule which is a complement of the gene or mRNA sequence for the target: the gene (full genomic DNA) encoding ASMasae, identified as SEQ ID NO: 1, the gene encoding human Bax, identified as SEQ ID NO: 2, or the gene encoding human Bak, identified as SEQ ID NO:3. A nucleic acid molecule which is complementary to a given nucleotide sequence is one which is sufficiently complementary to the given nucleotide sequence that it can hybridize to the given nucleotide sequence thereby forming a stable duplex.

Antisense nucleic acid molecules, i.e., molecules which are complementary to a sense nucleic acid encoding a protein, e.g., complementary to the coding strand of a double-stranded DNA molecule (or cDNA) or complementary to an mRNA sequence. Accordingly, an antisense nucleic acid can hydrogen bond to a sense nucleic acid. The antisense nucleic acid can be complementary to an entire ASMase, Bak or Bax coding strand, or to only a portion thereof, e.g., all or part of the protein coding region (or open reading frame). An antisense nucleic acid molecule can be antisense to a noncoding region of the coding strand of a nucleotide sequence encoding ASMase, Bak or Bax. The noncoding regions ("5' and 3' untranslated regions") are the 5' and 3' sequences which flank the coding region and are not translated into amino acids.

Given the coding strand sequences encoding ASMase (cDNA SEQ ID NO. 2, GENOMIC DNA SEQ ID NO. 7, Bax cDNA SEQ ID NO. 3, GENOMIC DNA SEQ ID NO. 8, or Bak cDNA SEQ ID NO. 5, GENOMIC DNA SEQ ID NO. 9 disclosed herein, antisense nucleic acids of the invention can be designed according to the rules of Watson and Crick base pairing. The antisense nucleic acid molecule can be complementary to the entire coding region of ASMase, Bak or Bax mRNA, but more preferably is an oligonucleotide which is antisense to only a portion of the coding or noncoding region of ASMase, Bak or Bax mRNA. For example, the antisense oligonucleotide can be complementary to the region surrounding the translation start site of ASMase, Bak or Bax. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-hodouracil, hypoxanthine, xanthine, 4-acetylcytosine, 5-(carboxyhydroxylmethyl)uracil, 5-carboxymethylaminomethyl-2-thouridine, 5-carboxymethylaminometh-yluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-metnylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopenten-yladenine, uracil-5-oxyacetic acid (v), wybutoxosine, pseudouracil, queosine, 2-thiocytosine, 5-methyl-2-thiouracil, 2-thlouracil, 4-thiouracil, 5-methyluracil, uracil-5-oxyacetic acid methylester, uracil-5-cxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding the protein of interest to thereby inhibit expression of the protein, e.g., by inhibiting transcription and/or translation. The hybridization can be by conventional nucleotide complementary to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an alpha-anomeric nucleic acid molecule. An .alpha.-anomeric nucleic acid molecule forms specific double-stranded hybrids with complementary RNA in which, contrary to the usual .beta.-units, the strands run parallel to each other (Gaultier et al. (1987) Nucleic Acids. Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215:327-330). All of the methods described in the above articles regarding antisense technology are incorporated herein by reference.

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585-591)) can be used to catalytically cleave ASMase, Bak or Bax transcripts thereby inhibit translation of ASMase, Bak or Bax. A ribozyme having specificity for an ASMase, Bak or Bax-encoding nucleic acid can be designed based upon the nucleotide sequence of a ASMase, Bak or BaxcDNA disclosed herein. For example, a derivative of a Tetrahymena L-19 IVS RNA can be constructed in which the nucleotide sequence of the active site is complementary to the nucleotide sequence to be cleaved in an ASMase, Bak or Bax-encoding mRNA. See, e.g., Cech et al. U.S. Pat. No. 4,987,071; and Cech et al. U.S. Pat. No. 5,116,742. Alternatively, ASMase, Bak or Bax mRNA can be used to select a catalytic RNA having a specific ribonuclease activity from a pool of RNA molecules. See, e.g., Bartel and Szostak (1993) Science 261:1411-1418, incorporated herein by reference.

As used herein, the term "nucleic acid" refers to both RNA and DNA, including cDNA, genomic DNA, and synthetic (e.g., chemically synthesized) DNA. The nucleic acid can be double-stranded or single-stranded (i.e., a sense or an antisense single strand). As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that flank an ARPKD gene). The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Pharmaceutical Compositions

The present invention also includes pharmaceutical compositions and formulations of the 2A2 humanized monoclonal antibody, optionally formulated with one or more statins or imipramine. Other pharmaceutical compositions include the antisense nucleic acids and small interfering RNAs of the invention that are administered reduce ASMase or Bak or Bax expression.

Pharmaceutical compositions of the present invention contain the therapeutic agent (anti-ceramide antibody, enzyme inhibitors, antisense nucleic acids or si RNA) in an amount sufficient to prevent or treat the enumerated diseases: GVHD, radiation induced diseases including GI syndrome, inflammation and autoimmune diseases in a subject. These pharmaceutical compositions are suitable for administration to a subject in need of prophylaxis or therapy of GVHD, radiation induced diseases including GI syndrome, inflammation and autoimmune diseases in a subject. The subject is preferably a human but can be non-human as well. A suitable subject can be an individual who is suspected of having, has been diagnosed as having, or is at risk of developing one of the enumerated diseases. Therapeutic compositions may contain, for example, such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%-95% of active ingredient, preferably 2%-70% active ingredient.

Antibodies and antisense nucleotides and enzyme inhibitors or statins of the present invention can also be mixed with diluents or excipients which are compatible and physiologically tolerable. Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents.

In some embodiments, the therapeutic compositions of the present invention are prepared either as liquid solutions or suspensions, as sprays, or in solid forms. Oral formulations usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%-95% of active ingredient, preferably 2%-70%. One example of an oral composition useful for delivering the therapeutic compositions of the present invention is described in U.S. Pat. No. 5,643,602 (incorporated herein by reference).

Additional formulations which are suitable for other modes of administration, such as topical administration, include salves, tinctures, creams, lotions, transdermal patches, and suppositories. For salves and creams, traditional binders, carriers and excipients may include, for example, polyalkylene glycols or triglycerides. One example of a topical delivery method is described in U.S. Pat. No. 5,834,016 (incorporated herein by reference). Other liposomal delivery methods may also be employed (See, e.g., U.S. Pat. Nos. 5,851,548 and 5,711,964, both of which are herein incorporated by reference).

The formulations may also contain more than one active compound as necessary for the particular indication being treated, preferably those with complementary activities that do not adversely affect each other. Such molecules are suitably present in combination in amounts that are effective for the purpose intended. For example, the 2A2 antibody could be formulated with a statin or with imipramine.

Sustained-release preparations may also be prepared. Suitable examples of sustained release preparations include semipermeable matrices of solid hydrophobic polymers containing the antibodies or fragments, nystatin, imipramine or combinations thereof, which matrices are in the form of shaped articles, e.g., films, or microcapsule. Examples of sustained-release matrices include, but are not limited to, polyesters, hydrogels (for example, poly (2-hydroxyethylmethacrylate), or poly (vinylalcohol)), polylactides, copolymers of L-glutamic acid and y ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The antibodies and antisense or siRNAs of the present invention may be administered by any suitable means, including parenteral, subcutaneous, topical, intraperitoneal, intrapulmonary, and intranasal, and, intralesional administration (e.g. for local immunosuppressive treatment). Parenteral infusions include intramuscular, intravenous, intraarterial, intraperitoneal, or subcutaneous administration. In addition suitable administration includes by pulse infusion, particularly with declining doses of the antibody. Preferably, the dosing is given by injections, most preferably intravenous or subcutaneous injections, depending in part on whether the administration is brief or chronic.

For the prevention or treatment of disease, the appropriate dosage of antibody will depend on the type of disease to be treated, the severity and course of the disease, whether the drug is administered for preventive or therapeutic purposes, previous therapy, the patient's clinical history and response to the new drugs (2A2 antibody, etc.) and the discretion of the attending physician. The antibodies and nucleotides or other drugs (imipramine and statins) are suitably administered to the patient at one time or over a series of treatments.

As mentioned above, the amount of anti-ceramide antibody to be administered therapeutically ranges from about 1 ug to 100 ug/ml. This amount typically varies and can be an amount sufficient to achieve serum therapeutic agent levels typically of between about 1 microgram per milliliter and about 10 micrograms per milliliter in the subject. The therapeutic agents of the invention can be administered by one or more separate administrations, or by continuous infusion. For repeated administrations over several days or longer, depending on the condition, the treatment is sustained until the symptoms are sufficiently reduced or eliminated. The progress of this therapy is easily monitored by conventional techniques and assays, and may be used to adjust dosage to achieve a therapeutic effect.

A candidate dosage of antisense nucleic acid or siRNA for use therapeutically can be determined initially by finding an amount that reduces expression of the target protein in a biological sample from a human or animal.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

EXAMPLES

Example 1: Materials & Methods

Cell Culture and Stimulation

Wild-type (clone E6-1), caspase $8^{-/-}$ (clone 19.2) and FADD$^{-/-}$ (clone 12.1) Jurkat T lymphocytes were obtained from ATCC (Rockville, Md.). Cells were grown in a 5% $CO_2$ incubator at 37° C. in RPMI 1640 medium supplemented with 10% heat-inactivated fetal bovine serum and 10 mM Hepes (pH 7.4), 2 mM L-glutamine, 1 mM sodium pyruvate, 100 μM nonessential amino acids, 100 units/ml penicillin, and 100 μg/ml streptomycin. Prior to stimulation with UV-C or anti-Fas, cells were resuspended in fresh medium and allowed to acclimate for 4 hours. Jurkat cells were then treated with 50 ng/ml anti-FasCH-11 activating antibody (Upstate Biotechnology, Lake Placid N.Y.) or 50 Joules/m$^2$ UV-C using an FB-UVXL-1000 Crosslinker (Fisher Biotech, Pittsburgh Pa.), unless otherwise indicated. For platform studies, Jurkat cells were incubated with CH-11 at 4° C. for 20 min to insure uniform receptor engagement, and warmed to 37° C. to initiate stimulation.

Where indicated, cells were pre-incubated with 10 μM z-VAD-fmk (Calbiochem, La Jolla Calif.), 30 μg/ml nystatin (Sigma-Aldrich, Milwaukee Wis.), 50 μM imipramine (Sigma-Aldrich) or 1 μg/ml mouse monoclonal anti-ceramide antibody MID15B4 (Alexis Biochemicals, San Diego Calif.). Nystatin, imipramine and anti-ceramide studies were performed in RPMI containing 0.5% lipid-free fetal bovine serum (HyClone, Logan Utah). In each study, an aliquot of cells were stained with trypan blue to assess viability.

Mice and Bone Marrow Transplantation (BMT)

C3H/HeJ, C3HeB/FeJ, LP/J ("LP," H-2b), B10.BR ("B10," H-2$^k$) and B6.MRL.lpr female mice, 8-12 weeks old, were purchased from Jackson Laboratories (Bar Harbor, Me.). SV129/C57BL/6$^{asmase-/-}$ and C57BL/6$^{Bax-/-}$ mice were inbred in our colony and genotyped as previously described [Horinouchi, 1995 #171; Knudson, 1995 #173]. Backcrossing the asmase$^{-/-}$ genotype onto the C57BL/6 background was performed by initially mating wildtype C57BL/6 females with male SV129/C57BL/6$^{asmase-/-}$ mice. Male $F_1$ mice with asmase$^{+/-}$ genotype were subsequently mated with C57BL/6 females. Thereafter, a mating protocol of male asmase$^{+/-}$ progeny with wildtype C57BL/6 female mice was continued for ten generations to obtain an asmase$^{+/-}$ genotype in pure C57BL/6 background. Once backcrossing was established, C57BL/6$^{asmase+/-}$ mice were interbred to obtain experimental animals. Male and female hosts were used in BMT experiments at 8-12 weeks of age. BMT protocols were approved by the Memorial Sloan-Kettering Cancer Center Institutional Animal Care and Use Committee. Mice were housed in a pathogen-free facility at Memorial Sloan-Kettering Cancer Center in sterilized micro-isolator cages and received normal chow and autoclaved hyperchlorinated drinking water (pH 3.0). This facility is approved by the American Association for Accreditation of Laboratory Animal Care and is maintained in accordance with the regulations and standards of the United States Department of Agriculture and the Department of Health and Human Services, National Institutes of Health.

Bone marrow (BM) cells were removed aseptically from femurs and tibias. Donor marrow was T-cell depleted using anti-Thy-1.2 antibody and low-TOX-M rabbit complement (Cedarlane Laboratories, Hornby, Canada). Splenic T cells were obtained by purification over a nylon wool column. Cells (5×10$^6$ BM cells with or without splenic T cells) were resuspended in Dulbecco's modified essential medium and transplanted by tail-vein infusion into lethally-irradiated recipients that had received 1100 cGy total body irradiation ($^{137}$Cs source) as a split dose with 3 hrs between doses on day 0.

Cell culture medium for lymphocyte and bone marrow harvesting consisted of RPMI 1640 supplemented with 10% heat-inactivated fetal calf serum, 100 U/mL penicillin, 100 μg/mL streptomycin, 2 mM L-glutamine, and 50 μM 2-mercaptoethanol. Anti-murine CD16/CD32 Fc block (2.4G2), fluorochrome-labeled CD3 (145-2C11), CD4 (RM4-5), CD8 (53-6.7), CD62L (MEL-14), and Ly-9.1 (30C7) antibodies were obtained from Pharmingen (San Diego, Calif.). Ammonium chloride red blood cell (RBC) lysis buffer, concanavalin A (conA) and concanamycin A (CMA) were obtained from Sigma (St. Louis, Mo.).

Ex Vivo Hepatocyte Culture

Hepatocytes were isolated by cannulation of the portal vein and retrograde in situ collagenase perfusion according to the method described by Klaunig94. Briefly, livers were perfused with 20 mL Buffer 1 (Krebs Ringer with glucose+ 0.1 mM EGTA) followed by 25 mL Buffer 2 [Krebs Ringer with glucose containing 0.2 mM CaCl2 with 5,000 units collagenase type I (Sigma)] at a rate of 7 ml/min by peristaltic pump (Rainin Instrument LLC. Woburn, Mass.). Perfused livers were excised and minced in Buffer 2, filtered through a 100 □M cell strainer, washed twice at 50×g and resuspended in RPMI 1640 complete medium containing 10% fetal bovine serum. Viability was routinely greater than 90%.

Apoptosis Quantitation

Apoptosis was assessed in vitro by two different techniques. TUNEL staining was performed on cells permeabilized with 0.1% Triton X-100 and 0.1% sodium citrate at 4° C. for 5 min, according to the manufacturer's instructions (Roche Molecular Biochemicals, Indianapolis Ind.). Alternately, stimulated cells were fixed with 2% paraformaldehyde, washed with phosphate buffered saline (PBS), and stained with 100 μl of 24 μg/ml bis-benzimide trihydrochloride solution (Hoechst #33258; Sigma-Aldrich, Milwaukee Wis.) for 10 min. Morphologic changes of nuclear apoptosis including chromatin condensation, segmentation and compaction along the periphery of the nucleus or the appearance of apoptotic bodies were quantified using an Axiovert S-100 Zeiss fluorescence microscope as previously described[33]. A minimum of 200 cells were examined per point.

Apoptosis was quantified in vivo in the endothelium of the lamina propria of the small intestines following TUNEL staining as described [Paris, 2001 #7]. Endothelial cells were identified by immunostaining using an antibody against the endothelial cell surface marker CD31 (PharMingen catalog no. 1951D) as previously published [Paris, 2001 #7].

Hepatocyte apoptosis was assessed on $0.5 \times 10^6$ hepatocytes rested for 30 min in complete medium and stimulated for 16 hrs at 37° C. in 5% $CO_2$ with 1 μg/mL anti-Fas Jo2 antibody (Pharmingen) or $0-2 \times 10^6$ splenic T cells isolated from C57BL/6 mice 2-3 weeks following transplantation of LP/J donor bone marrow and T cells as described. In some studies, hepatocytes were pretreated for 30 min with nystatin (50 g/mL, Sigma-Aldrich, Milwaukee Wis.), washed in RPMI, and resuspended in RPMI supplemented with 1% lipid-free FBS prior to stimulation.

Clonogenic Assay

Colony formation of Jurkat cells following UV-C or anti-Fas CH-11 treatment was evaluated using a soft agar cloning assay as described previously[95]. Briefly, cells were preincubated with nystatin and anti-ceramide mAb, or vehicle and control IgM in RPMI+0.5% lipid-free fetal bovine serum, and stimulated with increasing doses of UV-C or anti-Fas for 4 hours. Subsequently, cells were suspended in RPMI medium containing 20% FBS, 20 mM L-glutamine and 40% methylcellulose medium, and plated in triplicate. After 14-16 days of incubation, plates were analyzed by inverted microscope and aggregates with more than 20 cells were scored as colonies. Colony formation for each condition calculated in relation to values obtained for untreated control cells. Colony survival curves were calculated by least square regression analysis, using a modification of the FIT software program[96]. The program fits the curves by iteratively weighted least squares to each set of dose-survival data, estimates the covariates of the survival curve parameters and the corresponding confidence regions, and plots the survival curve. It also derives curve parameters, such as the $D_o$ (the reciprocal of the slope on the exponential portion of the curve, representing the level of radiosensitivity) and the N number (measuring the size of the shoulder).

Platform Detection

Platforms were detected as previously described. Briefly, $1 \times 10^6$ Jurkat cells were stimulated with UV-C or α-Fas, fixed with 2% paraformaldehyde at the indicated times, blocked in PBS containing 1% fetal bovine serum, and then washed with PBS. Cells were stained for the raft-localized lipid GM1 with FITC-conjugated cholera toxin β-subunit (2 gg/ml; Sigma-Aldrich) for 45 min at 4° C., washed twice in PBS containing 0.1% Triton X-100 and mounted in fluorescent mounting medium (Dako, Carpenteria Calif.). Fluorescence was detected using an Axiovert S-100 Zeiss fluorescence microscope equipped with a SPOT digital camera. The percentage of cells containing platforms, i.e. those in which the fluorescence condenses onto less than 15% of the cell surface, was determined by counting 150-250 cells per point. Alternately, platforms were identified using a mouse monoclonal anti-ceramide antibody MID 15B4 IgM (1:50 dilution, Alexis Biochemicals), mouse monoclonal anti-Fas CH-11 IgM (1:500 dilution, Upstate Biotechnology) or polyclonal rabbit anti-ASMase antibody 1598 (1:100 dilution) and detected using Cy3-conjugated anti-mouse or anti-rabbit IgM (1:500 dilution, Roche Molecular Biochemicals), respectively. Rabbit polyclonal anti-CD46 (1:1000 dilution, Santa Cruz Biotechnology, Santa Cruz Calif.) was used as a negative control. In some studies, confocal images were obtained using a Leica TCS SPZ upright confocal microscope. Alternatively, $0.5 \times 10^6$ hepatocytes were stimulated for the indicated times with CTLs and platform formation was assessed as described.

The rabbit polyclonal anti-ASMase antibody #1598 was generated against full-length FLAG-tagged human ASMase protein. Anti-sera was purified over a BIO-RAD T-Gel Column to obtain an IgG fraction that displays specific immunoreactivity by immunoblot assay at a concentration of 100 ng/μl towards 100 ng of purified recombinant human ASMase or ASMase from 25 μg of Jurkat cell lysates. At a concentration of 200 μg/μl, #1598 quantitatively immunoprecipitates ASMase activity from 100 ng of purified ASMase and at a concentration of 200 ng/μl detects cell surface expression of ASMase by flow cytometry or confocal immunofluorescence microscopy.

Diacylglycerol Kinase Assay (DGK)

Jurkat cells, stimulated with UV-C or CH-11, were incubated for the indicated times at 37° C. Stimulation was terminated by the addition of 2 ml of chloroform:methanol:HCl (100:100:1, v/v/v), and ceramide was quantified by the diacyglycerol kinase assay, as described[97].

Western Blot Analysis

Jurkat cells stimulated with UV-C or CH-11 were incubated for the indicated times at 37° C. Stimulation was terminated with ice-cold PBS and cells were lysed in RIPA buffer (25 mM HEPES (pH 7.4), 0.1% SDS, 0.5% sodium deoxycholate, 1% Triton X-100, 100 mM NaCl, 10 mM NaF, 10 mM $Na_2P_2O_7$, 10 mM EDTA and 10 μg/ml each aprotonin and leupeptin). Samples were centrifuged at 14,000 g and the supernatants were added to 4×SDS-sample buffer. Lysates were separated on a 10% SDS-PAGE gel and transferred onto nitrocellulose membranes. Caspase cleavage was detected using rabbit polyclonal antibodies against caspase 3 (BD PharMingen, San Diego Calif.), caspase 8 (BD PharMingen) or caspase 9 (Cell Signaling Technology, Beverly Mass.). Caspase 8 and FADD expression levels were detected using mouse monoclonal anti-caspase 8 (clone 1-1-37; Upstate Biotechnology) or anti-FADD (BD PharMingen) antibodies, respectively.

Flow Cytometry Analyses

To detect surface ASMase by FACS, Jurkat cells were stimulated with 50 $J/m^2$ UV-C or 50 ng/ml CH-11 at 37° C. Stimulation was terminated after 1 min, the time of maximal ASMase translocation, by addition of ice-cold washing buffer (PBS containing 1% FCS and 0.1% $NaN_3$), and cells were blocked on ice for 20 min using the same buffer supplemented with isotype control rabbit IgG (20 μg/ml). Cells were re-washed and incubated for 45 min with 14 g/ml of polyclonal anti-ASMase 1598 antibody in PBS, followed by washing and incubation with Cy3 conjugated anti-rabbit IgG. 10,000 cells were analyzed using a FACScan flow cytometer (Becton Dickinson, Franklin Lakes N.J.).

Harvested splenocytes were washed, incubated with CD16/CD32 FcR block on ice for 15 min, subsequently incubated with primary antibodies for 45 min, washed, resuspended in FACS buffer (PBS+2% BSA+0.1% $NaN_3$) and analyzed on a FACScan flow cytometer with CellQuest software (Becton Dickinson). For CFSE staining, RBC-lysed LP/J or B10.BR splenocytes were positively selected as per manufacturer's instruction with anti-CD3 microbeads (Miltenyi, Auburn, Calif.), stained in 2.5 μM carboxyfluorescein diacetate succinimidyl ester (CFSE) and $15-20 \times 10^6$ stained cells were transplanted into allogeneic (B6) recipients of either asmase$^{+/+}$ or asmase$^{-/-}$ background. Splenocytes from these animals were harvested 72 hrs thereafter, stained with fluorochrome-conjugated antibodies for surface antigens and FACS analysis was carried out as above.

ASMase Activity Assay

ASMase activity was measured using a fluorescence-based, high-performance liquid chromatographic (HPLC) assay[98]. Briefly, 5×10$^6$ Jurkat cells were stimulated with 50 J/m$^2$ UV-C or 50 ng/ml CH-11 at 37° C., and at the indicated times washed with ice-cold PBS and lysed on ice in NP-40 buffer (150 mM NaCl, 25 mM Tris HCl pH 7.5, 10% glycerol, 1% NP-40, 2 mM EDTA, 0.1 M DTT supplemented with PMSF, leupeptin and protease inhibitor cocktail). ASMase activity was measured by incubating an equal volume of lysate in assay buffer [500 μM BODIPY-C$_{12}$ sphingomyelin (Molecular Probes, Eugene Oreg.), 0.1 mM ZnCl$_2$, 0.1 M sodium acetate pH 5.0 and 0.6% Triton X-100] for 60 min at 37° C. Thereafter, the reaction was stopped by 10× dilution in ethanol and 5 μl of the assay mixture was sampled by a WIPS 712 (Waters Corp., Milford Mass.) auto-sampler equipped with a 20×4 mm reverse-phase Aquasil C$_{18}$ column (Keystone Scientific, Bellefonte Pa.). The reaction product, BODIPY-C$_{12}$ ceramide, was specifically separated from substrate within 0.4-0.5 min by isocratic elution with 95% MeOH at a flow rate of 1.2 ml/min. Fluorescence was quantified using a Waters 474 (Waters Corp.) fluorescence detector set to excitation and emission wavelengths of 505 and 540 nm, respectively. The amount of product generated was calculated using a regression equation derived from a standard curve established for known amounts of BODIPY-C$_{12}$ ceramide standard. Alternatively, ASMase activity was quantified by radioenzymatic assay using [$^{14}$C-methylcholine]sphingomyelin (Amersham Biosciences, Piscataway, N.J.) as substrate, as described[14]. Briefly, Jurkat cells were lysed in PBS containing 0.2% Triton X-100 at the indicated times after 50 J/m$^2$ UV-C or 50 ng/ml CH-11 stimulation. Post nuclear supernatants were assayed for activity in 250 mM sodium acetate, pH 5.0 supplemented with 0.1 mM ZnCl$_2$, 1 mM EDTA and 0.1% Triton X-100 in the presence of substrate. Reactions were terminated after 1 hour with CHCl$_3$:MeOH: 1N HCl (100:100:1, v/v/v), and product was quantified by scintillation counter. As both assays yielded identical fold increases after UV-C or Fas stimulation, these data were collated. However, BODIPY-C$_{12}$ sphingomyelin was less efficiently catalyzed resulting in a lower Vmax as determined by Michaelis Menton kinetic analysis. Thus, baseline ASMase specific activity, derived from the radioenzymatic assay, is displayed throughout the manuscript.

Radiation and Tissue Preparation

TBI was delivered with a Shepherd Mark-I unit (Model 68, SN643) operating $^{137}$Cs sources. The dose rate was 2.12 Gy/min. To collect small intestinal samples, mice were sacrificed by hypercapnia asphyxiation and 2.5 cm segments of the proximal jejunum were obtained at 2 cm from the ligament of Trietz. Tissue samples were fixed by overnight incubation in 4% neutral buffered formaldehyde and embedded in paraffin blocks. To evaluate intestinal tissue responses to radiation, transverse sections of the full jejunal circumference (5 μm thick) were obtained by microtomy from the paraffin blocks, adhered to polylysine-treated slides and deparaffinized by heating at 90° C. for 10 minutes and at 60° C. for 5 minutes, followed by two xylene washes for 5 minutes, and stained with hematoxylin and eosin according to a standard protocol. To determine the causes of death after TBI, autopsies were performed within 60 min of animal death or when terminally-sick animals displaying an agonal breathing pattern were sacrificed by hypercapnia asphyxiation. Tissue specimens were collected from all animals, fixed in formaldehyde, and stained with hematoxylin.

Crypt Microcolony Survival Assay

The microcolony survival assay was performed as described by Withers and Elkind[99]. Briefly, 3.5 days after irradiation mice were sacrificed by hypercapnia asphyxiation and samples of the small intestine were harvested and prepared for histological staining as described above. Surviving crypts were defined as containing 10 or more adjacent chromophilic non-Paneth cells, at least one Paneth cell and a lumen. The circumference of a transverse cross section of the intestine was used as a unit. The number of surviving crypts was counted in each circumference. 10-20 circumferences were scored per mouse and 2-4 mice were used to generate each data point. Data were reported as mean±SEM.

Assessment of GVHD

Survival was monitored daily, and ear-tagged animals in coded cages were individually scored weekly for 5 clinical parameters (weight loss, hunched posture, decreased activity, fur ruffling, and skin lesions) on a scale from 0 to 2. A clinical GVHD score was generated by summation of the 5 criteria scores (0-10) as described by Cooke et al[100]. GVHD target organ pathology for bowel (terminal ileum and ascending colon), liver and skin (tongue and ear) was assessed by one individual (J.M.C. for liver and intestinal pathology, G.F.M. for cutaneous pathology) in a blinded fashion on 10% formalin-buffered phosphate-preserved, paraffin-embedded and hematoxylin/eosin-stained 5 μM histopathology sections with a semiquantitative scoring system. Briefly, bowel and liver were scored for 19 to 22 different parameters associated with GVHD as described[101] and skin was evaluated for the number of dyskeratotic and apoptotic cells, as published[102] Villus and crypt cell apoptosis were scored on formalin-preserved, paraffin-embedded, TUNEL-stained and hematoxylin/eosin-counterstained sections, as described[18,62].

ELISA

Enzyme-linked immunosorbent assays (ELISA) for serum IL-1β, IL-2, IFN-γ and TNF-α levels was performed according to the manufacturer's instructions (R&D, Minneapolis, Minn.).

Activation-Induced Cell Death (AICD) Assay

Harvested splenocytes were enriched for T lymphocytes by nylon wool passage, resulting in >90% purity based upon FITC-CD3 mAb staining by flow cytometry. AICD was induced as previously reported[103]. Briefly, T cells were incubated in RPMI 1640+10% FCS at 2×10$^6$/mL and primed with 10 μg/ml ConA (Sigma, St. Louis, Mo.) for 48 hrs. Cells were then washed and rested in medium containing 20 U/mL L-2 (R&D Systems) for 24 hrs. Finally, cells were washed and resuspended in medium containing 20 U/mL L-2 and increasing amounts of anti-CD3 mAb (0-10 μg/ml) for 24 hrs. Cells were subsequently fixed, stained with 25 μl of 24 μg/ml bis-benzimide trihydrochloride solution (Hoechst #33258; Sigma-Aldrich, Milwaukee Wis.) and apoptosis was quantified by fluorescence microscopy, as above.

Mixed Lymphocyte Reactions (MLR)

Balb/c splenocytes were in vitro activated by incubation with 2×10$^6$ irradiated (2000 rad) C57BL/6 splenocytes in RPMI 1640+10% FCS for 5 days. 2 days prior to the MLR, asmase$^{+/+}$ or asmase$^{-/-}$ splenocytes were activated with 10 μg/mL con A for 48 hrs, labeled for 45 min with 1 μCi/mL Na$_2$ $^{51}$CrO$_4$ at 37° C. and 5% CO$_2$, washed in RPMI 1640+10% FBS, and coincubated with activated Balb/c splenocytes in complete medium for 24 hrs at 37° C. Target cell lysis was quantified by counting $^{51}$Cr release into the supernatant by gamma counter (Cobra, Meriden, Conn.) using the formula corrected % lysis=100× (sample $^{51}$Cr release–control $^{51}$Cr release)/(maximum $^{51}$Cr release–control $^{51}$Cr release).

Statistics

Actuarial survival of animals was calculated by the product limit Kaplan-Meier method[104] and statistical significance of differences in survival were calculated by the Mantel log-rank test[105]. Crypt survival curves were calculated by least square regression analysis, using a modification of the FIT software program[96]. The program fits the curves by iteratively weighted least squares to each set of dose-survival data, estimates the covariates of the survival curve parameters and the corresponding confidence regions, and plots the survival curve. It also derives curve parameters, such as the $D_o$ (the reciprocal of the slope on the exponential portion of the curve, representing the level of radiosensitivity) and the N number (measuring the size of the shoulder). Statistical analysis of GVHD scores, thymocyte and splenocyte number, and proliferation assays was performed using the nonparametric unpaired Mann-Whitney Utest. Student's t-test with 95% confidence estimations was used for all other analyses.

Example 2

Role of Asmase in GvHD

Figure 22C:
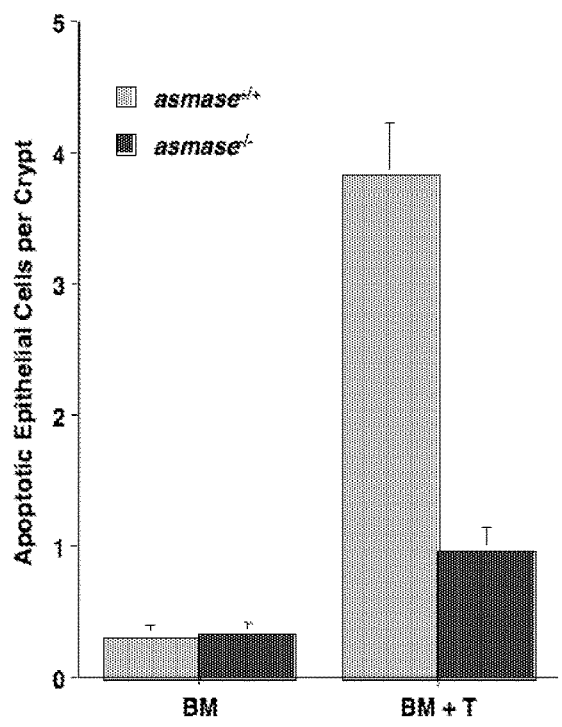

Small intestine, liver and skin were harvested from asmase$^{+/+}$ and asmase$^{-/-}$ recipients 21 days following transplantation of BM with or without 3×10$^6$ T cells. Hematoxylin & Eosin stained liver sections revealed hepatic GvHD, characterized by lymphocyte infiltration (FIG. 22A, arrows), portal tract inflammation, endotheliitis (FIG. 22A, right panels) and loss of hepatic architecture was less prominent in asmase$^{-/-}$ compared to asmase$^{+/+}$ recipients. Similarly, intestinal GvHD, including villus blunting, lamina propria inflammation, crypt stem cell loss and destruction and mucosal atrophy were less prominent in asmase$^{-/-}$ recipients (FIG. 22B, arrows indicate apoptotic cells). Semiquantitative histopathologic analyses revealed that asmase$^{+/+}$ recipients of allogeneic bone marrow and T cells scored significantly higher than littermates receiving only BM in liver (Table 1, 15.7±1.5 vs. 8.3±2.7, p<0.05) and small intestine (Table 2, 10.7±1.1 vs. 3.5±0.5, p<0.01). ASMase deficiency largely protected GvHD-associated organ damage, decreasing scoring to 10.2±0.5 and 7±0.1 in liver and small intestines, respectively (Table 2, p<0.005 each for liver and intestine vs. asmase$^{+/+}$ littermates).

Figure 22D:
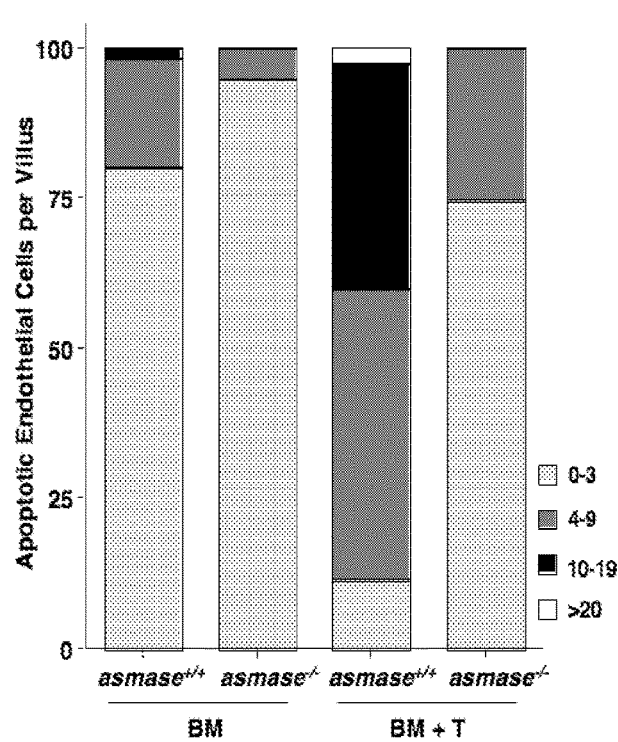
Figure 22E:
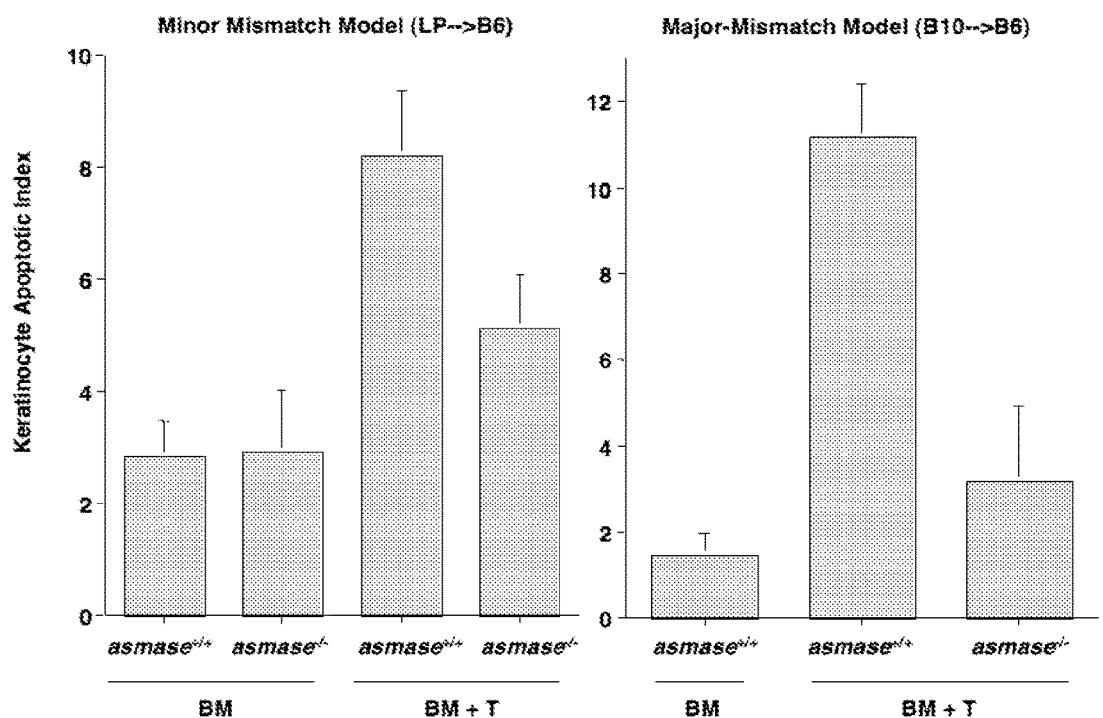

GvHD-associated organ injury is associated with prominent intestine and skin apoptosis. TUNEL-stained ileum sections revealed prominent incidence of apoptotic cells within the lamina propria (FIG. 22C) and crypt epithelium (FIG. 22D) of asmase$^{+/+}$ recipients of BM and T cells. asmase$^{+/+}$ recipients of allogeneic T cells exhibited massive apoptosis (>4 apoptotic cells per villus) in 88.4% of villi, which was decreased to 25.4% in asmase$^{-/-}$ recipients (FIG. 22C, p<0.05) and 3.8±0.4 apoptotic epithelial cells per crypt, attenuated to 0.95±0.2 in asmase$^{-/-}$ recipients (FIG. 22D, p<0.05). Further, ASMase deficiency protected hosts from cutaneous keratinocyte apoptosis following minor antigen-mismatched allogeneic BMT (FIG. 22E). Allogeneic T cells induced 5.1±0.9 apoptotic cells/mm in asmase$^{-/-}$ epidermis, compared to 8.2±2.1 apoptotic cells/mm of asmase$^{+/+}$ epidermis (p<0.05). These data demonstrate that ASMase tissue are resistant to GvH-associated apoptosis and organ injury, showing that ASMase regulates GvH-induced morbidity and mortality by determining target organ injury and apoptosis. To confirm a specific role for host ASMase in GvHD, a major histocompatability-incompatible allogeneic BM transplantation model of B10.BR donor (H-2$^k$) into C57BL/6 recipient (H-2$^b$) was selected. Lethally-irradiated C57BL/6 hosts of ASMase$^{+/+}$ or ASMase$^{-/-}$ background received 10×10$^6$ T-cell depleted (TCD) B10.BR BM cells, and GvHD was induced by the addition of 0.5×10$^6$ B10.BR donor splenic T cells to the allograft. Consistent with the minor-mismatched model, significantly less target organ damage was observed in asmase$^{-/-}$ hosts compared to asmase$^{+/+}$ littermates 14 days following transplantation of BM and T cells (Table 1, liver pathology scores of 16.3±1.1 in asmase$^{+/+}$ vs. 7.4±0.9 in asmase$^{-/-}$ hosts, p<0.05, and small intestine pathology scores of 10.0±0.8 in asmase$^{+/+}$ vs. 3.5±0.4 in asmase$^{-/-}$ hosts, p<0.05). These data are consistent with diminished crypt epithelium apoptosis (59.3±3.8% of crypts containing apoptotic cells in wild type vs. 15.8±3.7% in asmase$^{-/-}$ hosts, p<0.05, not shown) and reduced hepatic lymphocyte infiltration, endotheliitis and overall destruction of the hepatic architecture (not shown). Further, keratinocyte apoptosis was prominent in wild type hosts, reaching an apoptotic index of 11.2±1.2 apoptotic cells/mm$^2$ epidermis that was significantly attenuated in asmase$^{-/-}$ hosts to 3.2±1.7 (FIG. 22E, p<0.01). However, Kaplan-Meier survival could not be determined in this major mismatched model due to a late (>day 21 post BMT) BM aplasia, accredited to a genetic shift in the B10.BR strain detected and described on the Jackson laboratory website. Taken together, these data identify a significant attenuation of GvHD-associated target organ damage and apoptosis, closely correlating with protection against GvH morbidity and mortality, in asmase$^{-/-}$ hosts compared to wild type littermates across both minor and major antigen disparities.

TABLE 2

Host asmase$^{-/-}$ mediates graft-vs.-host target organ injury and apoptosis.

| Transplan | Minor-Mismatch Model (LP→B6) | | Major-Mismatch Model (B10→B6) | |
|---|---|---|---|---|
| | Liver | Liver | Liver | Small Intestine |
| t BM (asmase$^{+/+}$ hosts) | 8.3 ± 2.7 | 8.3 ± 2.7 | 1.0 ± 0.0 | 2.0 ± 0.0 |
| BM (asmase$^{-/-}$ hosts) | 7.1 ± 0.9 | 7.1 ± 0.9 | 0.7 ± 0.3 | 1.5 ± 0.5 |
| BM + T (asmase$^{+/+}$ hosts) | 15.7 ± 1.5* | 15.7 ± 1.5* | 16.3 ± 1.1* | 10.0 ± 0.8* |
| BM + T (asmase$^{-/-}$ hosts) | 10.2 ± 0.5** | 10.2 ± 0.5** | 7.4 ± 0.9** | 3.5 ± 0.4 |

C57BL/6 recipient hosts received LP BM and T cells (minor mismatch) as described in FIG. 1, or alternatively, received 10 × 10$^6$ BM and 0.5 × 10$^6$ T cells from B10.BR donors (major mismatch).
asmase$^{+/+}$ and asmase$^{-/-}$ recipients were sacrificed 14 (B10. BR recipients) or 21 (LP recipients) days post BMT, and tissues were harvested for histopathologic analysis.
Small intestine, large intestine and liver were scored for established organ-specific parameters in a blinded fashion (mean ± SEM) for 4-14 animals per group.
*indicates p < 0.01 vs. BM group (asmase$^{+/+}$ hosts),
**indicates p < 0.01 vs. BM + T (asmase$^{+/+}$ hosts).

TABLE 3

| | BM asmase$^{+/+}$ hosts | BM asmase$^{-/-}$ hosts | BM + T asmase$^{+/+}$ hosts | BM + T asmase$^{-/-}$ hosts |
|---|---|---|---|---|
| Minor-Mismatch Model (LP□B6) | | | | |
| IL-2 (pg/ml) | 15.7 ± 4.1 | 13.0 ± 1.6 | 30.3 ± 2.8* | 19.1 ± 2.0** |
| IFN-γ (pg/ml) | 3.7 ± 1.0 | 1.3 ± 0.4 | 109.9 ± 18.9* | 32.8 ± 12.4** |
| IL-1β (fg/ml) | 6.8 ± 1.9 | 5.5 ± 0.5 | 13.4 ± 1.1* | 2.9 ± 1.2** |
| TNF-α (pg/ml) | 2.3 ± 1.2 | 5.2 ± 1.0 | 24.3 ± 7.1* | 17.3 ± 3.0 |
| Major-Mismatch Model (B.10□B6) | | | | |
| IFN-γ (pg/ml) | 4.1 ± 1.0 | 3.6 ± 1.9 | 199.1 ± 14.2* | 63.3 ± 10.8** |
| TNF-α (pg/ml) | 33.0 ± 1.9 | 16.7 ± 2.3 | 136.8 ± 11.5* | 63.7 ± 9.0** |

Table 3. Host Asmase$^{-/-}$ Regulates Graft-Vs.-Host-Induced Serum Cytokine Expansion.

Host C57BL/6 were transplanted with LP/J TCD-BM with or without splenic T cells as described in Example 1 and serum was obtained from peripheral blood on day 7 post marrow transplant by retro-orbital puncture. Serum Th1 (IL-2 and IFN-γ) and Th2 (IL-1β and TNF-α) cytokines levels were quantified by ELISA, as described in Example 1. Serum cytokine levels (mean±SEM) compiled from 3-8 determinations from three independent experiments for each group are depicted. * p<0.005 vs. BM; ** p<0.01 vs. asmase$^{+/+}$.

Example 3

ASMase Deficiency Protects Against Inflammation

We next conducted experiments showing that host ASMase inactivation attenuates Th1/Th2 cytokine profile and CD8$^+$ T cell proliferation in acute GvHD. Initial CTL-mediated tissue damage propagates a feed-forward response requiring CD4$^+$ Th1 cytokine secretion and consequent alloreactive CD8$^+$ clonal expansion for acute GvHD to proceed, followed by inflammatory cytokine storm. To assess the impact of ASMase on serum cytokine levels during GvHD, serum Th1 cytokines IL-2 And IFN-γ and Th2 cytokines IL-1β and TNF-α were quantified 7 and 14 days following transplantation of LP BM with or without splenic T cells. In the minor mismatched model, addition of T cells to the allograft increased IL-2 and IFN-γ from 15.7±4.1 to 30.3±2.8 and 3.7±1.0 to 109.9±18.9 pg/ml serum, respectively (p<0.05 for each) on day 7 compared to BM control recipients (Table 3). Th2 cytokines IL-1β and TNF-α similarly increased from 6.8±1.9 to 13.4±1.1 and 2.3±1.2 to 24.3±7.0 pg/ml serum, respectively (p<0.05 for each) on day 7 compared to BM control recipients (Table 3). Genetic inactivation of host ASMase reduced serum IL-2 and IFN-γ to 19.1±2.0 and 32.8±12.4 pg/ml serum, respectively, (p<0.05 vs. asmase$^{+/+}$ hosts) and IL-1β and TNF-α to 2.9±1.2 and 17.3±3.0 pg/ml serum, respectively, (p<0.05 vs. asmase$^{+/+}$ hosts and not significant) on day 7 (Table 3). Attenuation of serum cytokines was preserved across major mismatched model of donor B10.BR BM and T cells into C57BL/6 hosts (Table 2, 199.1±14.2 vs. 63.3±10.8 pg/ml IFN-γ in asmase$^{+/+}$ vs. asmase$^{-/-}$ hosts p<0.05, 136.8±11.5 vs. 63.7±9.0 pg/ml TNF-α in asmase$^{+/+}$ vs. asmase$^{-/-}$ hosts p<0.005), demonstrating that ASMase deficiency generally attenuated serum cytokine production in recipients of allogeneic BM and T cells.

Increased serum cytokine levels directly impact T cell expansion[111]. To assess whether attenuation of serum cytokines in asmase$^{-/-}$ recipients of BM and T cells impacts donor T cell proliferation, carboxyl fluorescein succinimidyl ester (CFSE)-labeled T cells (10-20×10$^6$) from LP/J (H-2$^b$, Minor MHC-incompatible) or B10.BR (H-2$^k$, Major MHC-incompatible) donors were infused into lethally-irradiated C57BL/6 hosts of asmase$^{+/+}$ or asmase$^{-/-}$ background. While in vivo expansion of both LP and B10.BR CD4$^+$ T cells were not statistically different in asmase$^{-/-}$ compared to asmase$^{+/+}$ littermates (FIG. 23A upper panels and not shown for B10.BR), CD8$^+$ T cell proliferation was significantly impaired across both minor (FIG. 12A) and major MHC (not shown) disparate models. Three days following infusion, proliferating CD8$^+$ cells constituted 54.1% of the total donor LP CD8$^+$ T cell population in asmase$^{+/+}$ hosts, compared to 26.4% of the population recovered from asmase$^{-/-}$ hosts (FIG. 23A lower panels, p<0.005). Similarly, proliferating donor B10.BR CD8$^+$ cells were reduced from 81.5% of the total population in asmase$^{+/+}$ hosts to 67.1% in asmase$^{-/-}$ hosts (not shown, p<0.005). Further, attenuated proliferation resulted at 14 days following infusion of BM and 3×10$^6$ T cells in significant reduction of splenic donor LP/J CD8$^+$ T cells from 1.69±0.28×10$^6$ cells in asmase$^{+/+}$ recipients to 0.55±0.28×10$^6$ in asmase$^{-/-}$ recipients, (FIG. 23B, p<0.001).

Figure 24:
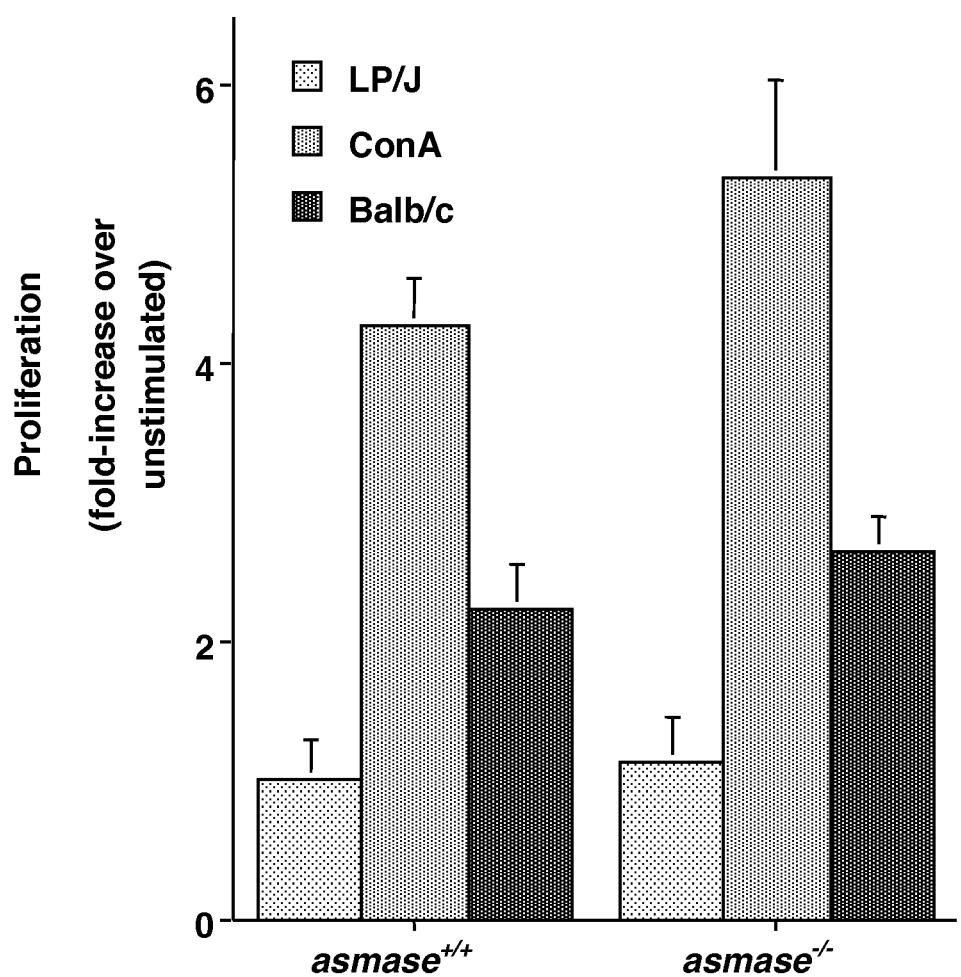
FIG. 24. T cell proliferative capacity remains intact in asmase$^{-/-}$ hosts. Thymidine incorporation assay measuring proliferation of splenic T cells harvested from C57BL/6$^{asmase+/+}$ or C57BL/6$^{asmase-/-}$ recipients of donor LP BM and T cells in response to syngeneic (LP) or allogeneic (Balb/c) splenocytes or mitogen (ConA). Data (mean±SEM) represent triplicate determinations from three independent experiments FIG. 25. 1H4, 5H9 and 15D9 hybridoma cell lines were established after six subclonings. Hybridoma supernatants were screened in a Jurkat cell apoptosis inhibition assay and showed protective effects that are dose dependent and comparable to 2A2. The isotypes of the three antibodies have been established. 15D9 mAb is IgM, kappa. 1H4 and 5H9 mAbs are mIgG3, kappa.

Despite impairment of proliferation in vivo, T cell proliferative capacity remained intact upon transplantation into asmase$^{-/-}$ hosts, as splenic T cells from asmase$^{-/-}$ or asmase$^{+/+}$ hosts allografted with LP/J TCD-BM and T cells displayed similar specific proliferative responses ex vivo when challenged with conA (FIG. 24). T cell proliferative capacity remains intact in asmase$^{-/-}$ hosts. Thymidine incorporation assay measuring proliferation of splenic T cells harvested from C57BL/6$^{asmase+/+}$ or C57BL/6$^{asmase-/-}$ recipients of donor LP BM and T cells in response to syngeneic (LP) or allogeneic (Balb/c) splenocytes or mitogen (ConA). Data (mean±SEM) represent triplicate determinations from three independent experiments).

Further, ex vivo alloactivation of T cells derived from asmase$^{+/+}$ and asmase$^{-/-}$ hosts 21 days post transplantation with LP/J BM+T cells were similar, as proliferation was intact in response to irradiated third party T cell challenge (Balb/c), and absent in response to irradiated LP/J T cells (FIG. 23). These data demonstrate deficient in vivo CD8$^+$ CTL proliferation in asmase$^{-/-}$ hosts, and show a biologically-relevant consequence to the attenuation of serum proinflammatory cytokine levels in these BMT recipients.

Example 4

Methods for Making 2A2 Antibody
Hybridoma Generation

C57BL/6 mice underwent eight immunizations with Kaposi's Sarcoma cells, and serum was collected for evaluation by ELISA. Alternatively, mice were immunized with BSA-conjugated $C_{16}$-ceramide. Serum was tested for ceramide-binding by ELISA, and animals testing positive were sacrificed. Peripheral lymph nodes were harvested and macerated to release B cells. PEG mediated fusion was performed on the purified B cells using Sp2/0 myeloma cells, and the fusions were plated in culture plates containing HAT-supplemented DMEM. Hybridomas were subsequently fed on day 5, and supernatants were collected on day 10 and tested for ceramide binding by ELISA. Clones were determined positive only if supernatants bound ceramide but not BSA or $C_{16}$-dihydroceramide. Positive clones were expanded in HT-supplemented DMEM, subcloned by limiting dilution, and re-evaluated by ELISA.

ELISA Assay

Antigen (BSA-conjugated $C_{16}$ ceramide, BSA-conjugated $C_{16}$ dihydroceramide or BSA) was absorbed onto a NUNC Maxisorp Immunoplate by incubation overnight at 4° C. Unbound antigen was washed by phosphate buffered saline (PBS) containing 0.05% Tween20, and plates were saturated with PBS containing 5% milk. Hybridoma supernatant or primary antibody incubation was performed for 2 hrs at room temperature. Following 3 washes in PBS+0.05% Tween20, secondary antibody incubation (HRP-conjugated anti-mouse antibody) was performed for 2 hrs at room temperature. Following an additional 3 washes, antibody binding was detected using 3,3',5,5'-tetramethylbenzidine (TMB), stopped using an acidic solution and absorbance was quantified at 450 nm.

Antibody Purification

Tissue culture supernatants from hybridomas were sterile filtered and mixed with pre-washed protein G for 1 hr at 4° C. Protein G was collected and washed with 10 volumes of PBS. Antibodies were eluted with 50 mM citrate, 140 mM NaCL, pH 2.7. Antibody containing fractions were neutralized by Tris, dialyzed and antibody was purified by column affinity. Antibody was eluted using NaCL gradient. Antibody was dialyzed against 25 mM phosphate, 100 mM NaCL, pH 5.8, aliquoted at 1 mg/ml and stored at −20° C.

Methods for Making 2A2 Antibody
Generation of Monoclonal Antibodies.

Five 8-week-old female BALB/c mice were immunized with 0.5 ml of Kaposi Sarcoma cells ($4 \times 10^7$/ml) via IP. The animals were immunized three times, once per week. Mice were bled 1 week after the last immunization, and the antibody responses in the antiserum were evaluated by FACS analysis. One mouse was chosen for hybridoma preparation. It received an additional boost of KS cells three days before the cell fusion. Splenocytes from the BALB/c mice immunized with KS cells were fused with mouse myeloma cells (P3X63Ag8.653, ATCC) at a 4:1 ratio using polyethylene glycol (MW 1500). After fusion, cells were seeded and cultured in 96-well plates at $1 \times 10^5$ cells/well in the RPMI 1640 selection medium containing 20% fetal bovine serum, 10% Hybridoma supplements (Sigma), 2 mM L-glutamine, 100 U/ml penicillin, 100 mg/ml streptomycin, 10 mM HEPES, and 1× hypoxanthine-aminopterin-thymidine (Sigma). Hybridoma supernatants were screened by FACS analysis on KS cells and ELISA using commercial available proteins mixture (Annexin V, Ceramide-BSA and APA). Selected hybridomas were subcloned four times by limited dilution and screened by ELISA on Annexin V coated plates. Conditional media were harvested from the stable hybridoma cultures. The Ig class of mAb was determined with a mouse mAb isotyping kit (Santa Cruz). 2A2 mIgM was purified from ascites by using an immobilized mannan binding protein beads. 2A2 mAb (mIgM) that bind to Annexin V has weak cross-binding activity to Ceremide was confirmed by ELISA.

Antibody Humanization.

General molecular cloning techniques (RT-PCR or 5'-RACE) are used to obtain the variable regions for both heavy ($V_H$) and light ($V_L$) chains of a murine 2A2 antibody. A chimeric 2A2 antibody will be generated to confirm binding properties equivalent to that of the murine parent. Chimeric 2A2 antibody will be humanized by using complementarity determining region (CDR) grafting. The human framework sequences from the set of human germ line genes will be chosen based on similarity of the human antibody's CDRs to the mouse 2A2 antibody's CDRs. The antibody will be further engineered to fine tune the structure of the antigen-binding loops by replacing key residues in the framework regions of the antibody variable regions to improve antibody affinity and production.

What is claimed is:

1. A method of inhibiting Fas-mediated death of a cell comprising exposing the cell to an effective amount of an inhibitor of ceramide-rich platform (CRP) formation,
   wherein the inhibitor of CRP formation is an anti-ceramide antibody or antigen binding fragment comprising the $V_H$ CDR 1-3 and $V_L$ CDR 1-3 sequences of the 2A2 anti-ceramide antibody produced by the hybridoma deposited under international deposit number PTA-13418.

2. A method of inhibiting Fas-mediated death of a cell in a subject in need thereof comprising administering an effective amount of an inhibitor of ceramide-rich platform (CRP) formation to the subject,
   wherein the inhibitor of CRP formation is an anti-ceramide antibody or antigen binding fragment comprising the $V_H$ CDR 1-3 and $V_L$ CDR 1-3 sequences of the 2A2 anti-ceramide antibody produced by the hybridoma deposited under international deposit number PTA-13418.

3. The method of claim 2, wherein the subject is a bone marrow transplant recipient.

4. The method of claim 2, wherein the subject suffers from graft-versus-host disease.

5. A method of inhibiting Fas-mediated death of a cell in a subject suffering from an autoimmune disease comprising administering an effective amount of an inhibitor of ceramide-rich platform (CRP) formation to the subject,
   wherein the inhibitor of CRP formation is an anti-ceramide antibody or antigen binding fragment comprising the $V_H$ CDR 1-3 and $V_L$ CDR 1-3 sequences of the 2A2 anti-ceramide antibody produced by the hybridoma deposited under international deposit number PTA-13418.

6. The method of claim 5, wherein the autoimmune disease is graft-versus-host disease.

\* \* \* \* \*